US007238513B2

(12) United States Patent
Bulaj et al.

(10) Patent No.: US 7,238,513 B2
(45) Date of Patent: Jul. 3, 2007

(54) **NUCLEIC ACID SEQUENCES ENCODING *CONUS* PROTEIN DISULFIDE ISOMERASE**

(75) Inventors: Grzegorz Bulaj, Salt Lake City, UT (US); Baldomero M. Olivera, Salt Lake City, UT (US); Olga Buczek, Salt Lake City, UT (US); James E. Garrett, Salt Lake City, UT (US); Ian Goodsell, Sandy, UT (US)

(73) Assignees: University of Utah Research Foundation, Salt Lake City, UT (US); Cognetix, Inc., Salt Lake City, UT (US)

( * ) Notice: Subject to any disclaimer, the term of this patent is extended or adjusted under 35 U.S.C. 154(b) by 0 days.

(21) Appl. No.: 11/216,937

(22) Filed: Aug. 31, 2005

(65) Prior Publication Data

US 2006/0199245 A1    Sep. 7, 2006

Related U.S. Application Data

(63) Continuation of application No. 10/789,450, filed on Feb. 27, 2004, now abandoned.

(60) Provisional application No. 60/453,723, filed on Feb. 28, 2003.

(51) Int. Cl.
*C12N 9/00* (2006.01)
*C12N 9/90* (2006.01)
*C07H 21/04* (2006.01)
*C12P 21/06* (2006.01)

(52) U.S. Cl. ............... 435/233; 435/183; 435/69.1; 435/68.1; 435/320.1; 435/325; 435/419; 435/252.3; 435/254.11; 536/23.2

(58) Field of Classification Search ............ 435/183, 435/233, 69.1, 68.1, 320.1, 325, 419, 252.3, 435/254.11; 536/23.2
See application file for complete search history.

(56) References Cited

U.S. PATENT DOCUMENTS 6,346,244 B1    2/2002    Hjort

FOREIGN PATENT DOCUMENTS

| EP | 0 510 658 B1 | 10/1992 |
|----|--------------|---------|
| WO | WO 93/25676 | 12/1993 |
| WO | WO 94/08012 | 4/1994 |
| WO | WO 95/01420 | 1/1995 |
| WO | WO 95/01425 | 1/1995 |
| WO | WO 97/14431 | 4/1997 |
| WO | WO 97/43426 | 11/1997 |
| WO | WO 99/46281 | 9/1999 |
| WO | WO 01/14564 A2 | 3/2001 |
| WO | WO 02/20731 A2 | 3/2002 |

OTHER PUBLICATIONS

Folding of ro-Conotoxins. 2. Influence of Precursor Sequences and Protein Disulfide Isomerase. Marian Price-Carter, William R. Gray, and David P. Goldenberg. Sep. 1996. Biochemistry 1996, 35, 15547-15557.*
Karplus et al., Assignment of homology to genome sequences using a library of hidden Markov models that represent all proteins of known structure, J. Mol. Biol., Nov. 2, 2001, pp. 903-919, vol. 313, No. 4, Abstract.
IBA et al., Comparison of strategies for the construction of libraries of artificial antibodies, Immunol. Cell Biol., Apr. 1997, pp. 217-221, vol. 75, No. 2, Abstract.
Jayawickreme et al., Creation and functional screening of a multi-use peptide library, Proc. Natl. Acad. Sci., Mar. 1994, pp. 1614-1617, vol. 91, USA.
Klug, A, Zinc finger peptides for the regulation of gene expression, J. Mol. Biol., Oct. 22, 1999, pp. 215-218, vol. 293, No. 2.
Ogiwara et al., Construction and analysis of a profile library characterizing groups of structurally known proteins, Protein Sci., Oct. 1996, pp. 1991-1999, vol. 5, No. 10.
Saunder et al., Large-Scale Comparison of Protein Sequence Alignment Algorithms With Structure Alignments, Proteins: Structure, Function, and Genetics, 2000, pp. 6-22, vol. 40.
Schaffer et al., Improving the accuracy of PSI-BLAST protein database searches with composition-based statistics and other refinements, Nucleic Acids Research, 2001, pp. 2994-3005, vol. 29, No. 14, USA.
Smith et al., Small Binding Proteins Selected form a Combinatorial Repertoire of Knottins Displayed on Phage, J. Mol. Biol., 1998, pp. 317-332, vol. 277.
Valuev et al., ASPD (Artificially Selected Proteins/Peptides Databases): a database of proteins and peptides evolved in vitro, Nucleic Acids Research, 2002, pp. 200-202, vol. 30, No. 1.
Yamauchi et al., Bovine Protein Disulfide Isomerase. 1998. Accession AAP80615.
Toyoshima et al., Polypeptides with Protein Disulfide Activity. Accession AAP80664, 2002.

* cited by examiner

*Primary Examiner*—David J. Steadman
*Assistant Examiner*—Kagnew Gebreyesus
(74) *Attorney, Agent, or Firm*—TraskBritt

(57) ABSTRACT

Protein disulfide isomerase is a major component of *Conus* venom ducts. The invention relates to a protein disulfide isomerase (PDI) from *Conus* snails, a nucleic acid sequence encoding the *Conus* protein disulfide isomerase, and to methods for folding disulfide-rich peptides using a protein disulfide isomerase. Oxidative folding of conotoxin precursors, catalyzed by a PDI, was more efficient and decreased the number and concentration of transiently accumulated folding species. The PDI-assisted oxidative folding of conotoxins was also influenced by the propeptide relative to the mature peptide.

15 Claims, 11 Drawing Sheets

FIG. 2

PDI Species Comparison

```
                      10        20        30        40        50        60        70        80        90       100
Ct-PDI.ami            MKFSSCLVLTLIVFVSAEDVEQEENVHVLTKKNFDSPITDNEFVLVEFYAPWCGHCKALAPEYAKAATTLENEKSNIKLAKVDATVEGDLASKFDVR
Silkworm-PDI.am       MRVLIPTAIALLGLALGDEVPTEENVLVLSKANFETVISTTEYILVEFYAPWCGHCKSLAPEYAKAATKLAEEESPIKLAKVDATQEQDLAESYGVR
SeaUrchin-PDI.a       MKYLALCFIALACAVHAAVEVEIEEDVAVLTDAAFADYVAENEFVLVEFYAPWCGHCKSLAPQYSIAAKTLKDSGSSIKLAKVDATVETQLPGKYGVR
Rat-PDI.ami           MLSRALLCLALAWAARVGADALEEEDNVLVLKKSNFABALAAHNYLLVEFYAPWCGHCKALAPEYAKAAKLKAEGSEIRLAKVDATEESDLAQQYGVR
Human-PDI.ami         MLRRALLCLAVAALVR--ADAPEEEDHVLVLRKSNFAEALAAHKYLLVEFYAPWCGHCKALAPEYAKAAGKLKAEGSEIRLAKVDATEESDLAQQYGVR
Fly-PDI.ami           MKFLICALFLAASYVAASAEAEVKVEEGVLVATVDNFKQLIADNEFVLVEFYAPWCGHCKALAPEYAKAAQQLAEKESPIKLAKVDATVEGELAEQYAVR
Celegans-PDI.am       MFRLVGLFFLVLGASAAVIEEEENVIVLTKDNFDEVINGNEFILVEFYAPWCGHCKSLAPEYAKAATQLKEEGSDIKLGKLDATVHGEVSSKFEVR
                                                            .   *  ***********   ** ***  ** *     ** .  * **.*

110       120       130       140       150       160       170       180       190       200
Ct-PDI.ami            GYPTIKFFRKEKPDGPADYSGGRQAKDIVDWLKKKTGPPAKELKEDEVKAFVEKDEVVIGFFKDQESTGALAFKKAAAGIDDIPFAITSEDHVFKEYK
Silkworm-PDI.am       GYPTLKFFRNGS---PIDYSGGRQADDIISWLKKKTGPPAVEVTSAEQAKELIDANTVIVFGFFSDQSSTRAKTFLSTAQVDDQVFAIVSDEKVIKELE
SeaUrchin-PDI.a       GYPTLKFFRSGK---DSEYAGGRTGPEIVAWLNKKTGPPAATIASVEDAEEAFLADKEVAVIGFFKDVP----QTFLDVAVNIDDIPFAIVSDDAVISNYE
Rat-PDI.ami           GYPTIKFFKNGDTASPKEYTAGREADDIVNWLKKRTGPAATTLSDTAAAESLVDSSEVTVIGFFKDAGSDSAKQFLLAAEAVDDIPFGITSNSDVFSKYQ
Human-PDI.ami         GYPTIKFFRNGDTASPKEYTAGREADDIVNWLKKRTGPAATTLPDGAAAESLVESSEVAVIGFFKDVESDSAKQFLQAAEAIDDIPFGITSNSDVFSKYQ
Fly-PDI.ami           GYPTLKFFRSGS---PVEYSGGRQAADIIAWTKKTGPPAKDLTSVADAEQFLKDNELAIIGFFKDLESEEAKTFTKVANALDSFVFGVSSNADVIAKYE
Celegans-PDI.am       GYPTLKLFRNGK---PQEYNGGRDHDSIIAWLKKKKTGPVAKPLADADAVKELQESADVVVIGYFKDTTSDDAKTFLEVAAGIDDVPFGISTEDAVKSEIE
                     ****..*                            ...*               *.               .

210       220       230       240       250       260       270       280       290       300
Ct-PDI.ami            MDKDGIVLLKKFDEGRNDFEGNLEEEEAIVKHVRENQLPLVVEFTQESAQKIFGGEVKNHILLFLKK--EGGEDTIEKFRSAAEDFKGKVLFIYLDTDNE
Silkworm-PDI.am       AEDEDVVLFKNFEEKRVKYEDEEITEDLLNAWVFVQSMPTIVEFSHETASKIFGGKIKYHLLIFLSKKNGDFEKYLEDLKPVAKTYRDRIMTVAIDADED
SeaUrchin-PDI.a       AKDGSIILFKKFDEGKNVFEGEIT-SEDLTSFVRKNSLSVVTEFGEETASKIFGGEIKTHILLFLPKSVSDYDGKLSNFKKAAEGFKGKILFIFIDSDHT
Rat-PDI.ami           LDKDGVVLFKKFDEGRNNFEGEIT-KEKLLDFIKHNQLPLVIEFTEQTAPKIFGGEIKTHILLFLPKSVSDYDGKLSNFKTAAESFKGKILFIFIDSDHT
Human-PDI.ami         LDKDGVVLFKKFDEGRNNFEGEVT-KENLLDFIKHNQLPLVIEFTEQTAPKIFGGEIKTHILLFLPKSVSDYDGKLSNFKTAAESFKGKILFIFIDSDHT
Fly-PDI.ami           AKDNGVVLFKKFDDKKSVFEG-ELNEENLKKFPAQVQSLPLIVDFNHESASKIFGGSIKSHLLFFVSREGGHIEKYVDPLKEIAKKYRDDILFVIISSDEE
Celegans-PDI.am       LKGEGIVLFKKFDDGRVAFDEKLT-QDGLKTWIQANRLALVSEFTQETASVIFGGEIKSHNLLFVSKESSEFAKLEQEFKNAAKQFKGKVLFVYINTDVE
                             * *    .                                   **     .

310       320       330       340       350       360       370       380       390       400
Ct-PDI.ami            ENGRITEFFGLKDDEIPAVRLIQLAEDMSKYKPESSDLETATIKKFVQDFLDGKLKPHLMSEDVPGDWDAKPVKVLVGKNFKEVAMDKSKAVFVEFYAPW
Silkworm-PDI.am       EHQRILEFFGMKKDEVPSARLIALEQDMAKYKPSSNELSPNAIEEFVQSFFDGTLKQHLLSEDLPADWAAKPVKVLVAANFDEVVFDTTKVLVEFYAPW
SeaUrchin-PDI.a       SNSRILEYFGLGDEEVPTVRLITLDGDMKKYKPTVPELTTESLSQFVIDFKDGKLKPHLMSESVPEDWNANPVTILVGENFAEVALDPTKDVLVEFYAPW
Rat-PDI.ami           DNQRILEFFGLKKEECPAVRLITLEEEMTKYKPESDELTAEKITQFCHHFLEGKIKPHLKSDELIAEKITQFCHHFLEGKIKPHLMSQELPEDWDKQPVKVLVGKNFEEVAFDEKKNVFVEFYAPW
Human-PDI.ami         DNQRILEFFGLKKEECPAVRLITLEEEMTKYKPESEELTAERITEFCHRPLEGKIKPHLMSQELPEDWDKQPVKVLVGKNFEDVAFDEKKNVFVEFYAPW
Fly-PDI.ami           DHTRIFEFFGMNKEEVPTIRLIKLEEDMAKYKPESDDLSAETIRAFLKKFLDGKLKPHLKSQELPEDWDKNPVKVLVSSNFESVALDKSKSVLVEFYAPW
Celegans-PDI.am       ENARIMEPFGLKKDELPAIRLRLISSLEEDMTKFKPDFEEITTENISKFTQNYLDGSVKPHLMSEDIPEDWDKNPVKILVGKNFEQVARDNTKNVLVEFYAPW
                     *    * * . ... . * .  .     ..* *           .    **       *         * *  *

410       420       430       440       450       460       470       480       490       500
Ct-PDI.ami            CGHCKQLAPIWDELGEKYKDSKDIVVAKMDATANEIEEVKVQSSFPTLKYFPKDSE--EAVDYNGERTLDAFVKFLESGGTEGAGVQE---DEEBE--BED
Silkworm-PDI.am       CGHCKQLVPIYDKLGEHFENDDDVIIAKIDATANELEHTKITSFSTIKLYSK-DNQ--VHDYNGERTLAGLTKFVETDGEGAEPVPS-----VTE
SeaUrchin-PDI.a       CGHCKQLAPIYEELGEHFKEREDVVIAKVDSTKNEVEDAVVRSFPTLKFWKKGEN--EMVDYSGDRTLEAMIQFVESGGEIIAEVDD----EDME-EDEE
Rat-PDI.ami           CGHCKQLAPIWDKLGETYKDHENIVIAKMDSTANEVEAVKVHSFPTLKFFPASAD-RTVIDYNGERTLDGFKKFLESGGQDGAGDND-DLDLEEALEPDM
Human-PDI.ami         CGHCKQLAPIWDKLGETYKDHENIVIAKMDSTANEVEAVKVHSFPTLKFFPASAD-RTVIDYNGERTLDGFKKFLESGGQDGAGDDDLEDLEBAEEPDM
Fly-PDI.ami           CGHCKQLAPIYDQLAEKYKDNEDIVIAKMDSTANELESIKISSFFTIKYFRKEDNK--VIDFNLDRTLDDFVKFLDANGEVADSEP--------VEE
Celegans-PDI.am       CGHCKQLAPTWDKLGEKFADDESIVIAKMDSTLNEVEDKIQSFPTIKFFFAGSN--KVVDYTGDRTITEGFTKFLETNGKEGAGASE----EEKAEEEAD
                     *******                                                    .*                .

510
Ct-PDI.ami            EEGDDEDLPRDELN     SEQ ID NO:2
Silkworm-PDI.am       FEREEEDVPAKQEL     SEQ ID NO:9
SeaUrchin-PDI.a       MDEGAEDQAKDEL      SEQ ID NO:10
Rat-PDI.ami           EEDDDQKAVKDEL      SEQ ID NO:11
Human-PDI.ami         EEDDDDQKAVKDEL     SEQ ID NO:12
Fly-PDI.ami           TEEEEEEAPKKDEL     SEQ ID NO:13
Celegans-PDI.am       EEGHTEL            SEQ ID NO:14
                     ********
```

FIG. 3

Conus PDI Alignment

```
                         10         20         30         40         50         60         70         80         90        100
PDI-tex3.ami    MKFSSCLVLTLLVFVSAEDVKQEEGVYYLTEKNFDAFISDNEFVLIVEFYAPWCGHCKALAPEYAKAATTLEEEKSNIKLGKVDATVEVNLATKFEVRGYP
PDI-tex2.ami    MKFPSCLVLTLLVFVSAEDVKQEEGVYYLTEKNFGAFISDNEFVLIVEFYAPWCGHCKALAPEYAKAATTLEEEKSNIKLGKVDATVEVNLATKFEVRGYP
PDI-tex1.ami    MKFSSCLVLTLLVFVSAEDVKREEGVYYLTEKNFDAFITDNEFVLIVEFYAPWCGHCKALAPEYAKAATTLEEEKSNIKLGKVDATVEVNLATKFEVRGYP
Ct-PDI.ami      MKFSSCLVLTLLVFVSAEDVEQEENVHVLTKKNFDSFITDNEFVLIVEFYAPWCGHCKALAPEYAKAATTLENEKSNIKLAKVDATVEGDLASKFDVRGYP
                *** ******* *********   **.* *** ***.***.***********************************.***********.*   ** ****

110        120        130        140        150        160        170        180        190        200
PDI-tex3.ami    TIKFFHKEMPAGSPADYSGGRQAPDIVGWLKKKTGPPAKELKAKDEVKTFVEKDEVVXGFFKDQESTGALAFKKAAAGIDDIPFAITSEDHVFKEYKMD
PDI-tex2.ami    TIKFFHKEMPAGSPADYSGGRQAPDIVGWLKKKTGPPAKELKAKDEVKTFVEKDEVVIGFFKDQESTGALAFKKAAAGIDDIPFAITSEDHVFKEYKMD
PDI-tex1.ami    TIKFFHKEMPAGSPADYSGGRQAPDIVGWLKKKTGPPAKELKEKDEVKAFVEKDEVVIGFFKDQESTGALAFKKAAAGIDDIPFAITSEDHVFKEYKMD
Ct-PDI.ami      TIKFFRKEKPDG-PADYSGGRQAKDIVDWLKKKTGPPAKELKEKDEVKDFVEKDEVVIGFFKDQESTGALAFKKAAAGIDDIPFAITSEDHVFKEYKMD
                *****:** * * *********:***.***********::***** **********:***************************************

210        220        230        240        250        260        270        280        290        300
PDI-tex3.ami    KDGIVLLKKFDEGRNDFEGNLEEEEAIVKHVRENQLPLVVEFTQESAQKIFGGEVKNHILLFLKKEGGEDTIEKFRGAAEDFKGKVLFIYLDTDNEENGR
PDI-tex2.ami    KDGIVLLKKFDEGRNDFEGNLEEEEAIVKHVRENQLPLVVEFTQESAQKIFGGEVKNHILLFLKKEGGEDTIEKFRGAAEDFKGKVLFIYLDTDNEENGR
PDI-tex1.ami    KDGIVLLKKFDEGRNDFEGNLEEEEAIVKHVRENQLPLVVEFTQESAQKIFGGEVKNHILLFLKKDGGEDTIEKFRGAAEDFKGKVLFIYLDTDNEENGR
Ct-PDI.ami      KDGIVLLKKFDEGRNDFEGNLEEEEAIVKHVRENQLPLVVEFTQESAQKIFGGEVKNHILLFLKKEGGEDTIEKFRSAAEDFKGKVLFIYLDTDNEENGR
                ***************************************************************:***********.*******************

310        320        330        340        350        360        370        380        390        400
PDI-tex3.ami    ITEFFGLKDDEIPAVRLIQLAEDMSKYKPESSDLETATIKKFVQDFLDGKLKPHLMSEDVPGDWDAKPVKVLVGKNFKEVAMDKSKAVFVEFYAPWCGHC
PDI-tex2.ami    ITEFFGLKDDEIPAVRLIQLAEDMSKYKPESSDLETATIKKFVQDFLDGKLKPHLMSEDVPGDWDAKPVKVLVGKNFKEVAMDKSKAVFVEFYAPWCGHC
PDI-tex1.ami    ITEFFGLKDDEIPAVRLIQLAEDMSKYKPESSDLETATIKKFVQDFLDGKLKPHLMSEDVPGDWDAKPVKVLVGKNFKEVAMDKSKAVFVEFYAPWCGHC
Ct-PDI.ami      ITEFFGLKDDEIPAVRLIQLAEDMSKYKPESSDLETATIKKFVQDFLDGKLKPHLMSEDVPGDWDAKPVKVLVGKNFKEVAMDKSKAVFVEFYAPWCGHC
                ****************************************************************************************************

410        420        430        440        450        460        470        480        490        500
PDI-tex3.ami    KQLAPIWDELGEKYKDSKDIVVAKMDATANEIEEVKVQSFPTLKYFPKDSDEAVDYNGERTLDAFVKFLESGGTEGAGVQEDEEEEEDEEGDDEDLPRD
PDI-tex2.ami    KQLAPIWDELGEKYKDSKDIVVAKMDATANEIEEVKVQSFPTLKYFPKDSDEAVDYNGERTLDAFVKFLESGGTEGAGVQEDEEEEEDEEGDDEDLPRD
PDI-tex1.ami    KQLAPIWDELGEKYKDSKDIVVAKMDATANEIEEVKVQSFPTLKYFPKDSEEAVDYNGERTLDAFVKFLESGGTEGAGVQEDEEEEEDEEGDDEDLPRD
Ct-PDI.ami      KQLAPIWDELGEKYKDSKDIVVAKMDATANEIEEVKVQSFPTLKYFPKDSEEAVDYNGERTLDAFVKFLESGGTEGAGVQEDEEEEEDEEGDDEDLPRD
                *************************************************.**********************************************

PDI-tex3.ami    ELN    SEQ ID NO:8
PDI-tex2.ami    ELN    SEQ ID NO:6
PDI-tex1.ami    ELN    SEQ ID NO:4
Ct-PDI.ami      ELN    SEQ ID NO:2
                ***
```

55 kDa → conotoxins folding time (minutes)

FIG. 9
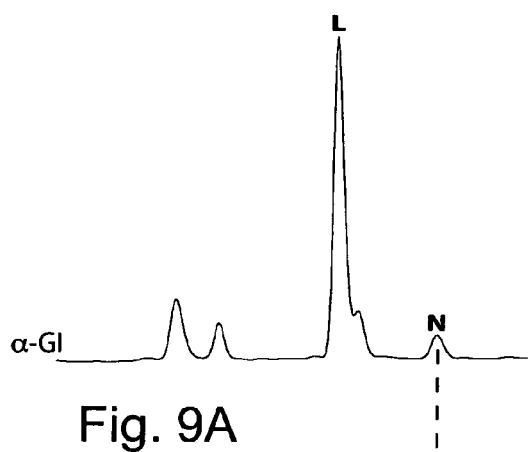
Fig. 9A
Fig. 9B
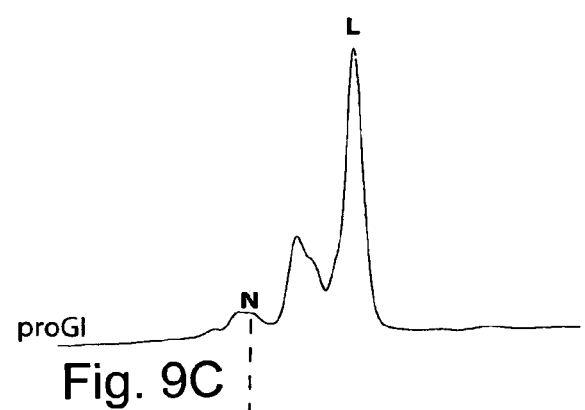
Fig. 9C
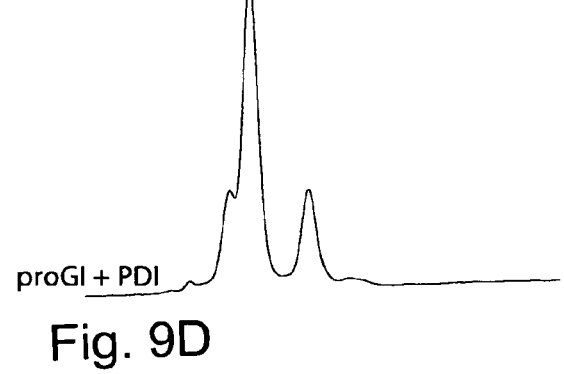
Fig. 9D ~1.6 Kb

NUCLEIC ACID SEQUENCES ENCODING *CONUS* PROTEIN DISULFIDE ISOMERASE

CROSS-REFERENCE TO RELATED APPLICATIONS

This application is a continuation of application Ser. No. 10/789,450, filed Feb. 27, 2004, now abandoned. In addition, this application claims the benefit of U.S. Provisional Application No. 60/453,723, filed Feb. 28, 2003, herein incorporated by reference in its entirety.

STATEMENT REGARDING FEDERALLY SPONSORED RESEARCH OR DEVELOPMENT

This invention was made with Government support under Grant No. PO1 GM48677 awarded by the National Institute of General Medical Sciences, National Institutes of Health, Bethesda, Md. The United States Government may have certain rights in the invention.

STATEMENT ACCORDING TO 37 C.F.R. § 1.52(e)(5)—SEQUENCE LISTING SUBMITTED ON COMPACT DISC

Pursuant to 37 C.F.R. § 1.52(e)(1)(iii), a compact disc containing an electronic version of the Sequence Listing has been submitted concomitant with this application, the contents of which are hereby incorporated by reference. A second compact disc is submitted and is an identical copy of the first compact disc. The discs are labeled "copy 1" and "copy 2," respectively, and each disc contains one file entitled "Sequence Listing.ST25" which is 79 KB and created on Feb. 27, 2004:

TECHNICAL FIELD

The invention relates generally to biotechnology and, more specifically, to protein disulfide isomerases from *Conus* snails, nucleic acid sequences encoding the *Conus* protein disulfide isomerases and to methods for using the nucleic acid or protein sequences for folding disulfide-containing proteins.

BACKGROUND OF THE INVENTION

*Conus* is a genus of predatory marine gastropods (snails) which envenomate their prey. Venomous cone snails use a highly developed injection apparatus to deliver their cocktail of toxic conotoxins into their prey. In fish-eating species such as *Conus magus*, the cone detects the presence of the fish using chemosensors in its siphon and, when close enough, extends its proboscis and impales the fish with a hollow harpoon-like tooth and injects the venom into the fish. This injection immobilizes the fish and enables the cone snail to wind it into its mouth via the proboscis. For general information on *Conus* and their venom, see Coleman, N. (2$^{nd}$ ed., 1992. Ure Smith Press, Sydney, Australia (ISBN 0 7254 0885 5)).

Prey capture is accomplished through a sophisticated arsenal of peptides which target specific ion channel and receptor subtypes. Each *Conus* specie's venom appears to contain a unique set of 50–200 peptides. The composition of the venom differs greatly between species and between individual snails within each species, each optimally evolved to paralyze its prey. The active components of the venom are small peptide toxins, typically 12–30 amino acid residues in length, and are typically highly constrained peptides due to their high density of disulfide bonds.

The venoms consist of a large number of different peptide components that, when separated, exhibit a range of biological activities. When injected into mice, they elicit a range of physiological responses from shaking to depression. The paralytic components of the venom that have been the focus of recent investigation are the α-, ω- and μ-conotoxins. All of these conotoxins are believed to act by preventing neuronal communication, but each targets a different aspect of the process to achieve this action. Each venom component has a very specific pharmacologic target. For example, a linkage has been established between α-, αA- and ψ-conotoxins and the nicotinic ligand-gated ion channel; ω-conotoxins and the voltage-gated calcium channel; μ-conotoxins and the voltage-gated sodium channel; δ-conotoxins and the voltage-gated sodium channel; κ-conotoxins and the voltage-gated potassium channel; conantokins and conodynes and the ligand-gated glutamate (NMDA) channel. (Olivera et al., 1985; Olivera et al., 1990.) The pharmacological specificity of the conotoxins makes them attractive for drug development for a variety of therapeutic applications, including neurological and cardiovascular disorders.

A characteristic structural feature of conotoxins is a large number of posttranslational modifications, in particular disulfide bridges. The primary function of disulfide bonds appears to be stabilization of the structure. Conotoxins are grouped into families, based upon the number and arrangement of disulfide bonds. For example, two disulfide-containing α-conotoxins contain the cysteine pattern, CC—C—C, with disulfides between the 1$^{st}$ and 3$^{rd}$, 2$^{nd}$ and 4$^{th}$ cysteines. Three disulfide-containing ω- and δ-conotoxins share the native cysteine pattern, C—C—CC—C—C, whereas μ-conotoxins share the common cysteine pattern, CC—C—C—CC. For native ω-, δ-conotoxins, the 1$^{st}$ and 4$^{th}$, 2$^{nd}$ and 5$^{th}$ and 3$^{rd}$ and 6$^{th}$ cysteines are connected; for native μ-conotoxins, the 1$^{st}$ and 4$^{th}$, 2$^{nd}$ and 5$^{th}$ and 3$^{rd}$ and 6$^{th}$ cysteines are connected by disulfide bonds. The correct pairing of disulfides in the native conotoxins is a prerequisite for maintaining their biological activity. The disulfide bridges are formed in a process of oxidative pairing of the cysteine residues.

Conotoxins are naturally synthesized as precursors in cells (Woodward et al., 1990; Colledge et al., 1992). For all conotoxins, the precursors share a similar organization: an N-terminal signal sequence, a propeptide region and a C-terminal cysteine-rich toxin region. Each family of conotoxins is characterized by a highly conserved signal sequence, a moderately conserved propeptide region and an almost random toxin region that contains a conserved cysteine framework.

Propeptides have been shown in many biological systems to assist in the oxidative folding of polypeptides. Examples of those studies are summarized in Table 1. Folding kinetics and yields can be significantly improved when oxidation of cysteine-rich peptides is carried out using the propeptide. In the case of proguanylin, a peptide containing two disulfide bridges, folding yields improved from 7%, using mature peptide, to 95%, using the propeptide (Schulz et al., 1999). Similar studies on the guanylyl cyclase-activating peptide, GCAP-II, showed that two amino acids in the N-terminal fragment of the propeptide were directly involved in the enhancement of peptide folding (Hidaka et al., 2000). For oxidative folding of bovine pancreatic trypsin inhibitor (BPTI), the propeptide substantially increased the folding yields and the kinetics of folding through an additional N-terminal cysteine residue present in the propeptide fragment. It thus appears that propeptides can facilitate oxidative folding of polypeptides.

TABLE 1

Summary of intramolecular and intermolecular factors influencing the oxidative folding of polypeptides.

| Factors | Examples of polypeptides |
|---|---|
| Propeptide-assisted oxidative folding | Macrophage inhibitory cytokine-1 MIC-1 (Fairlie et al., 2001), Nerve growth factor hNGF (Rattenholl et al., 2001), Prouroguanylin, GCAP (Hidaka et al., 1998; Schulz et al., 1999; Hidaka et al., 2000), pancreatic trypsin inhibitor BPTI (Weissman and Kim, 1992) |
| Chaperones Hsp70/hsp40 Calreticulin/calnexin | Hsp70 - binding to early folding intermediates (BiP/GRP78, GRP170), Hsp40 - cochaperones regulating Hsp70 (Sec63p, DnaJ), Hsp90 - general chaperones (GRP94), Hsp25 (small heat-shock proteins with single Cys residues), Lectins - quality control of folding (calnexin, calreticulin) immunophilins - isomerization of prolines (cyclophilin, FKPB13) (Gething, 1997; 1999) |
| Disulfide isomerases and other oxido-reductases | PDI (Freedman et al., 1994; Gilbert, 1997) Erp72, CaPB1, CaPB2 (Rupp et al., 1994) Ero1p (Tu et al., 2000) Erv2 (Servier et al., 2001) |

However, not all propeptides have been shown to increase the folding yields and/or the kinetics of folding. For example, ω-conotoxin MVIIA and insulin-like growth factor (IGF) are two reported examples where a propeptide did not have a direct effect on oxidative folding. Studies by Price-Carter and Goldenberg (Price-Carter et al., 1996b) suggested that the propeptide sequence neither increased folding yields nor enhanced the kinetics of folding of ω-MVIIA. While, mature ω-MVIIA folds with relatively high yields, using the propeptide of IGF did not facilitate folding. In the case of IGF, the propeptide, likewise, did not facilitate folding.

Taken together, these studies demonstrate examples where the propeptide is very important in determining folding properties of polypeptides, as well as examples where a propeptide is not directly involved in the folding mechanism. In addition to the possible role played by propeptides, a number of other molecules are known to regulate the folding pathway of peptides in order to increase the kinetics and yields of properly folded forms.

Molecular chaperones comprise a large number of proteins that are specialized as folding assistants. Their general function is to prevent the aggregation and precipitation of nascent polypeptides and folding intermediates. These chaperones are localized in the cytoplasm and in the endoplasmic reticulum ("ER") and bind to different folding species with relatively low specificity. The ER is the main protein-folding compartment where a majority of chaperones are involved in folding, quality control and translocation of polypeptides. Since the ER is also the only compartment where oxidative folding occurs, chaperones in the ER play a prominent role in the oxidative folding of proteins. For example, BiP, a member of the Hsp70 chaperone family, was recently shown to cooperate with protein disulfide isomerase in the oxidative folding of antibodies (Mayer et al., 2000). Some examples of molecular chaperones are summarized in Table 1.

The oxidative folding of polypeptides in vivo is catalyzed by protein disulfide isomerase (PDI), which can act as both a folding catalyst and as a molecular chaperone. The activity of this enzyme was originally discovered in rat liver, but since then it has been documented in a variety of different species. PDI belongs to a group of protein-thiol oxidoreductase enzymes, which contain thioredoxin domains. A typical PDI molecule consists of two similar thioredoxin-like domains. These domains contain the Cys-Gly-His-Cys (CGHC) (SEQ ID NO:19) redox active site. The C-terminal region of PDI has an additional domain with an ER retention signal sequence. However, there are many different classes of PDIs which are distinguished based upon their thioredoxin domain arrangement and composition as summarized in (McArthur, A. G. et al., Mol. Biol. Evol. 18(8) 1455-63, 2001).

PDI catalyzes protein thiol-disulfide exchange reactions using the thioredoxin CGHC (SEQ ID NO:19) redox active site. The enzyme contains two CGHC (SEQ ID NO:19) motifs, a low affinity peptide binding site and a KDEL (SEQ ID NO:20) endoplasmic reticulum retrieval signal. PDI is also characterized by a large number of low affinity/high capacity calcium binding sites. The oxidoreductase activity of PDI is mediated by the pair of Cys residues in the active site. These Cys residues can be easily reduced to thiols, or oxidized to a disulfide, depending on the redox potential and relative concentration of substrates and products in the ER. Moreover, PDI was also shown to be sufficient for promoting oxidative folding, even in the absence of glutathione, a molecule primarily responsible for maintaining the oxidative environment of the ER (Tu et al., 2000). In addition to its catalytic role in oxidative folding, PDI can also function as a molecular chaperone. PDI was found to facilitate folding of proteins lacking disulfides, such as rhodanase or glyceraldehyde-3-phosphate dehydrogenase. This dual function of PDI was recently characterized during the oxidative folding of proinsulin (Winter et al., 2002). In the proinsulin study, PDI increased the rate of oxidative folding and prevented proinsulin aggregation.

Since PDI has been found in bacteria, fungi, plants, invertebrate and vertebrate animals, we sought to determine if *Conus* snails have also utilized this enzyme to produce conotoxins. Because *Conus* species produce a large number of disulfide-rich proteins in their venom, a need exists in the art to identify the nucleic acid sequences encoding *Conus* protein disulfide isomerases, to identify the sequences of *Conus* protein disulfide isomerases, and to use the nucleic acids or proteins in the folding of disulfide-containing proteins.

SUMMARY OF THE INVENTION

The invention relates to protein disulfide isomerases from *Conus* snails, to the nucleic acid sequences encoding the *Conus* protein disulfide isomerases, and to a method for using the nucleic acid or protein sequences for folding of disulfide-containing proteins.

Thus, one aspect of the invention relates to the amino acid sequence of a *C. textile* protein disulfide isomerase or PDI with at least 95% identity with the amino acid sequence set forth in SEQ ID NO:2 which has protein disulfide isomerase activity. The amino acid sequence of *C. textile* protein disulfide isomerases are set forth in SEQ ID NO:2, SEQ ID NO:4, SEQ ID NO:6 and SEQ ID NO:8.

In another aspect, the invention features a substantially pure preparation of a *C. textile* protein disulfide isomerase. In preferred embodiments, the protein disulfide isomerase includes an amino acid sequence which is at least 57%, preferably at least 65%, preferably at least 75%, preferably at least 85%, and more preferably at least 90% identical to the amino acid sequence of SEQ ID NO:2, SEQ ID NO:4, SEQ ID NO:6 or SEQ ID NO:8, or any combination thereof.

Another aspect of the invention relates to a nucleic acid encoding a *C. textile* protein disulfide isomerase or a nucleic acid encoding a protein disulfide isomerase having at least 85%, preferably at least 90%, and more preferably at least 95% identity with the amino acid sequence set forth in SEQ ID NO:2, SEQ ID NO:4, SEQ ID NO:6 or SEQ ID NO:8. A preferred nucleotide sequence of the nucleic acid is set forth in SEQ ID NO:1, SEQ ID NO:3, SEQ ID NO:5, or SEQ ID NO:7, or any combination thereof.

Another aspect of the invention relates to a recombinant or isolated nucleic acid having at least 50%, preferably at least 65%, preferably at least 85%, and more preferably at least 95% identity with the sequence set forth in SEQ ID NO:1, SEQ ID NO:3, SEQ ID NO:5 or SEQ ID NO:7.

Another aspect of the invention relates to vectors containing the protein disulfide isomerase encoding nucleic acid. The isolated nucleic acid encoding a protein disulfide isomerase may be included in a vector, such as a vector that is capable of directing the expression of the protein encoded by the nucleic acid in a vector-containing cell. The isolated nucleic acid in the vector can be operatively linked to a promoter, for example, a promoter that is capable of overexpressing the protein disulfide isomerase, or that is capable of expressing the protein disulfide isomerase in a conditional manner. The vector may include one or more of the following: a selectable marker, an origin of replication, or other sequences known in the art. The isolated nucleic acid encoding a protein disulfide isomerase, or a vector including this nucleic acid, may be contained in a cell, such as a bacterial, mammalian, or yeast cell.

Another aspect of the invention relates to host cells containing a vector capable of directing expression of a protein disulfide isomerase encoding a nucleic acid. Another aspect of the invention relates to host cells containing an expression cassette with the protein disulfide isomerase encoding a nucleic acid sequence and an expression cassette with a nucleic acid sequence encoding a disulfide-containing protein which is to be expressed and folded. Such disulfide-containing proteins include conotoxins.

In another aspect, the invention relates to a method of increasing disulfide bond formation in a protein (for example, a conotoxin, involving expressing the protein in a host cell that also expresses an isolated nucleic acid that encodes a protein disulfide-isomerase. In another embodiment, the protein disulfide-isomerase polypeptide is derived from a *Conus* species. In another embodiment, the protein is a conotoxin.

Another aspect of the invention relates to the use of a protein disulfide isomerase for the folding of disulfide-rich proteins, where the PDI increases the rate or yield of properly folded disulfide-rich proteins. Such use includes in vitro oxidative folding reactions.

Another aspect of the invention relates to a substantially pure antibody, such as a monoclonal or polyclonal antibody, that specifically recognizes and binds a protein disulfide-isomerase polypeptide derived from a *Conus* species, for example, SEQ ID NO:2, SEQ ID NO:4, SEQ ID NO:6, or SEQ ID NO:8, or any combination thereof.

BRIEF DESCRIPTION OF THE DRAWINGS

FIG. 2 is an alignment of PDIs from *Conus textile* (Ct-PDI) (SEQ ID NO:2), silkworm (SEQ ID NO:9), sea urchin (SEQ ID NO:10), rat (SEQ ID NO:11), human (SEQ ID NO:12), *Drosophila* (Fly-PDI) (SEQ ID NO:13), and *C. elegans* (SEQ ID NO:14). This figure indicates the nonvariant amino acids by the presence of a * under that amino acid position.

FIG. 3 is an alignment of the *Conus textile* Protein Disulfide Isomerase (Ct-PDI) and three isoforms. The PDI isolated from *Conus textile* (SEQ ID NO:2) is aligned with the three isoforms, tex1 (SEQ ID NO:4), tex2 (SEQ ID NO:6) and tex3 (SEQ ID NO:8), isolated from the same species. Identical amino acids are indicated by a "*" under the amino acid position.

FIGS. 4A and 4B are an electrophoretic analysis of proteins from a *Conus textile* venom duct. FIG. 4A) The venom duct was dissected from *C. textile* and immediately divided into four equal portions. The proximal venom bulb is a muscle and does not directly participate in a production of conotoxins. FIG. 4B) The 55 kDa PDI is one of the predominant proteins from the snail's venom duct (lanes 1–4), as was confirmed by the Edman's sequencing. Lane 5 is the reference—bovine PDI.

FIG. 7A shows the kinetics for folding of αGI in the absence of PDI; FIG. 7B shows the kinetics for folding of αGI in the presence of bovine PDI; FIG. 7C shows the kinetics for folding of proGI in the absence of PDI; and FIG. 7D shows the kinetics for folding of proGI in the presence of bovine PDI. The normative form is represented by open circles, the linear form is represented by open boxes and the native form is represented by filled circles.

FIGS. 9A–9D show chromatographs of the folding species. FIG. 9A is a chromatograph of αGI in the absence of PDI. FIG. 9B is a chromatograph of αGI in the presence of bovine PDI. FIG. 9C is proGI in the absence of PDI. FIG. 9D is a chromatograph of proGI in the presence of bovine PDI. The chromatographs represent the folding species present in the folding reaction after ten and 15 minutes, FIGS. 9B and 9D and 9A and 9C, respectively. "L" represents the linear form and the native form is indicated by an "N" above the appropriate peak.

DETAILED DESCRIPTION OF THE INVENTION

Figure 1:
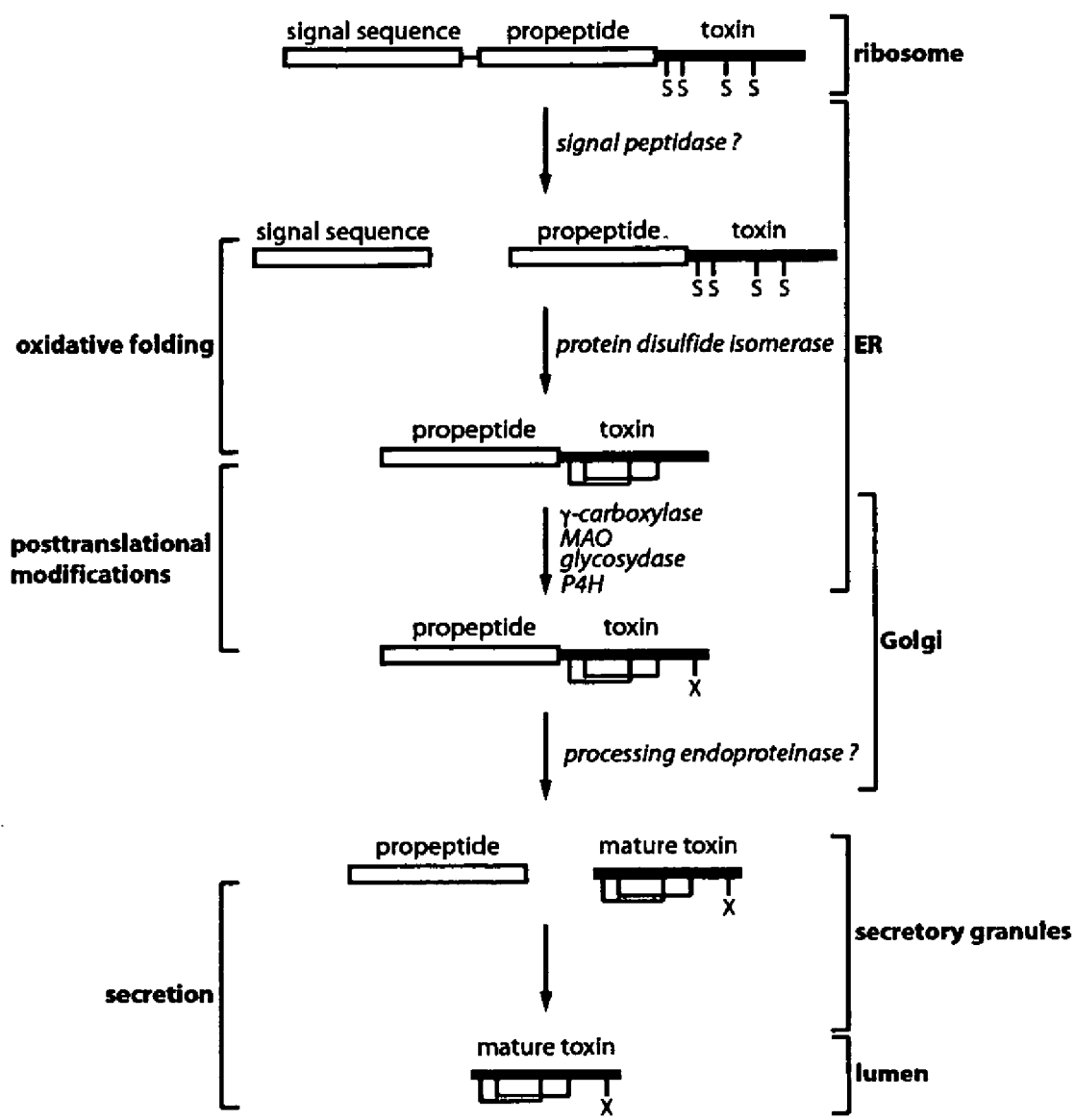
FIG. 1 is a schematic representation of the general biosynthetic pathway of conotoxins. Abbreviations: S, cysteine in the reduced form; ER, endoplasmic reticulum; MAO, monoamine oxidase; P4H, prolyl 4-hydroxylase; X, other posttranslational modification.

As used herein, the terms "conotoxin" and "conotoxin polypeptide" comprise conantokin peptides, conantokin peptide derivatives, conotoxin peptides and conotoxin peptide derivatives. Conotoxins are typically derived from the venom of *Conus* snails and may include one or more amino acid substitutions, deletions and/or additons. These peptides may be referred to in the literature as conotoxins, conantokins or conopeptides. The conotoxin may be produced by methods, such as in vitro translation, in vitro transcription and translation, recombinant expression systems, and chemical synthesis.

As used herein, the phrase "disulfide-rich peptide" contemplates a polypeptide or protein having two or more possible disulfide bonds. Examples of disulfide-rich peptides include, but are not limited to, spider toxins, conotoxins, antibodies and fragments thereof, such as fragments of conotoxins and Fab fragments. Disulfide linkages can be formed between cysteine residues of the same or different polypeptides.

As used herein, "substantially pure" means a preparation which is at least 60% by weight (dry weight) of the compound of interest, for example, a protein disulfide isomerase or a disulfide-rich peptide. Preferably, the preparation is at least 75%, more preferably at least 90%, and most preferably at least 99% by weight of the compound of interest. Purity can be measured by any appropriate method, for example, column chromatography, polyacrylamide gel electrophoresis, or HPLC analysis.

As used herein, an "isolated nucleic acid" means a nucleic acid that is not immediately contiguous with both of the coding sequences with which it is immediately contiguous (one on the 5' end and one on the 3' end) in the naturally occurring genome of the organism from which it is derived. The term therefore includes, for example, a recombinant nucleic acid which is incorporated into a vector; into an autonomously replicating plasmid or virus; or into the genomic DNA of a prokaryote or eukaryote, or which exists as a separate molecule (for example, a cDNA or a genomic DNA fragment produced by PCR or restriction endonuclease treatment) independent of other sequences. It also includes a recombinant nucleic acid which is part of a hybrid gene encoding additional polypeptide sequences.

As used herein, a "substantially identical" polypeptide sequence means an amino acid sequence which differs from a reference sequence only by conservative amino acid substitutions, for example, substitution of one amino acid for another of the same class (for example, valine for glycine, arginine for lysine, etc.) or by one or more nonconservative substitutions, deletions, or insertions located at positions of the amino acid sequence which do not destroy the function of the polypeptide (assayed, for example, as described herein). Preferably, such a sequence is at least 73%, more preferably at least 85%, and most preferably at least 95% substantially identical at the amino acid level to the sequence used for comparison. The invention encompasses polypeptide sequences being 73–99% substantially identical to the amino acid sequences set forth is SEQ ID NO:2, SEQ ID NO:4, SEQ ID NO:6 and SEQ ID NO:8, or any combination thereof.

As used herein, a "substantially identical" nucleic acid means a nucleic acid sequence which encodes a polypeptide differing only by conservative amino acid substitutions, for example, substitution of one amino acid for another of the same class (for example, valine for glycine, arginine for lysine, etc.) or by one or more nonconservative substitutions, deletions, or insertions located at positions of the amino acid sequence which do not destroy the function of the polypeptide (assayed, for example, as described herein). Preferably, the encoded sequence is at least 75%, more preferably at least 85%, and most preferably at least 95% identical at the amino acid level to the sequence of comparison. If nucleic acid sequences are directly compared, a "substantially identical" nucleic acid sequence is one which is at least 85%, more preferably at least 90%, and most preferably at least 95% identical to the sequence of comparison. The invention encompasses polynucleotide sequences being 60–99% substantially identical to the nucleic acid sequences set forth is SEQ ID NO:1, SEQ ID NO:3, SEQ ID NO:5 and SEQ ID NO:7, or any combination thereof. The length of nucleic acid sequence comparison will generally be at least 50 nucleotides, preferably at least 60 nucleotides, more preferably at least 75 nucleotides, and most preferably at least 100 nucleotides. Sequence identity is typically measured using sequence analysis software (for example, Sequence Analysis Software Package of the Genetics Computer Group, University of Wisconsin Biotechnology Center, 1710 University Avenue, Madison, Wis. 53705).

As used herein, "positioned for expression" means that the nucleic acid molecule is operably linked to a sequence which directs transcription and translation of the nucleic acid molecule.

As used herein, "purified antibody" means an antibody which is at least 60%, by weight, free from the proteins and naturally occurring organic molecules with which it is naturally associated. Preferably, the preparation is at least 75%, more preferably at least 90%, and most preferably at least 99%, by weight, antibody.

As used herein, "specifically binds" means an antibody which recognizes and binds a *Conus* protein disulfide isomerase, but which does not substantially recognize and bind other molecules in a sample (for example, a biological sample). An antibody which "specifically binds" such a polypeptide is sufficient to detect protein product in such a biological sample using one or more of the standard immunological techniques available to those in the art (for example, Western blotting or immunoprecipitation).

As used herein, "peptide," "polypeptide" and "protein" include polymers of two or more amino acids of any length. No distinction, based on length, is intended between a peptide, a polypeptide or a protein.

As used herein, "protein disulfide isomerase activity" includes fragments of a protein disulfide isomerase which retain protein disulfide isomerase activity as assayed using methods known in the art or disclosed herein. Fragments of a protein disulfide isomerase, which retain protein disulfide isomerase activity, include N-terminal truncations, C-terminal truncations, amino acid substitutions, deletions and addition of amino acids (either internally or at either terminus of the protein).

Yeast cells have been used for expression of disulfide-rich polypeptides and co-expression of PDI has resulted in improved recombinant expression of properly folded disulfide-rich peptides (Kowalski et al., 1998; Shusta et al., 1998). The invention provides an important advance in this field of technology. For example, the identification of the *Conus* protein disulfide isomerase provides a simple and inexpensive means to increase the production of commercially important disulfide bond-containing proteins. *Conus* PDI provides a useful folding catalyst for production of properly folded conotoxins, for example, when produced in a recombinant system. Also, a *Conus* PDI is useful as a folding catalyst of conotoxins that are synthesized chemically and folded in vitro. Because the protein disulfide isomerase may be recombinantly expressed in combination with a commercial protein of interest or may be used as an isolated and purified reagent, the invention enables the enhancement of disulfide bond formation during in vivo commercial protein production or at subsequent in vitro purification steps, or both. Moreover, to further maximize disulfide bond formation, *Conus* protein disulfide isomerase proteins may be used in conjunction with other disulfide bond-forming enzymes, for example, Erolp, or cell extracts, for example, in vitro translation systems such as rabbit reticulocyte lysates or wheat germ systems. Proper formation of disulfide bonds results in the production of batches of recombinant proteins exhibiting higher yields of properly folded products; this maximizes protein activity and minimizes the presence of inactive species and/or species which may be capable of triggering immunological side effects.

The invention relates to protein disulfide isomerases from *Conus* snails, to nucleic acid sequences encoding the *Conus* protein disulfide isomerases and to a method for using the nucleic acid or protein sequences for folding disulfide-containing proteins.

In one aspect, the invention relates to the amino acid sequence of *C. textile* protein disulfide isomerase. The amino acid sequences of *C. textile* protein disulfide isomerases are set forth in SEQ ID NO:2, SEQ ID NO:4, SEQ ID NO:6 or SEQ ID NO:8. In another embodiment, the invention relates to a protein disulfide isomerase that has at least 95% identity with the amino acid sequence set forth in SEQ ID NO:2 and has protein disulfide isomerase activity. In another embodiment, the invention relates to a protein disulfide isomerase that has at least 95% identity with the amino acid sequence set forth in SEQ ID NO:4 and has protein disulfide isomerase activity. In another embodiment, the invention relates to a protein disulfide isomerase that has at least 95% identity with the amino acid sequence set forth in SEQ ID NO:6 and has protein disulfide isomerase activity. In another embodiment, the invention relates to a protein disulfide isomerase that has at least 95% identity with the amino acid sequence set forth in SEQ ID NO:8 and has protein disulfide isomerase activity. Protein disulfide isomerase activity can be assayed as described herein or by methods known in the art.

In another aspect, the invention relates to functional fragments of *Conus* protein disulfide isomerase. The PDI of SEQ ID NO:2 has two thioredoxin domains, amino acids 23–134 and 365–470, and a calsequestrin domain from amino acids 23 to 280. The PDI of the invention includes fragments of the PDI wherein protein disulfide isomerase activity is retained. For example, a peptide having a single thioredoxin domain, wherein the single domain has protein disulfide isomerase activity, is an aspect of the invention. The domain structure may be assayed, for example, using computer programs such as those described in Altschul, et al. (1997), *Nucleic Acids Res.* 25:3389–3402.

In another aspect, the invention relates to vectors containing the nucleic acid encoding a protein disulfide isomerase of the present invention. In one embodiment, the vector is an expression vector.

Those skilled in the field of molecular biology will understand that any of a wide variety of expression systems may be used to provide the recombinant protein. The precise host cell used is not critical to the invention. The host cells produce the protein disulfide isomerase when grown under suitable growth conditions. Suitable host cells include, but are not limited to, a eukaryotic host, such as insect cell lines (for example, HIGH FIVE™ from INVITROGEN™ (BTI-TN-5B1–4), derived from *Trichoplusia ni* egg cell homogenates), Sf9 or Sf21 cells, Lepidopteran insect cells, mammalian cell lines (for example, primary cell cultures or immortalized cell lines, such as COS 1, NIH 3T3, HeLa, 293, CHO and U266), transgenic plants, plant cells, *Drosophila* Schneider2 (S2) cells, Baculovirus Expression Systems, *Saccharomyces, Schizosaccharomyces*, a prokaryotic host, such as *Aspergillus, E. coli, Bacillus* or the like. Such cells are available from a wide range of sources (e.g., the American Type Culture Collection, Rockland, Md.; INVITROGEN™; GIBCO™; see also, e.g., Ausubel et al., supra). The method of transformation or transfection and the choice of expression vehicle (vector) will depend on the host system selected. Transformation and transfection methods are described, e.g., in Ausubel et al., supra; expression vehicles may be chosen from those provided, for example, in Cloning Vectors: A Laboratory Manual (P. H. Pouwels et al., 1985, Supp. 1987) or known in the art.

A conotoxin or protein disulfide isomerase polypeptide is produced in a mammalian system, for example, by a stably transfected mammalian cell line. A number of vectors suitable for stable transfection of mammalian cells are available; methods for constructing such cell lines are also publicly available, e.g., in Ausubel et al., supra. In one example, cDNA encoding the protein disulfide isomerase protein is cloned into an expression vector which includes the dihydrofolate reductase (DHFR) gene. Integration of the plasmid and, therefore, the PDI protein-encoding gene into the host cell chromosome is selected for by inclusion of 0.01–300 µM methotrexate in the cell culture medium (as described in Ausubel et al., supra). This dominant selection may be accomplished in most cell types. Recombinant protein expression may be increased by DHFR-mediated amplification of the transfected gene. Methods for selecting cell lines bearing gene amplifications are described in Ausubel et al., supra; such methods generally involve extended culture in medium containing gradually increasing levels of methotrexate. DHFR-containing expression vectors commonly used for this purpose include pCVSEII-DHFR and pAdD26SV(A) (described in Ausubel et al., supra). Any of the host cells described above or, preferably, a DHFR-deficient CHO cell line (for example, CHO DHFR cells, ATCC Accession No. CRL 9096) are among the host cells preferred for DHFR selection of a stably transfected cell line or DHFR-mediated gene amplification.

In another example, cDNA encoding the protein disulfide isomerase is cloned into a vector or an expression vector which includes a selectable marker gene. Methods for selecting cell lines containing the vector or expression vector are known in the art and described in Ausubel et al., supra.

In another aspect, the invention relates to host cells containing an expression cassette or expression vector with the protein disulfide isomerase encoding a nucleic acid of the invention and an expression cassette with a nucleic acid sequence encoding a disulfide-containing protein which is to be properly folded and expressed. Such proteins include conotoxins.

In another aspect, the invention relates to the use of a protein disulfide isomerase of the invention for the folding of disulfide-rich proteins.

In another aspect, the invention relates to an antibody that selectively binds to a PDI isolated from Conus, for example, an antibody that selectively binds to a region of SEQ ID NO:2, SEQ ID NO:4, SEQ ID NO:6 or SEQ ID NO:8.

In another aspect, the invention relates to nucleic acid derivatives and allelic variations of the nucleic acids and proteins disclosed in SEQ ID NO:1 through SEQ ID NO:8. The invention also relates to fragments of either the nucleic acid or protein which encodes or retains protein disulfide isomerase activity as assayed using methods known in the art or disclosed herein.

In another aspect, the invention relates to a method for increasing protein secretion of overexpressed gene products by enhancing protein disulfide isomerase activity within a cell. In eukaryotic cells, correct folding and assembly of a secreted polypeptide occurs in the endoplasmic reticulum (ER). (FIG. 1 illustrates the typical secretory/folding pathway and maturation process for a conopeptide.) Correct folding is a prerequisite for transport from the ER through the secretory pathway, with misfolded proteins being retained in the ER. Therefore, increased expression of the PDI of the invention is used to reduce the percentage of misfolded proteins and thereby increase secretion of the overexpressed gene product. At least one PDI of the invention is expressed in a host cell which overexpresses a gene product. "Overexpression," as used herein, means a gene product that is expressed at levels greater than normal wild-type endogenous expression for that gene product. Thus, an overexpressed gene product is produced by, for example, introduction of a recombinant expression construct or altering endogenous expression levels, for example, by mutation or induction of transcription.

In another aspect, the invention is used to reconfigure human or animal hair. The compositions of the invention can be used for the treatment or degradation of scleroproteins, especially hair, skin and wool, dehairing and softening hides, treatment and cleaning of fabrics, as additives to detergents, thickening and gelation of food and fodder, strengthening of gluten in bakery or pastry products, and as pharmaceuticals for the alleviation of eye sufferings.

In another aspect, the PDI of the invention, having improved properties for a particular application, can be prepared by a variety of methods based on standard recombinant DNA technology, for example, by using site-directed or random mutagenesis to modify the genes encoding a *Conus* PDI to produce one or more amino acid changes, by inhibiting or otherwise avoiding dimerization of the subunits of PDI to provide PDI monomers, by producing partial monomers of PDI-lacking regions of the amino-terminus or carboxy-terminus of the PDI. Furthermore, the invention includes active truncated forms of the *Conus* PDIs which retain protein disulfide isomerase activity, wherein at least one redox site subunit (CGHC (SEQ ID NO:19)) is retained. For example, the minimal redox sites are located at amino acid positions 53–56 and 401–404 of SEQ ID NO:2.

In another aspect, the invention relates to a nucleic acid encoding an active recombinant protein disulfide isomerase of the invention. The nucleic acid may comprise introns and/or regulatory elements native to the *Conus* PDI. Alternatively, the nucleic acid may comprise introns and/or regulatory elements derived from other organisms or synthetic constructs.

A nucleic acid or fragment thereof has substantial identity with another if, when optimally aligned (with appropriate nucleotide insertions or deletions) with the other nucleic acid (or its complementary strand), there is nucleotide sequence identity in at least about 70% of the nucleotide bases, usually at least about 80%, more usually at least about 85%, and more preferably at least about 90% of the nucleotide bases. A protein or fragment thereof has substantial identity with another if, when optimally aligned, there is an amino acid sequence identity of at least about 70% identity with an entire naturally occurring protein or a portion thereof, usually at least about 80% identity, preferably at least about 85% identity, preferably at least about 90% identity, and more preferably at least about 95–98% identity.

Sequence identity is typically measured using sequence analysis software (for example, Sequence Analysis Software Package of the Genetics Computer Group, University of Wisconsin Biotechnology Center, 1710 University Avenue, Madison, Wis., 53705, or BLAST software available from the National Library of Medicine). Examples of useful software include the programs, PILE-UP™ and PRETTY-BOX™. Such software matches similar sequences by assigning degrees of homology to various substitutions, deletions, substitutions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

"Identity" means the degree of sequence relatedness between two polypeptide or two polynucleotides sequences as determined by the identity of the match between two strings of such sequences, such as the full and complete sequence. Identity can be readily calculated. While there exist a number of methods to measure identity between two polynucleotide or polypeptide sequences, the term "identity" is well known to skilled artisans (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M. Stockton Press, New York, 1991). Methods commonly employed to determine identity between two sequences include, but are not limited to, those disclosed in *Guide to Huge Computers*, Martin J. Bishop, ed., Academic Press, San Diego, 1994, and Carillo, H., and Lipman, D., *SIAM J. Applied Math*, 48:1073 (1988). Preferred methods to determine identity are designed to give the largest match between the two sequences tested. Such methods are codified in computer programs. Preferred computer program methods to determine identity between two sequences include, but are not limited to, GCG (Genetics Computer Group, Madison Wis.) program package (Devereux, J., et al., *Nucleic Acids Research* 12(1), 387 (1984)), BLASTP, BLASTN, FASTA (Altschul et al. (1990); Altschul et al. (1997)). The well-known Smith Waterman algorithm may also be used to determine identity.

As an illustration, by a polynucleotide having a nucleotide sequence having at least, for example, 95% "identity" to a reference nucleotide sequence, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations relative to the reference sequence may occur at the 5 or 3 terminal positions of the reference nucleotide sequence or anywhere between those terminal positions, interspersed either individually among nucleotides in the reference sequence or in one or more contiguous groups within the reference sequence.

Alternatively, substantial homology or (similarity) exists when a nucleic acid or fragment thereof will hybridize to another nucleic acid (or a complementary strand thereof) under selective hybridization conditions. Selectivity of hybridization exists when hybridization which is substantially more selective than total lack of specificity occurs. Typically, selective hybridization will occur when there is at least about 55% homology over a stretch of at least about nine nucleotides, preferably at least about 65%, more preferably at least about 75%, and most preferably at least about 90%. The length of homology comparison, as described, may be over longer stretches and, in certain embodiments, will often be over a stretch of at least about 14 nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, the length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. The stringency conditions are dependent on the length of the nucleic acid and the base composition of the nucleic acid, and can be determined by techniques well known in the art, for example, Ausubel, 1992; Wetmur and Davidson, 1968.

Thus, as herein used, the term "stringent conditions" means hybridization will occur only if there is at least 80%, preferably at least 90%, more preferable at least 95% and most preferably at least 97% identity between the sequences. Such hybridization techniques are well known to those of skill in the art. Stringent hybridization conditions are as defined above or, alternatively, conditions under overnight incubation at 42° C. in a solution comprising: 50% formamide, 5×SSC (150 mM NaCl, 15 mM trisodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65° C.

Hybridization techniques and procedures are well known to those skilled in the art and are described, for example, in Ausubel et al., supra, and *Guide to Molecular Cloning Techniques*, supra. If desired, a combination of different oligonucleotide probes may be used for the screening of the recombinant DNA library. The oligonucleotides are, for example, labeled with $^{32}$P using methods known in the art, and the detectably labeled oligonucleotides are used to probe filter replicas from a recombinant DNA library. Recombinant DNA libraries (for example, *Conus* cDNA libraries) may be prepared according to methods well known in the art, for example, as described in Ausubel et al., supra. Such libraries may be generated using standard techniques.

An alignment of PDIs from *Conus textile* (Ct-PDI) (SEQ ID NO:2), silkworm (SEQ ID NO:9), sea urchin (SEQ ID NO:10), rat (SEQ ID NO:11), human (SEQ ID NO:12), *Drosophila* (Fly-PDI) (SEQ ID NO:13), and *C. elegans* (SEQ ID NO:14) is illustrated in FIG. 2. This figure indicates the nonvariant amino acids by the presence of a * under that amino acid position.

An alignment of four *Conus textile* Protein Disulfide Isomerases of the invention is illustrated in FIG. 3. The four sequences shown correspond to *Conus textile* PDI (SEQ ID NO:2) and three isoforms, tex1 (SEQ ID NO:4), tex2 (SEQ ID NO:6) and tex3 (SEQ ID NO:8). The isolated PDIs from *Conus textile* demonstrate a high degree of sequence identity relative to the interspecies sequence identity.

Large amounts of the nucleic acids of the invention may be produced by (a) replication in a suitable host or transgenic animal or (b) chemical synthesis using techniques well known in the art. Constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. The choice of vector will often depend on the host cell into which it is to be introduced. Thus, the vector may be an autonomously replicating vector, a viral or phage vector, a transposable element, an integrating vector or an extrachromosomal element, such as a minichromosome or an artificial chromosome. Such vectors may be prepared by means of standard recombinant techniques well known in the art. See for example, see Ausubel (1992); Sambrook and Russell (2001); and U.S. Pat. No. 5,837,492.

Large amounts of the protein of the invention may be produced (a) by expression in a suitable host or transgenic animal, (b) in vitro, for example, using a T7 system (see, for example, Ausubel et al., supra, or other standard techniques) or (c) by chemical synthesis using techniques well known in the art (e.g., by the methods described in Solid Phase Peptide Synthesis, 2nd ed., 1984, The Pierce Chemical Co., Rockford, Ill.). Expression vectors may include, for example, an origin of replication or autonomously replicating sequence (ARS) and expression control sequences, such as a promoter, an enhancer and necessary processing information sites, such as ribosome-binding sites, RNA splice sites, polyadenylation sites, transcriptional terminator sequences, and mRNA stabilizing sequences. Secretion signals may also be included where appropriate which allow the protein to cross and/or lodge in cell membranes. Other signals may also be included where appropriate which allow translocation to a specific cellular compartment (for example, endoplasmic reticulum, nucleus, peroxisome, etc.) and/or retention in a compartment. For example, the amino acid KDEL (SEQ ID NO:20) can be used to retain proteins in the endoplasmic reticulum. Such vectors may be prepared by means of standard recombinant techniques well known in the art. See for example, see Ausubel (1992); Sambrook and Russell (2001); and U.S. Pat. No. 5,837,492.

Once the recombinant protein of the invention is expressed, it may be isolated, for example, using affinity chromatography. In one example, an anti-Conus PDI protein antibody (for example, produced as described herein) may be attached to a column and used to isolate the PDI protein. Lysis and fractionation of PDI protein-harboring cells prior to affinity chromatography may be performed by standard methods (see, e.g., Ausubel et al., supra).

Once isolated, the recombinant protein can, if desired, be further purified, for example, by high performance liquid chromatography (see, e.g., Fisher, Laboratory Techniques in Biochemistry and Molecular Biology, eds., Work and Burdon, Elsevier, 1980).

The proteins of the invention may be cotranslationally, post-translationally or spontaneously modified, for example, by acetylation, farnesylation, glycosylation, myristoylation, methylation, prenylation, phosphorylation, palmitoylation, sulfation, ubiquitination and the like. See, Wold, F. (1981), Annu. Rev. Biochem. 50:783–814.

The protein disulfide isomerase of the invention is isolated following expression in a suitable host or chemical synthesis using techniques well known in the art. The isolated protein disulfide isomerase of the invention is used to correctly fold disulfide-containing proteins. The protein disulfide isomerase is contacted with the unfolded or misfolded protein and allowed to direct the proper folding of the protein. The correctly folded protein is isolated and purified using techniques well known in the art.

The nucleic acid encoding a protein disulfide isomerase of the invention is used to correctly fold disulfide-containing proteins in vivo using techniques well known in the art. In one embodiment, a suitable host is prepared which contains an expression vector containing a protein disulfide isomerase encoding nucleic acid of the invention and an expression vector containing a nucleic acid encoding a disulfide-containing protein. Such disulfide-containing proteins include conotoxins. Nucleic acids encoding conotoxins are well known in the art. See, U.S. Pat. No. 5,739,276. Nucleic acids encoding other disulfide-containing proteins are also well known in the art. In a second embodiment, a suitable host is prepared which contains an expression vector containing a protein disulfide isomerase encoding nucleic acid and a nucleic acid encoding a disulfide-containing protein. In either embodiment, the host cells are grown under conditions suitable for growth and expression of the protein disulfide isomerase and the disulfide-containing protein. The protein disulfide isomerase acts on the disulfide-containing protein in vivo to properly fold the protein.

The protein disulfide isomerase is cloned into an expression cassette, which is driven by a promoter appropriate for the host cell and contains other transcriptional and translational signals necessary for expression of the PDI in the host cell. The protein disulfide isomerase is expressed in mammalian cells using standard techniques known in the art. For example, the PDI is placed under the control of a promoter, such as the Drosophila inducible metallothionein promoter, and introduced into Drosophila cells. The PDI is followed by a poly (A) signal recognized by the host cell.

The protein disulfide isomerase of the invention can be expressed as a fusion protein, wherein the PDI gene is fused in frame to a disulfide-rich peptide. The fusion may include additional sequences between the PDI gene and the disulfide-rich peptide, for example, a proteolytic cleavage site. The fusion may also include a signal sequence, ER retention signals, and the like.

Anti-PDI Antibodies:

Using the PDI polypeptide described herein or isolated as described above, anti-PDI antibodies may be produced by any standard technique. In one particular example, a PDI cDNA or cDNA fragment encoding a conserved PDI domain is fused to GST, and the fusion protein produced in E. coli by standard techniques. The fusion protein is purified on a glutathione column, also by standard techniques, and is used to immunize rabbits. The antisera obtained is then itself purified on a GST-PDI affinity column and is shown to specifically identify GST-PDI, for example, by Western blotting.

Polypeptides for antibody production may be produced by recombinant or peptide synthetic techniques (see, e.g., Solid Phase Peptide Synthesis, supra; Ausubel et al., supra).

For polyclonal antisera, the peptides may, if desired, be coupled to a carrier protein, such as KLH as described in Ausubel et al., supra. The KLH peptide is mixed with Freund's adjuvant and injected into guinea pigs, rats, goats or, preferably, rabbits. Antibodies may be purified by any method of peptide antigen affinity chromatography.

Alternatively, monoclonal antibodies may be prepared using a PDI polypeptide (or immunogenic fragment or analog) and standard hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerling et al., In: Monoclonal Antibodies and T Cell Hybridomas, Elsevier, N.Y., 1981; Ausubel et al., supra).

In addition antibody fragments which contain specific binding sites for *Conus* PDIs may be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse, W. D. et al. (1989), Science 256:1275–1281).

Once produced, the polyclonal or monoclonal antibody is tested for specific PDI recognition by Western blot or immunoprecipitation analysis (by the methods described in Ausubel et al., supra). Antibodies which specifically recognize a PDI polypeptide described herein are considered to be useful in the invention.

The invention is described by reference to the following Examples, which are offered by way of illustration and are not intended to limit the invention in any manner. Standard techniques well known in the art or the techniques specifically described below were utilized.

EXAMPLE I

Purification of Protein Disulfide Isomerase from *Conus textile*

Preparation and purification of protein disulfide isomerase from *Conus textile* was performed as described by Lambert and Freedman (Lambert and Freedman, 1983). Dry venom ducts were ground under liquid N$_2$ and then homogenized in 10 mM Tris.HCl (pH 7.8) containing 0.25 M sucrose and 5 mM EDTA. The nuclei, whole cells, mitochondria and lysosomes were removed by centrifugation. The supernatant was adjusted to pH 5.2 and stirred to precipitate the microsomal fraction. The microsomal material was harvested by centrifugation and the pellet was homogenized in 10 mM Tris.HCl (pH 7.8), stirred for 2 hours and then centrifuged. The soluble microsomal fraction was dialyzed against the same buffer for 48 hours.

(NH$_4$)$_2$SO$_4$ was added to the dialyzed extract to 50% saturation. After stirring for 1 hour, the solution was centrifuged and the pellet was discarded. Additional (NH$_4$)$_2$SO$_4$ was added to the supernatant to the final concentration of 85% saturation and the solution was centrifuged as before. The pellet was dissolved in 0.1 M Tris.HCl (pH 7.8) and dialyzed against the same buffer for 24 hours.

The dialyzed material was loaded onto a DEAE-Sephadex A-50 column, equilibrated with 0.1 M Tris.HCl (pH 7.8). For elution, a linear NaCl gradient was applied. PDI is detected between 0.3 and 0.4 M NaCl by SDS-polyacrylamide gel electrophoresis.

Edman Sequencing of PDI from *Conus*

Figures 4A, 4B:
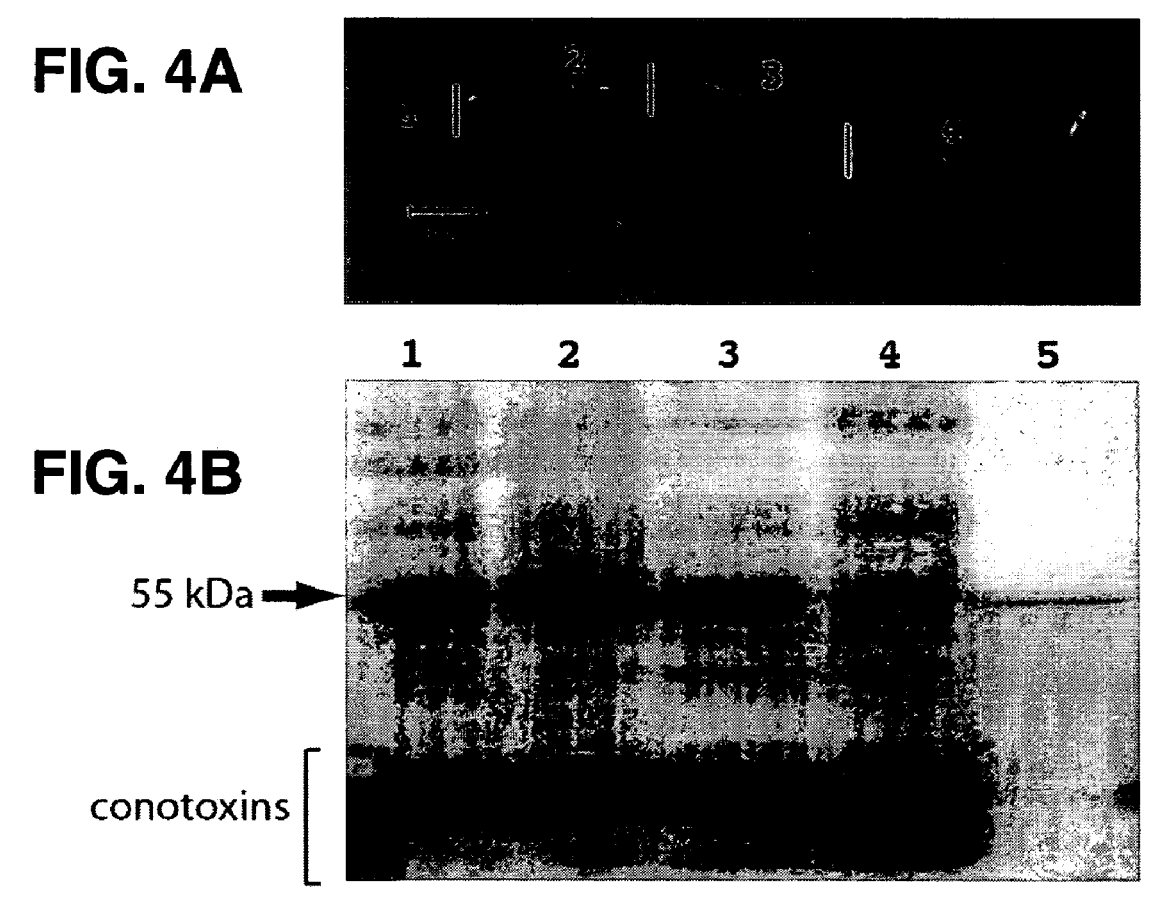

The venom duct was dissected from *Conus textile* and immediately divided into four equal parts, FIG. 4A. Each part of the venom duct was grounded under liquid nitrogen. Extraction was performed in 1 ml of 20% acetonitrile, 0.1% TFA at 4° C. After 1 hour of incubation, the solution was centrifuged and the resulted pellet was dissolved in 1 ml of 10% acetonitrile, 0.1% TFA. The solution was mixed for 1 hour at 4° C. and then centrifuged. 50 µl of supernatant was lyophilized and dissolved in 30 µl of SDS-electrophoresis buffer, boiled for 5 minutes and applied on 4–20% Tris-glycine gel. The proteins were then electroblotted onto an Immobilion PVDF membrane (0.45 µm) (Millipore) for 1 hour at 50 V. Proteins were visualized using Coomassie Blue staining and the protein band of 55 kDa was cut out from the membrane. Amino acid sequencing was performed by the Edman degradation method.

From the Coomassie-stained gel, shown in FIG. 4B, it is apparent that a band corresponding to 55 kDa protein was predominant and was found in each section of the venom duct. This band had a similar molecular weight to that of a bovine PDI (used as a reference in lane 5). The following sequence was obtained from 10 cycles: EEVEQEENVY (SEQ ID NO:21). This sequence matched the predicted amino acid sequence of the mature protein disulfide isomerase cloned from a venom duct of *Conus textile* (SEQ ID NO:2), confirming that the 55 kDa band corresponds to PDI. It thus appears that PDI is a major protein component of venom ducts. The *Conus* PDI was also not cross-reactive with polyclonal antibodies against bovine PDI (data not shown), suggesting substantial differences between bovine and *Conus* PDI.

EXAMPLE II

In vitro Folding of α-GI and Pro-GI with Protein Disulfide Isomerase Synthesis and Folding of Reference Pro-GI Pro-GI was chemically synthesized using two different types of thiol protecting groups. Cys1 and Cys3 were blocked with trityl (Trt) groups, and Cys2 and Cys4 were blocked with the acetamidomethyl (Acm) groups. The peptide was cleaved from the resin concurrent with the removal of the Trt protecting groups, and the first disulfide bond was formed in 0.1 M Tris.HCl (pH 8.7) containing 1 mM EDTA, 1 mM oxidized glutathione (GSSG) and 2 mM reduced glutathione (GSH) at 20 µM peptide concentration. After 1 hour of oxidation at room temperature, the reaction was quenched with 8% formic acid. The pro-GI concentration was determined spectrophotometrically using the molar absorbance coefficient at 274.5 nm, $\epsilon=1420$ M$^{-1}$×cm$^{-1}$ (Pace et al., 1995). Pro-GI with the first disulfide bridge oxidized (Cys1–Cys3) was purified on a Vydac C$_{18}$ semi-preparative HPLC column to approximately 90% purity. The peptide was eluted from the column using a two-buffer system in a linear gradient of 10% solvent B to 30% solvent B over 60 minutes where solvent A is 0.1% trifluoroacetic acid (TFA) and solvent B is 90% acetonitrile with 0.1% TFA. The Acm protecting groups were removed from the remaining two cysteines (Cys2 and Cys4) and the cysteines were oxidized in a single step using iodine oxidation. The correctly folded peptide was purified as described before to over 90% purity. This material was used as a reference to follow the PDI catalyzed folding of pro-GI.

In general, this approach involves the use of purified PDI in combination with any in vitro refolding reaction. In another example, a recombinant protein of interest is expressed (for example, in an *E. coli* or mammalian cell culture system) and is treated with a denaturant, such as guanidine hydrochloride. The protein preparation is then allowed to refold by dilution of the denaturant, and proper disulfide bond formation is promoted during this renaturation step by the presence of PDI protein in the reaction mixture. If desired, the PDI protein may be added in a buffer combined with oxidized and reduced glutathione and/or other purified PDIs or chaperones. Additional proteins may be added, such as Ero1. The PDI may also be added to in vitro transcription and/or translation systems such that improved folding is achieved.

Identification of Native proGI and proPVIA:

Identification of proGI folding species, containing the native disulfides, was verified by coelution with correctly folded proGI, which was produced in the two-step folding reaction. Identification of proPVIA folding species containing the native disulfides was based on limited digestion by bovine trypsin. The proPVIA forms generated by oxidation in the presence of glutathione were dissolved in a solution of bovine trypsin (150 ng/ml of 0.1 M Tris/HCl, pH 8.7) to give an enzyme/substrate weight ratio of 1:100. After 16 hours of incubation at room temperature the digestion products were separated from one another on a Vydac $C_{18}$ analytical HPLC column. Solvents A (0.1% trifluoroacetic acid) and B (90% acetonitrile and 0.1% trifluoroacetic acid) were mixed to form a linear gradient of 15% to 60% over the course of 30 minutes. The form of proPVIA with the retention time corresponded to the δ-PVIA, containing native disulfides, was isolated and coeluted with native material. The HPLC coelution of the isolated digestion product with the native peptide confirmed the identity of this species as having a native configuration. Additionally, the identity of digestion product, corresponding to the native δ-PVIA, was confirmed by electrospray mass spectrometry (ESI-MS).

Mass Spectrometry:

Electrospray mass spectrometry of peptides used in this study was performed with Quatro II Micromass mass spectrometer and Masslynx software. Samples were dissolved in methanol/water (1:1, v/v) containing 0.01% TFA. Molecular masses of all peptides were within 1.0 atomic unit from those expected from the amino acid sequence.

Oxidative Folding Reactions:

Standard oxidative folding reactions of α-GI and proGI were performed in 0.1 M Tris/HCl, pH 8.7, containing 1 mM EDTA, 0.5 mM GSSG and 5 mM GSH, at 22° C. The folding experiments catalyzed by bovine protein disulfide isomerase (PDI) were carried out in 0.1 M Tris/HCl, pH 7.5, containing 1 mM EDTA, 0.1 mM GSSG and 2 μM PDI, at 0° C. The reaction was initiated by adding the linear peptide to the folding mixture to the final concentration of 20 μM. After an appropriate time, the reaction was quenched by adding formic acid to the final concentration of 8%. The disulfide-bounded species were separated on a Vydac $C_{18}$ analytical HPLC column. Solvents A (0.1% trifluoroacetic acid) and B (90% acetonitrile and 0.1% trifluoroacetic acid) were mixed to form a linear gradient of 5% to 30% for 40 minutes and 15% to 25% for 60 minutes for elution of α-GI and proGI, respectively.

Standard oxidative folding reactions of δ-PVIA and proPVIA were performed in 0.1 M Tris/HCl, pH 7.5, containing 1 mM EDTA, 1 mM GSSG and 2 mM GSH, at 0° C. and a peptide concentration of 10 μM. After 16 hours the reaction was quenched as described before. The disulfide-bounded species were separated on a Vydac $C_{18}$ analytical HPLC column. Solvents A and B were mixed to form a linear gradient of 15% to 60% for 30 minutes for both δ-PVIA and proPVIA.

Concentrations of all peptides were determined spectrophotometrically using the molar absorbance coefficient at 274.5 nm, $\epsilon=1420$ $M^{-1}\times cm^{-1}$ for α-GI and proGI or $\epsilon=M^{-1}\times cm^{-1}$ and $\epsilon=M^{-1}\times cm^{-1}$ for δ-PVIA and proPVIA, respectively (Pace et al., 1995).

Synthesis of Precursors for α-GI and δ-PVIA Conotoxins:

Two model disulfide-rich peptides were chemically synthesized, denoted as proGI and proPVIA, for the respective conotoxins, α-GI and δ-PVIA. The sequences of synthetic peptides were identical with the native ones, predicted from cDNA sequence analysis.

The proGI was synthesized in two versions, where either all four cysteines were Trt-protected, or two (Cys1 and Cys3) were protected by Trt groups and two (Cys2 and Cys4) by Acm groups. The first variant of proGI, all four cysteines Trt-protected, was used in this experiment. The thermodynamic and kinetic parameters of folding were compared with the same parameters for the mature toxin. The proGI with native disulfides, folded according to the two-step folding procedure, was used as an HPLC reference for the coelution studies.

The proPVIA was synthesized with all six cysteine residues protected by Trt groups. After cleavage from the resin and purification on HPLC reverse phase column, the proPVIA was used in the folding experiments. Since a reference with native cysteine connectivity for proPVIA folded was not available, an HPLC reference was generated through trypsin digestion of the native form of proPVIA. Coelution experiment with digestion product of proPVIA and native δ-PVIA confirmed correct cysteine connectivity of folded proPVIA. Additionally, we measured the molecular weight of proPVIA folded digestion product. Molecular mass was within 0.5 atomic mass unit from those determined and calculated for native δ-PVIA.

Synthetic precursors were purified to over 90% homogeneity on reverse-phase $C_{18}$ HPLC column and the identity was confirmed by electrospray ionization mass spectrometry (Table 1).

TABLE 1

| Mass of synthetic precursors. | |
|---|---|
| Synthetic Precursor | Mass |
| pro-GI | 4562.1 Da |
| pro-PVIA | 6476.0 Da |

Role of Propeptide in Uncatalyzed and PDI-Catalyzed Folding:

Since the propeptide sequence may stabilize not only native conformation, but also the conformation(s) favoring productive folding pathway(s), we assessed if the propeptide can change the rate of the oxidative folding of a conotoxin peptide. The redox buffer was used to favor a steady-state accumulation of many different folding species. δ-PVIA accumulated to only 1–3% in the presence of 1 mM GSSG/2 mM GSH and even minor changes in the thermodynamic stability of the native conformation would be easily detected. Under our in vitro folding conditions, the propeptide affected neither kinetics nor thermodynamics for forming the native disulfide bonds.

Figure 5A:
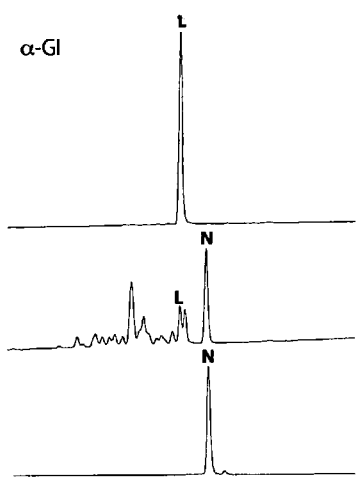
FIGS. 5A–5D are the steady-state distributions of the folding species for α-GI and δ-PVIA (FIGS. 5A and 5B) compared to their prosequences, pro-GI and pro-PVIA (FIGS. 5C and 5D). Linear and correctly folded forms are denoted as L and N, respectively. The α-GI and pro-GI were folded at 22° C. in 0.1 M Tris/HCl containing 1 mM EDTA, 0.5 mM GSSG and 5 mM GSH and the steady state was observed after 15 minutes of reaction. The δ-PVIA and pro-PVIA were folded at 0° C. in 0.1 M Tris/HCl containing 1 mM EDTA, 1 mM GSSG and 2 mM GSH and the steady state was observed after 16 hours of reaction. The top chromatograph in each panel shows the initial conditions, the middle chromatograph shows intermediate folding species and the bottom chromatograph shows the final folding species.
Figure 5B:
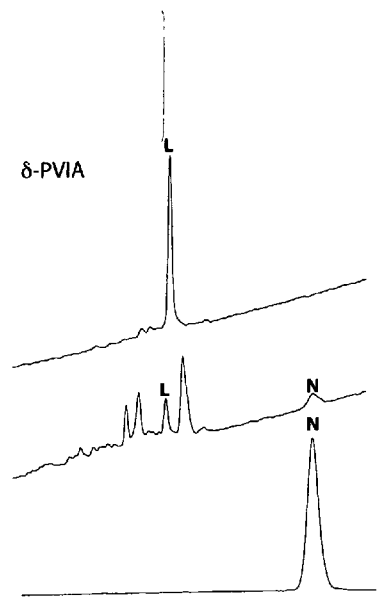
Figure 5C:
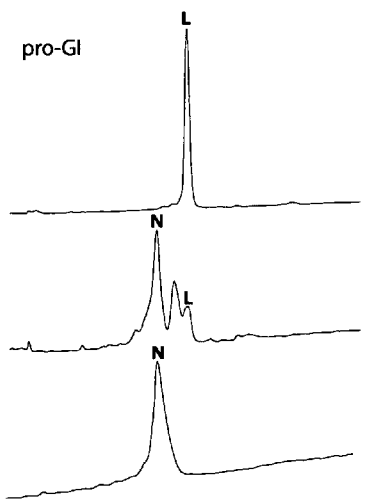
Figure 5D:
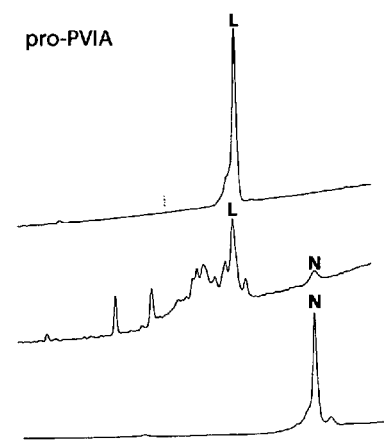

Oxidative folding of α-GI, pro-GI, δ-PVIA and pro-PVIA was carried out in buffered solutions containing oxidized and reduced glutathione, as described above. After an appropriate time, the folding reactions were quenched by acidification and analyzed by reversed-phase HPLC. The steady-state distribution of the folding species for pro-GI, pro-PVIA and the corresponding mature species α-GI and δ-PVIA are shown in FIGS. 5A–5D. The equilibrium accumulation of the native forms was similar for the mature toxins and the respective propeptide-containing variants: 20% yield of the native α-GI, as compared to 27% yield of the native pro-GI. Despite no effects of propeptide on a relative accumulation of the native forms, the number of the steady-state folding species was significantly reduced for pro-GI, as compared to that for α-GI (FIGS. 5A and 5C). There was no significant difference in accumulation of the native form of δ-PVIA compared with pro-PVIA: 2.1% versus 3.3%, as well as in the number of accumulated folding species.

To explore a possibility that propeptide could influence the oxidative folding under different experimental conditions, we screened several factors, such as temperature, redox potential, denaturants or osmolytes. As summarized in FIG. 6, varying the folding environment in the presence of the N-terminal propeptide sequence did not significantly change the steady-state distribution of the native species. The accumulations of the native α-GI and pro-GI were equally sensitive to the different conditions, despite changes in the temperature from 0° C. to 37° C., redox potential from 1:1 to 1:10 GSSG/GSH or the presence of other folding additives, such as urea, glycerol, nonionic detergents or organic cosolvents. In the case of δ-PVIA and pro-PVIA, addition of the nonionic detergent Tween-40 increased the accumulation of the native forms by 3- and 1.7-fold, respectively. These results confirmed that the propeptide sequences did not directly participate in the stabilization of the native conotoxins.

Figure 6:
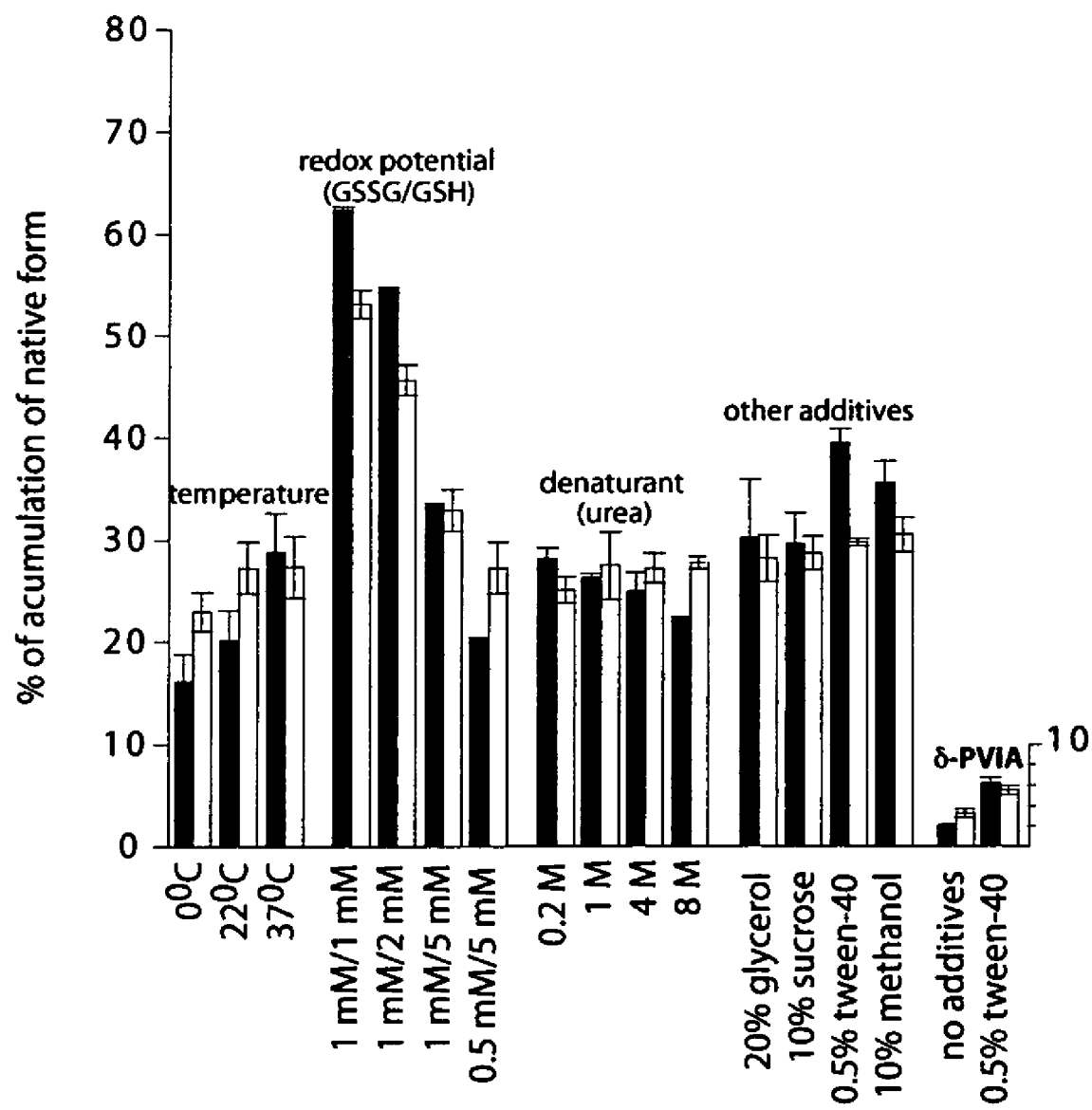
FIG. 6 shows the effects of the propeptide on the stability of native α-GI and δ-PVIA. Changes in accumulation of the native forms for α-GI and δ-PVIA (black bars) and their prosequences (open bars) are shown. The percentage of the native form accumulation was averaged from three separate folding experiments and the standard deviation is marked. Folding experiments were performed for 2 hours in 0.1 M Tris/HCl, pH 8.7, 1 mM EDTA at 20 µM peptide concentration (α-GI and pro-GI) and 16 hours in 0.1 M Tris/HCl, pH 7.5, 1 mM EDTA at 10 µM peptide concentration (δ-PVIA and pro-PVIA).

We also investigated whether the propeptide could influence the folding rates. The kinetics for forming a first disulfide bond is represented by a rate of disappearance of a linear form. These rates were determined under two different experimental conditions: (i) in the presence of 0.5 mM GSSG and 5 mM GSH, where the folding rates are determined by intramolecular rearrangement steps and (ii) with 0.1 mM GSSG, where folding rates are determined by the reactivity of the peptide Cys thiols (reference Creighton, Goldenberg). As illustrated in FIGS. 7A–D, 8A and 9, the disappearance of the linear forms was comparable for both α-GI ($k_{app}$=0.039 min-1 at 0.1 mM GSSG) and pro-GI ($k_{app}$=0.039 min-1 at 0.1 mM GSSG). In the presence of 0.5 mM GSSH and 5 mM GSH, the apparent rates for α-GI and pro-GI were also similar: $k_{app}$=0.084 min-1 and $k_{app}$=0.073 min-1, respectively (FIG. 6). Thus, the propeptide sequence did not affect the early folding steps. In addition, the formation of the native α-GI or pro-GI and the appearance of the other folding species were almost identical for the mature toxin and propeptide-containing variant, suggesting that the propeptide did not change the overall folding rates, FIGS. 7A–D, 8A and 9. As will be apparent to a person of skill in the art, the methods and results of this experiment are applicable to other proteins.

Comparison of the rates of the first disulfide bond formation in the fully reduced α-GI and proGI shows that the disappearance of both linear forms is comparable and propeptide does not affect early steps of the oxidative folding of conotoxins (FIGS. 7A–D, 8A and 9). Also formation of the native forms and appearance of the other folding species did not differ significantly between mature toxin (α-GI) and the propeptide-containing variant (proGI) (FIGS. 7A–7D, 8A and 9). The results demonstrate that the propeptide did not change the rate of oxidative folding.

As previously decribed, efficient disulfide bond formation in eukaryotic cells is assisted by protein disulfide isomerase. To determine the catalytic effect of PDI on the propeptide-facilitated folding, we carried out the α-GI and proGI oxidation experiments in the presence of bovine PDI (FIGS. 7B, 7D, 8A and 9). The reactions were performed at an enzyme-to-substrate molar ratio of 1:10 and under cysteine residue reactivity, i.e., under very low concentration of GSSG, 0.1 mM.

Figure 7A:
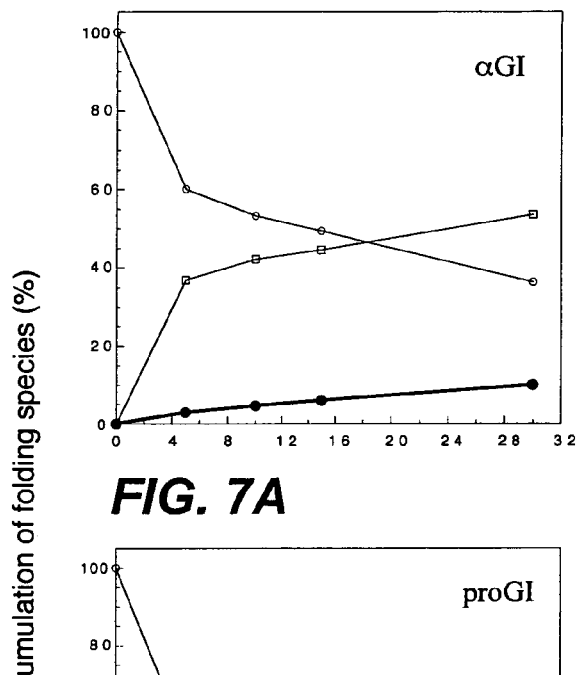
FIGS. 7A–7D show the kinetics of the PDI-catalyzed folding of αGI and proGI compared to the uncatalyzed reaction.
Figure 7B:
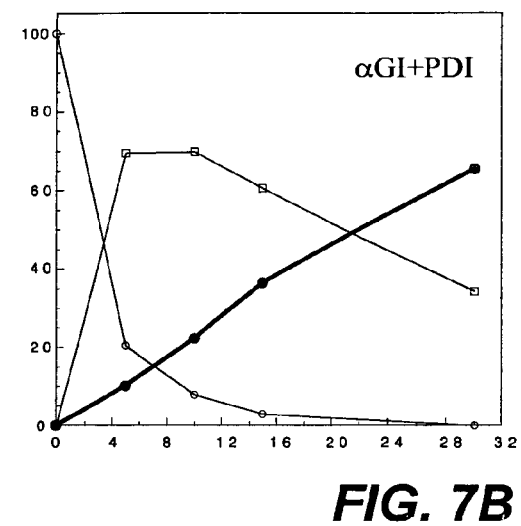
Figure 7C:
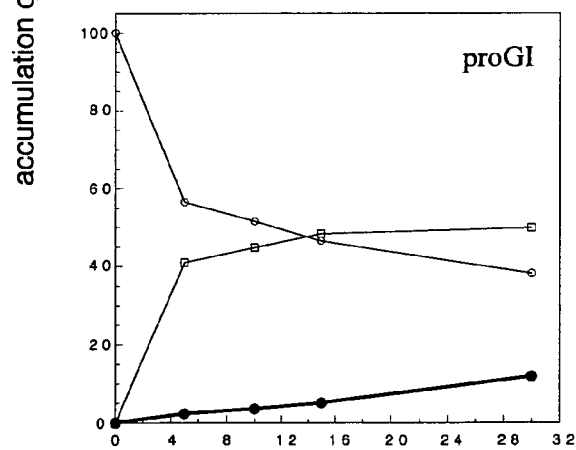

FIGS. 7B, 7D, 8A and 9 show the kinetics of the PDI-catalyzed folding of α-GI and proGI (for example, FIGS. 7B and 7D, respectively) compared with uncatalyzed reactions (FIGS. 7A and 7C). The folding reactions were carried out under identical experimental conditions as described in the previous section, except that PDI was added to the folding mixture prior to the addition of the linear peptide. Under folding conditions with a mixture of 0.5 mM GSSG and 5 mM GSH, PDI was primarily present in the reduced form (estimated $PDI_{(red)}/PDI_{total}$ was at least 97%, based on $K_{ox}$ of 1.3 mM (pH 7.4)—Darby, Creighton 1995, or at least 99% based on $K_{ox}$ of 0.7 mM (pH 8.0) Schwaller, Wilkinson, Gilbert 2003). In the presence of 0.1 mM GSSG, the enzyme was predominantly in the oxidized state.

Figure 8A:
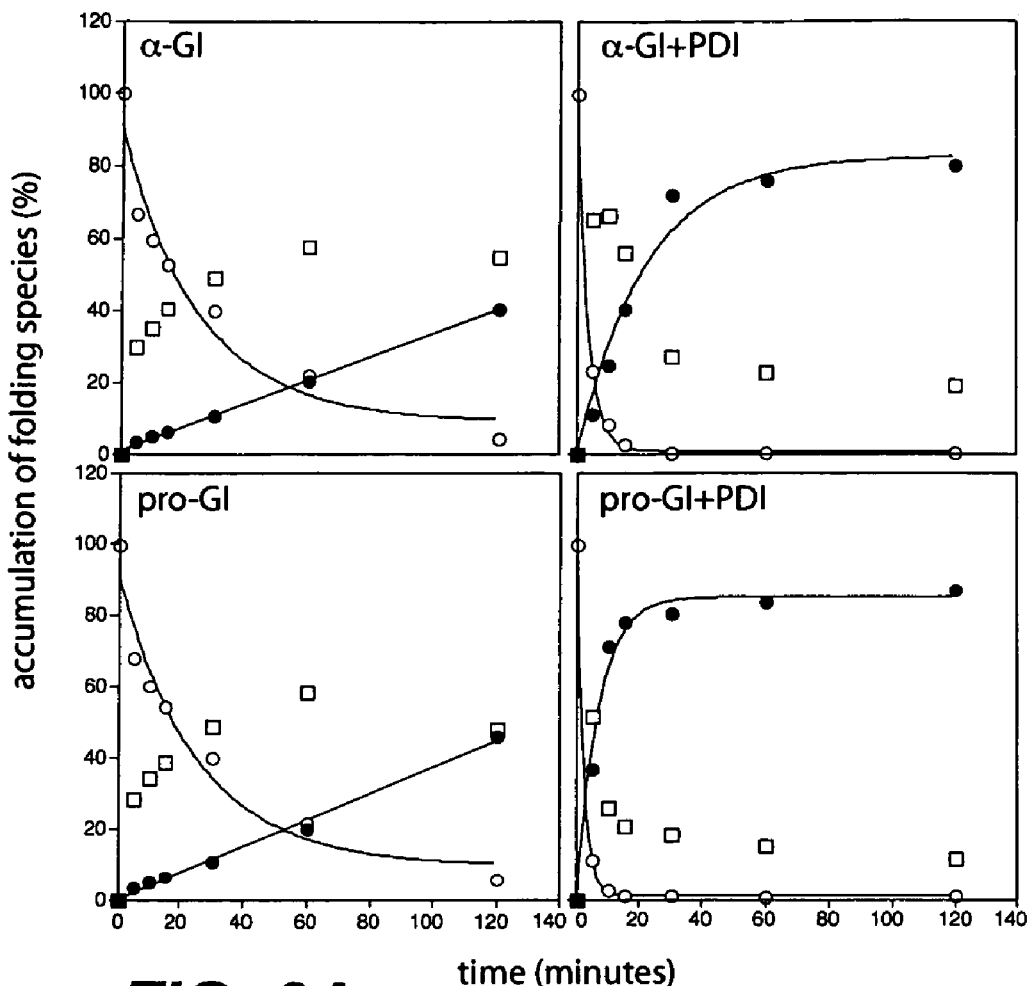
FIG. 8 shows A) folding kinetics for the PDI-catalyzed and uncatalyzed oxidation of α-GI and pro-GI. The folding reactions were carried out at 0° C. in 0.1 M Tris/HCl, pH 7.5, containing 1 mM EDTA, 0.1 mM GSSG and 2 µM PDI. The filled and open circles denote native and linear forms, respectively, and the open squares represent other folding species. The experimental points were analyzed by single exponential curve fit and the $k_{app}$ values for appearance of native (only in the presence of PDI) and disappearance of linear form (in the presence or absence of PDI) were calculated. For appearance of native form in the uncatalyzed reaction, we did not determine rate constants, as the points did not fit to the exponential curve. B) shows the half times for PDI-catalyzed and uncatalyzed folding of α-GI and pro-GI. The open bars represent values for the linear form and the black bars represent values for native form.
Figure 8B:
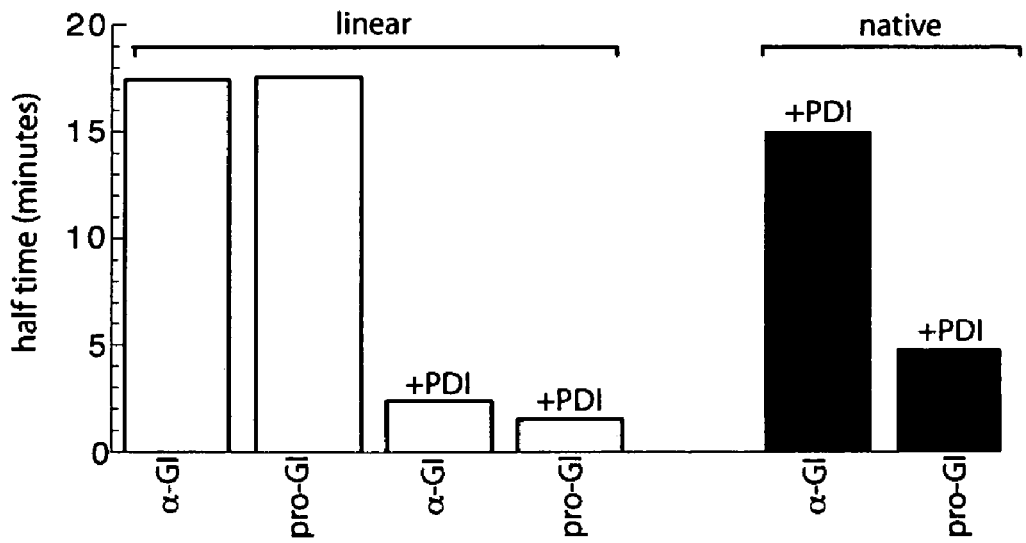

To determine the step of the toxin folding pathway catalyzed by PDI, we compared both the disappearance of linear forms, formation of native species and appearance of other folding species. Addition of PDI led to a significantly higher accumulation of the native form of both α-GI and proGI. The significantly faster disappearance of the linear form was accompanied by the faster accumulation of the native form. The rates for forming a first disulfide (disappearance of the linear form) were identical for α-GI and proGI, $k_{app}$=0.039 min-1 (α-GI) and $k_{app}$=0.039 min-1 (proGI). However, there were significant differences in the kinetics of accumulation of the native form between mature and precursor toxin. As shown in FIG. 9D, the presence of PDI had a dramatic effect on the accumulation of the native form of proGI, compared to that of α-GI (FIG. 9B) in the early steps of folding reaction. After the first five minutes in the presence of PDI, the amount of the native form of proGI increased 10.8-fold, whereas the amount of the native form of α-GI increased only 3.4-fold. Similarly, after the next five minutes, the effect of PDI catalysis is about 3 times higher for the propeptide-containing form (FIG. 8A). The single-exponential fit to the experimental points yielded $k_{app}$=0.046 min-1 (α-GI) and $k_{app}$=0.145 min-1 (proGI). This 3-fold increase in the folding rates is further illustrated in FIG. 8B in a form of half-times. It is apparent that the PDI-catalyzed formation of the native pro-GI is more efficient, as compared to that of the mature conotoxin.

Figure 7D:
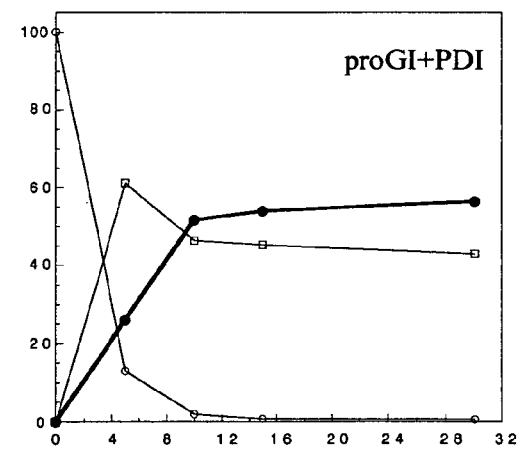

The rates of the PDI-catalyzed formation of the first disulfide bond in α-GI and proGI, measured by the time dependence of the disappearance of the linear form, were found to be very comparable (compare FIGS. 7B and 7D). However, in the case of α-GI, the disappearance of the fully reduced form is related to production of normative folding species. There was significantly lower accumulation of the normative folding species for proGI (FIGS. 7A–7D, 8A and 9A–9D). After ten minutes of folding, an accumulation of 44.8% of normative proGI folding species was observed, comparable with uncatalyzed formation of normative proGI folding species (46.3%). At the same time point, we observed almost 70% normative folding species in the PDI-catalyzed reaction of α-GI, over 1.5 times more when compared with uncatalyzed reaction (FIGS. 7A and 7B). These differences were not observed for the uncatalyzed folding (FIGS. 7A and 7C), suggesting that PDI is more efficient in rearrangement of the precursor folding species, as compared to that of the mature peptide. During the later time points, the accumulation of the other folding species was lower for α-GI, consistent with the equilibration experiments (the mature α-GI was more stable under a strongly oxidizing environment, as compared to proGI). Therefore, PDI did not change the thermodynamic stability of conotoxins, but rather influenced the productive folding pathway (s). Thus, PDI increased the rate of disulfide bond isomeration in the α-GI form and the rate and extent of natively folded proGI.

Interestingly, we did not observe such differences in the PDI-catalyzed folding of αGI and proGI when the reactions were carried out in the presence of 0.5 mM GSSG and 5 mM GSH. The enzyme increased the overall folding rates for both α-GI and pro-GI by approximately two-fold. The disappearance of the linear forms and the formation of the native forms for the precursor and the mature conotoxin were comparable (kinetic data not shown). The transient accumulation of the folding species was only slightly higher for α-GI in the presence of PDI (relative to the uncatalyzed reaction). Insufficient HPLC separation of the pro-GI folding intermediates precluded similar comparison for the precursor. The effect of the oxidative folding buffer, or redox system, on PDI-catalyzed folding of αGI and proGI results from changes in the catalytic efficiency of the enzyme over a range of reduced and oxidized glutathione concentrations (Lyles and Gilbert, 1991, Shwaller, Gilbert 2003). This effect was accounted for by the PDI redox state (the reduced dithiol form of PDI was required for the efficient folding of scrambled RNase), as well as by the redox state of the substrate itself.

It is apparent from the FIG. 2B in Lyles and Gilbert, 1991, that at the fixed 0.5 mM concentration of GSSG, increasing concentrations of GSH above 5 mM resulted in diminishing the differences between the PDI-catalyzed and uncatalyzed folding of RNase A. Indeed, we observed the identical phenomenon with the PDI-catalyzed and uncatalyzed folding of α-GI and pro-GI at 0.5 mM GSSH and 5 mM GSH.

This demonstrates that the propeptide alone does not appreciably contribute to the stability and the rate of oxidative folding of mature conotoxins. Further, bovine PDI facilitates the rate and amount of properly folded protein (FIGS. 7A–7D). The comparison of the folding species distribution at the early time points for α-GI and proGI, uncatalyzed versus PDI-catalyzed folding reaction, suggests that the propeptide could improve oxidative folding of conotoxins by making folding intermediate(s) better substrate(s) for PDI.

Figure 10:
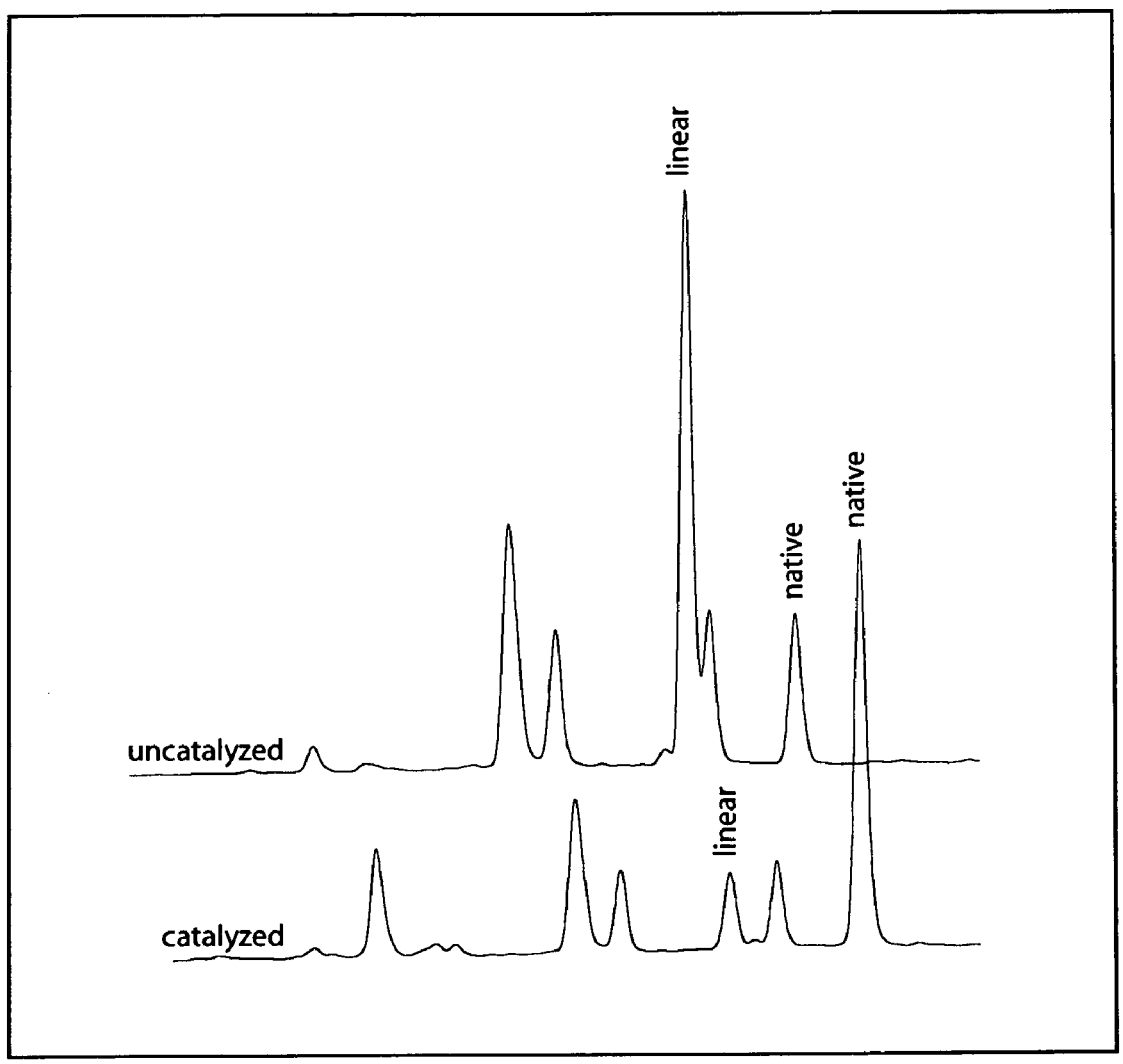
FIG. 10 shows chromatographs of the folding species. The chromatographs show the HPLC profiles of folding species of αGI catalyzed by purified *C. textile* PDI. The folding reactions were performed in Tris-HCl (pH 7.5) containing 1 mM EDTA and 0.1 M GSSG for 30 minutes at 0° C. α-conotoxin GI was used as the substrate at 20 µM concentration. The linear (L) and native (N) forms are marked.

FIG. 10 shows the activity of *Conus* PDI in the folding of αGI. *Conus* PDI increased the rate of disulfide bond isomeration and extent of natively folded αGI.

EXAMPLE III

Cloning of *Conus textile* Protein Disulfide Isomerase cDNA

Full-length *C. textile* PDI cDNAs were isolated by reverse transcription-PCR (RT-PCR) of venom duct RNA, using primers based on the highly conserved thioredoxin-like active site motif found in PDI genes isolated from other organisms. A typical Class 1 PDI gene would be expected to contain two nearly identical repeats of this sequence motif, separated by ~750–1000 bp of intervening sequence. A forward PCR primer was designed to match the N-terminal region sequence of the thioredoxin site (amino acid sequence VEFYAPW (SEQ ID NO:15); primer PDIfor1: GTN GAR TTY TAY GCN CCN TGG (SEQ ID NO:16)) and a reverse primer (amino acid sequence WCGHCKQ (SEQ ID NO:17); primer PDIrev1: YTG YTT RCA RTG NCC RCA CCA (SEQ ID NO:18)) were designed to the C-terminal portion of the thioredoxin site. These PCR primers, based on the protein sequences of PDI enzymes from a variety of differing organisms, contained degenerate codon usage to account for DNA sequence variation in the corresponding *Conus* genes. Venom duct tissue was dissected from *C. textile* snails and used to prepare mRNA and reverse-transcribed cDNA according to standard techniques. This venom duct cDNA was used for PCR amplification with the PDIfor1 and PDIrev1 primer pair. PCR amplification using a variety of different reaction conditions, thermostable polymerases, and cycling protocols consistently gave a predominant PCR product of ~1000 bp, as well as a variety of minor products. The prominent ~1000 bp PCR product was gel-purified and cloned into a plasmid vector, and several cloned isolates were sequenced. The DNA sequence of the cloned PCR product contained a single long open reading frame with significant homology to Class 1 PDI genes from other organisms (i.e., ~55% identity to human PDI proteins) and confirmed that this PCR product represented a *C. textile* PDI isoform. As predicted, this PCR-generated cDNA represented the gene sequence extending between the two thioredoxin-like domains and lacked the 5' and 3' regions of the full-length cDNA. The DNA sequence of this initial PCR product was used to design nested PCR primers for 5' and 3' RACE procedures (rapid amplification of cDNA ends) to isolate the full-length cDNA. *C. Textile* venom duct cDNA was synthesized with 5' and 3' RACE adapters and used for RACE amplifications. The nested 5' RACE primers generated a specific product of ~350 bp, and the 3' RACE primers gave a specific product of 1250 bp. These 5' and 3' RACE products were gel-purified, cloned into a plasmid vector, and sequenced. The sequences of each of these RACE products overlapped with the previously isolated central portion of the *C. textile* PDI cDNA, and together these 3 PCR-generated cDNAs could be merged to give the full-length cDNA sequence encoding the complete PDI protein. The full-length cDNA sequence contains a single long open reading frame encoding a *C. textile* Class 1 PDI protein of 502 amino acids. The cDNA sequence includes between about 30 and 140 bp of 5' untranslated sequences and between about 65 and 850 bp of 3' untranslated region sequences. Translation of the PDI ORF shown in SEQ ID NOs:1 and 5 initiates at the first ATG start codon from the 5' end. Translation of the PDI ORF shown in SEQ ID NO:3 initiates at the third ATG of the 5' sequence. The encoded proteins contain two thioredoxin-like domains, separated by 350 amino acids; each of these domains contains a cysteine redox-active site (—CGHC—) SEQ ID NO:19. The *C. textile* PDI enzyme contains a C-terminal ER retention signal, as predicted for a Class 1 enzyme functioning in the secretory pathway. The 3' RACE clone terminates in a typical poly-A tail, preceded by a poly-A addition signal, indicating that this clone represents the true 3'end of the mRNA. This initial cDNA sequence was generated by PCR using Taq polymerase and nested PCR amplifications utilizing up to 60 amplification cycles. It is possible that Taq polymerase misincorporation errors could be present in the initial sequence. To generate a cDNA clone of the entire coding region devoid of sequence errors, PCR primers were designed in the 5' and 3' untranslated regions immediately surrounding the open reading frame and used to amplify the complete 1500 bp coding region using an LA-PCR (long-accurate) protocol, proof-reading polymerase mixture, and only 20 amplification cycles. Amplification of *C. textile* venom duct cDNA gave a single, robust product at the predicted 1500 bp size. This product was cloned into a plasmid vector and completely sequenced on both strands to give the complete *C. textile* PDI nucleic acid sequence presented in SEQ ID NO:1.

In addition, we have isolated cDNA clones for three closely related PDI variants from *C. textile* venom duct. Although these sequences are distinct from any previously isolated PDI enzyme, they do display features typical of Class 1 PDI enzymes. In particular, the *Conus* enzymes have two conserved active site domains separated by ~350 amino acids and a C-terminal endoplasmic reticulum retention signal.

EXAMPLE IV

Expression of Protein Disulfide Isomerase in Host Cells

PDI may also be used to catalyze proper disulfide bond formation in any in vivo protein expression system. By this approach, a full-length PDI-expressing nucleic acid is introduced into a host cell which also expresses a disulfide-rich protein of interest. Preferably, the PDI gene encodes a *Conus* PDI, and the disulfide-rich protein is a conotoxin, preferably, produced at high levels in the cultured cells. Any appropriate eukaryotic cell may be used for protein expression in conjunction with a PDI product. This technique may be used for the production of any protein which is disulfide-rich.

EXAMPLE V

Synthesis of *Conus* PDI in Host Cells

Protein disulfide isomerase (PDI) enzymes, characterized by the presence of highly conserved thioredoxin-like active site domains, catalyze the formation of cysteine-cysteine disulfide linkages in nascent proteins. The PDI activity isolated from *Conus* venom duct is demonstrated to facilitate the folding of disulfide-rich peptides, such as conopeptide precursors.

The quantity of PDI enzyme that can be isolated from venom duct is limited by the impracticality of obtaining large quantities of this tissue. Functional expression of the cloned *Conus* PDI enzymes in heterologous expression systems will allow production of large amounts of the enzyme. The recombinantly produced enzyme can be purified and used to facilitate folding of synthetic conopeptide precursors in an in vitro folding reaction. In addition, any cloned cysteine-containing conopeptide precursor gene can be co-expressed in a recombinant cell line that has been engineered to express high levels of the *Conus* PDI enzyme. The high levels of PDI enzymatic activity will promote efficient folding of the processed, bioactive conopeptide and allow higher yields of recombinant conopeptide production.

A variety of recombinant expression systems based on bacterial, yeast, insect or mammalian cells could be utilized for the production of the *Conus* PDI enzyme. The recombinant expression of conopeptide precursors, under ideal conditions, presents more stringent requirements. Ideally, a cellular expression system will be able to recognize the conopeptide precursor signal sequence and direct the nascent protein into the secretory pathway where proper processing, folding, secondary modifications and extra-cellular secretion of the bioactive peptide can occur. In such a system, the co-expression of the cloned *Conus* PDI will facilitate efficient folding of the disulfide-rich conopeptide and promote higher yields of correctly folded peptide. Alternatively, the recombinant PDI gene may be modified to provide a precursor signal sequence recognized by the host.

Both insect cell and mammalian cell expression systems have the potential to carry out the necessary processing steps for conopeptide expression and could serve as suitable hosts. Insect cells have an advantage in the fact that the cell lines are easier and less costly to maintain. In addition, many of the insect cell lines can be grown in serum-free media, which can greatly simplify the purification of secreted peptide products.

There are two general methods for recombinant protein production in insect cell lines, the baculovirus systems and the nonlytic, plasmid-based stable expression systems. While the baculovirus systems are capable of very high expression levels, the transient, lytic nature of the viral infection can interfere with the synthesis of secretory proteins, and the debris from virus-induced cell death can make purification of small secreted conopeptide products more difficult. The stable insect cell expression systems utilize a plasmid expression vector with a strong, insect cell-specific viral promoter to drive transcription of the cloned cDNA, along with a drug-selectable marker that permits selection of stable cell lines continuously expressing the recombinant protein of interest. These systems reportedly give more reliable expression of secreted protein products. The continuous nature of peptide synthesis, coupled with the secretion into serum-free media, will facilitate purification of the conopeptide products. For these reasons, the insect cell stable expression system is an advantageous method, although it is realized that other expression systems could be utilized for expression of the *Conus* PDI, either alone or co-expressed with conopeptide precursors.

The 1600 bp *C. textile* PDI cDNA is cloned into an insect cell expression plasmid under the control of the OpIE2 promoter, capable of providing constitutive expression in a variety of insect cell lines. The PDI cDNAs is engineered to contain a C-terminal fusion of the V5 epitope to allow antibody detection of the recombinant protein, and a 6× His tag to permit purification by metal affinity chromatography. A stable clonal cell line expressing the PDI enzyme is selected using an expression plasmid which also contains the blasticidine resistance gene under the control of the OpIE1 promoter. The PDI expression construct is introduced into an appropriate insect cell line (HighFive, Sf9, Sf21, for example) by liposome-mediated transfection. Blasticidine selection is used to isolate stable clonal lines that express the PDI enzyme. Following an incubation period of 2–4 days, cellular protein extract is analyzed by Western blotting, using anti-V5 antisera, to determine the relative expression levels of the recombinant *Conus* PDI protein being produced in the various cell lines. One or more cell lines that gives abundant expression of the PDI protein, as determined by Western blot, is selected. A high-expression cell line is used for purification of the *Conus* PDI protein by standard methods already established for purification of the enzyme from venom duct tissue. As an alternative, the recombinant His-tagged protein is purified by affinity chromatography on nickel resin columns. Once a stable cell-line is established and characterized, it can provide a continuous source from which to isolate the *Conus* PDI enzyme. Cell stocks can be frozen for future use, and cells can be adapted to nonadherent high-density growth in spinner flasks to enable large-scale production of the recombinant protein.

Generation of a stable cell line with high-level constitutive expression of the *Conus* PDI enzyme will facilitate efforts to co-express conopeptide precursors. A large number of conopeptide precursor genes have been isolated, the majority of which encode peptides with numerous disulfide bonds. Recombinant expression of these genes may allow facile production of the bioactive peptides. Co-expression of high levels of the PDI enzyme may promote efficient folding of the processed mature peptide.

EXAMPLE VI

Synthesis of Conopeptide in Host Cells Expressing *Conus* PDI

Figure 11:
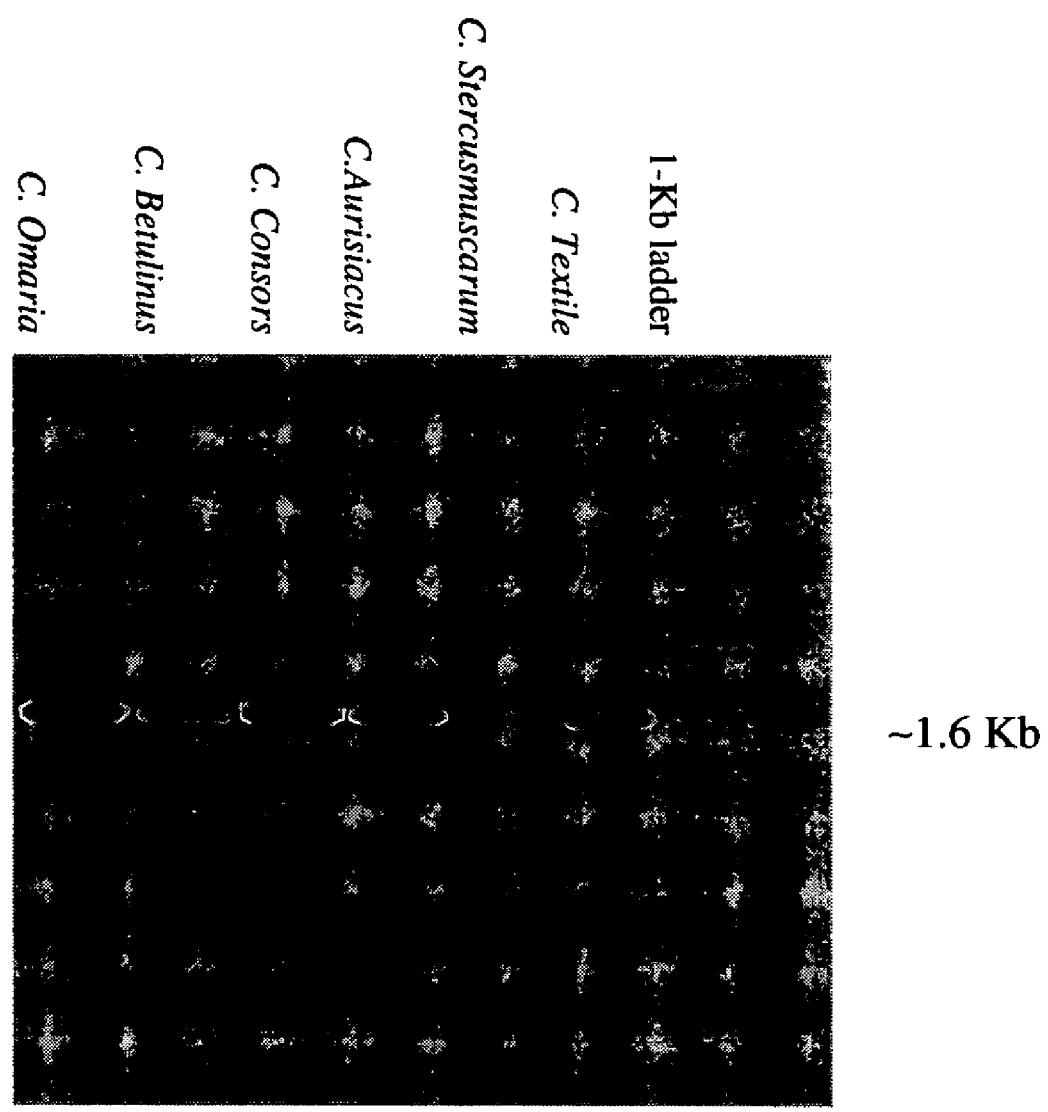
FIG. 11 shows PCR amplification of PDI from cDNA prepared from various *Conus* species. Lane 1 shows the PCR amplification product from *C. omaria*. Lane 2 shows the PCR amplification product from *C. betulinus*. Lane 3 shows the PCR amplification product from *C. consors*. Lane 4 shows the PCR amplification product from *C. aurisiacus*. Lane 5 shows the PCR amplification product from *C. stercusmuscarum*. Lane 6 shows the PCR amplification product from *C. textile*. Lane 7 shows the molecular weight markers, a 1 Kb ladder.

A Conopeptide precursor gene is cloned into a plasmid expression vector under the control of the OpIE2 promoter, to provide high-level constitutive expression in insect cell lines. The conopeptide genes encode a native signal sequence that should direct the nascent protein into the insect cell secretory pathway. Alternatively, the mature, bioactive conopeptide coding sequence is fused to the honeybee mellitin gene signal sequence, an insect-specific gene know to function as an efficient signal sequence in insect cell lines. The conopeptide gene is expressed as the native conopeptide sequence, or they can be engineered to contain a C-terminal fusion of an epitope tag or a 6×His affinity purification tag. While these C-terminal tags will permit efficient immuno-detection and purification of the recombinant conopeptide, the tag may interfere with the bioactivity of the peptide. In this case, a specific protease cleavage site is inserted between the conopeptide sequence and the tag sequence. In this embodiment, the conopeptide is purified using the tag and is then digested with a protease which cleaves at the inserted protease cleavage site. In specific instances, either alternative may be preferable. The expression construct may also contain the neomycin resistance gene, for dual selection of the conopeptide gene in the blasticidine-resistant PDI-expressing cell line. The conopeptide expression plasmid is introduced into the PDI-expressing cell line by liposome-mediated transfection, and the transfected cells is maintained in serum-free media. Following an incubation period of 2–4 days, culture media is harvested, concentrated, and analyzed for conopeptide production by gel electrophoresis, HPLC analysis or bioassay, depending on the particular conopeptide to be analyzed. The effectiveness of *Conus* PDI co-expression in improving bioactive conopeptide yield is determined by comparison to expression in native insect cell lines that lack the *Conus* PDI. For long-term conopeptide production, stable cell lines are selected by dual blasticidine-neomycin selection.

EXAMPLE VII

In Vivo Production of Recombinant PDI

The *Conus* PDI of SEQ ID NO:2 is modified by gene recombination technology so as not to code for the endoplasmic reticulum localization signal. The recombinant gene is linked to a highly active promoter, and introduced into host cells, which can multiply in a culture medium at nearly neutral pH, by transfection or transformation. For example, the recombinant gene is transformed into microorganism such as yeast, which is cultured in a culture medium free of a PDI activity inhibitor, such as a uracil-free minimal medium, with pH being kept nearly neutral using a buffer, for example, HEPES. A large amount of PDI having enzyme activity is expressed in the culture medium outside the cells.

An endoplasmic retention signal is modified by deleting, substituting, or adding one or more bases in a region encoding an endoplasmic reticulum localization signal of a gene encoding protein disulfide isomerase of *Conus* to modify the gene so as not to encode part, or all, of the endoplasmic reticulum localization signal. The modified PDI gene is positioned for expression in an expression vector and introduced into host cells. The host cells are cultured, thereby causing protein disulfide isomerase to be secreted in an active state outside the host cells.

In eukaryotic cells, secretion of proteins is performed usually along the following pathway: a secretory protein is translated from mRNA by the ribosome. During translation, the protein is transferred into the endoplasmic reticulum, and further transported to the Golgi apparatus, from which it is allocated through the secretory pathway to the vacuole, the cell membrane, and then the cell wall, or the outside of the cell. Signal sequences directing peptides to the secretory pathway are typically cleaved in the endoplasmic reticulum. Proteins, which should remain in the endoplasmic reticulum, also take the same route as the secretory protein, but once transported to the Golgi apparatus, they are transported back to the endoplasmic reticulum due to a special structure or sequence, in addition to a signal necessary for entry into the secretion pathway, such as a particular amino acid sequence comprising several residues (a consensus sequence), called a “motif” in which amino acid residues with similar properties may be substituted conservatively. The special structure or sequence necessary for persistent presence in the endoplasmic reticulum is designated an “endoplasmic reticulum localization signal.” For example, an endoplasmic reticulum localization signal may be a sequence, such as KDEL, located at the C-terminus of the protein.

Signal sequences may be added to the protein disulfide isomerase, thereby allowing targeting of the PDI to the appropriate organelle of a host system. For example, the signal sequence of *Conus* PDI, may be replaced with a secretory signal sequence recognized by *Sacchoromyces* or any other organism, where desirable or appropriate, thereby directing the protein to the desired organelle. Further, where desirable and appropriate, both the endoplasmic reticulum localization signal and signal sequence may be modified to produce a protein disulfide isomerase which is secreted into the medium or other desired locations.

EXAMPLE VIII

PDI activity is measured by a sensitive fluorescent assay using the method of Heuck, A. P., and Wolosiuk, R. A. (1997) *Anal. Biochem.* 248:94–101. Briefly, 4–20 mg of PDI protein is incubated in 0.2 ml of a 0.1 mM sodium phosphate buffer (pH 7.4) containing 75 mM dithiothreitol, 3 mM EDTA, and 0.7 mM di-fluoresceinthiocarbamyl-insulin at 37° C. Fluorescence is monitored using a spectrophotometer.

Alternatively, protein disulfide isomerase activity is measured by refolding of “scrambled” RNase, which had exchanged cystines, as described elsewhere in Lambert, N. and Freedman, R. B. (1983) *Biochem. J.* 213:235–243. Bovine protein disulfide isomerase (Sigma) is used as a positive control.

EXAMPLE IX

To test for the presence and abundance of PDI in other *Conus* species, a simple PCR sceening was done, using the primer set of PDI-20F and PDI-2 IR. Species tested include: *C. textile, C. stercusmuscarum, C. aurisiacus, C. consors, C. betulinus*, and *C. omaria*. The PCR was done using, approximately 1 ng of venom duct cDNA, and the standard protocol of Taq polymerase. The reaction was run on a one percent agarose gel and then stained using ethidium bromide. As shown in FIG. 11 the expected ~1550 bp band is seen in each lane. Although it is clear that PDI is present in the venom ducts of all *Conus* species, the concentration is believed to vary as indicated by differences in band intensity shown in FIG. 11. The faint band for *C. stercusmuscarum* is believed to be due primarily to a problem with the template DNA used for the PCR.

EXAMPLE X

Full-length *C. erminius, C. floridanus, C. geographus, C. gloriamaris, C. imperialis, C. magus, C. marmorceus, C. nigropunctatus, C. pennaceus, C. pennaceus, C. purpuracens, C. striatus, C. tulipa*, or other *Conus* species PDI cDNAs are isolated by reverse transcription-PCR (RT-PCR) of venom duct RNA, using primers based on the highly conserved thioredoxin-like active site motif found in the PDI genes isolated from *C. textile* or other organisms. The PDI genes isolated from *C. textile* (SEQ ID NO:1, SEQ ID NO:3 and SEQ ID NO:5) contain two conserved repeats of this sequence motif, separated by ~750–1000 bp of intervening sequence. A forward PCR primer is designed to match the N-terminal region sequence of the thioredoxin site as previously described, and a reverse primer is designed to the C-terminal thioredoxin site. These PCR primers will contain degenerate codon usage to account for DNA sequence variation in the corresponding *Conus* genes. Venom duct tissue is dissected from *C. erminius, C. floridanus, C. geographus, C. gloriamaris, C. imperialis, C. magus, C. marmorceus, C. nigropunctatus, C. pennaceus, C. pennaceus, C. purpuracens, C. striatus* or *C. tulipa* snails and used to prepare mRNA. The mRNA is reverse-transcribed into cDNA according to standard techniques. This venom duct cDNA is used for PCR amplification with the PDI forward and reverse primer pair previously described. PCR amplification is performed using standard methods known in the art and previously described to yield a PCR product. The PCR product is gel-purified, cloned into a plasmid vector, and several cloned isolates are sequenced. The open reading frame with significant homology to the PDI genes of SEQ ID NO:1 through SEQ ID NO:8 is identified. Using the above method, the open reading frame is predicted to extend between the two thioredoxin-like domains, and lack the 5' and 3' regions of the full-length cDNA. The DNA sequence of this initial PCR product is used to design nested PCR primers for 5' and 3' RACE procedures (rapid amplification of cDNA ends) to isolate the full-length cDNA. Venom duct cDNA from the appropriate species is synthesized with 5' and 3' RACE adapters and used for RACE amplifications. These 5' and 3' RACE products are gel-purified, cloned into a plasmid vector, and sequenced. The encoded PDI is determined based on the nucleic acid sequence.

Alternatively, The PDI sequence of SEQ ID NO:1, SEQ ID NO:3, SEQ ID NO:5 or SEQ ID NO:7, or a fragment thereof, is labeled, for example, with $^{32}P$. The cDNA library previously described is cloned into a vector and the vector library is transformed into a suitable host, for example, DH5α cells. The transformed cells are replica plated in triplicate and grown overnight. Three of the four plates are prepared for colony lift hybridization using standard techniques known in the art. The labeled nucleic acid is then hybridized to colony lift filters to identify clones containing the PDI genes. Positive clones are isolated, grown and the vector isolated. The isolated vector is sequenced.

While this invention has been described in certain embodiments, the invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims. Thus, the described embodiments are illustrative and should not be construed as restrictive.

All references, including publications, manuscripts, patents, and patent applications, cited herein are hereby incorporated by reference to the same extent as if each reference were individually and specifically indicated to be incorporated by reference and were set forth in its entirety herein.

What is claimed is:

1. An isolated nucleic acid comprising
a nucleic acid encoding
a protein disulfide isomerase comprising the amino acid sequence as set forth in SEQ ID NO:2
or a nucleotide sequence as set forth in SEQ ID NO:1.

2. The isolated nucleic acid of claim 1, further comprising vector sequences.

3. The isolated nucleic acid of claim 2, wherein said vector is an expression vector.

4. The isolated nucleic acid of claim 1, wherein said isolated nucleic acid is from a member of the genus *Conus*.

5. An isolated host cell comprising the nucleic acid sequence of claim 2.

6. An isolated host cell comprising the nucleic acid seciuence of claim 3.

7. The isolated host cell of claim 6, further comprising an expression vector encoding a disulfide-rich peptide.

8. A method for producing a protein disulfide isomerase comprising:
introducing into a host cell the isolated nucleic acid of claim 1;
expressing said protein disulfide isomerase; and
isolating said protein disulfide isomerase.

9. The method according to claim 8, wherein said cell is selected from the group consisting of an insect cell, Sf9, Sf21, *Drosophila* Schneider2, a mammalian cell, COS 1, NIH 3T3, HeLa, 293, CHO, U266, a plant cell, Baculovirus, *Saccharomyces, Schizosaccharomyces, Aspergillus, E. coli*, and *Bacillus*.

10. A method for producing a correctly-folded disulfide-rich peptide comprising:

introducing the nucleic acid of claim 1 encoding a protein disulfide isomerase and a nucleic acid encoding a disulfide-rich peptide into a host cell, wherein said nucleic acid encoding a protein disulfide isomerase and a disulfide-rich peptide comprise one or more nucleic acid molecules;

expressing said protein disulfide isomerase peptide and said disulfide-rich peptide, wherein said disulfide-rich peptide is a conotoxin; and isolating a correctly-folded disulfide-rich peptide.

11. The method according to claim 10, wherein said host cell is selected from the group consisting of an insect cell, Sf9, Sf21, *Drosophila* Schneider2, a mammalian cell, COS 1, NIH 3T3, HeLa, 293, CHO, U266, a plant cells, Baculovirus, *Saccharomyces, Schizosaccharomyces, Aspergillus, E. coli*, and *Bacillus*.

12. The method according to claim 10, wherein said protein disulfide isomerase peptide is from a member of the genus *Conus*.

13. A method for producing a correctly-folded disulfide-rich peptide comprising:

introducing into a host cell the nucleic acid of claim 1;

introducing a nucleic acid encoding a disulfide-rich peptide, wherein said nucleic acid encoding a protein disulfide isomerase and said nucleic acid encoding a disulfide-rich peptide comprise one or more nucleic acid molecules;

expressing said protein disulfide isomerase peptide and said disulfide-rich peptide; and isolating a correctly-folded disulfide-rich peptide.

14. The method according to claim 13, wherein said cell is selected from the group consisting of an insect cell, Sf9, Sf21, *Drosophila* Schneider2, a mammalian cell, COS 1, NIH 3T3, HeLa, 293, CHO, U266, a plant cells, Baculovirus, *Saccharomyces, Schizosaccharomyces, Aspergillus, E. coli*, and *Bacillus*.

15. The method according to claim 13, wherein said disulfide-rich peptide is a conotoxin.

* * * * *

```
                         SEQUENCE LISTING

<160> NUMBER OF SEQ ID NOS: 21

<210> SEQ ID NO 1
<211> LENGTH: 1601
<212> TYPE: DNA
<213> ORGANISM: Conus textile
<220> FEATURE:
<221> NAME/KEY: CDS
<222> LOCATION: (31)..(1536)

<400> SEQUENCE: 1
gaattcgccc ttactaggat ccgcatcatc atg aag ttt tca tct tgt tta gtt      54
                                 Met Lys Phe Ser Ser Cys Leu Val
                                 1               5 tta act ctt ctg gtt ttt gta tct gcc gaa gat gtc gaa cag gag gaa      102
Leu Thr Leu Leu Val Phe Val Ser Ala Glu Asp Val Glu Gln Glu Glu
    10                  15                  20 aat gtc cac gtt ttg acg aag aaa aat ttt gac tcc ttc ata act gat      150
Asn Val His Val Leu Thr Lys Lys Asn Phe Asp Ser Phe Ile Thr Asp
25                  30                  35                  40 aat gag ttc gtg ctt gtg gaa ttt tat gct ccc tgg tgt ggc cat tgc      198
```

```
Asn Glu Phe Val Leu Val Glu Phe Tyr Ala Pro Trp Cys Gly His Cys
             45                  50                  55 aag gca ttg gca cca gaa tat gcc aaa gct gca aca act ttg gaa aac    246
Lys Ala Leu Ala Pro Glu Tyr Ala Lys Ala Ala Thr Thr Leu Glu Asn
             60                  65                  70 gag aag tcg aac atc aag ttg gcc aaa gtg gat gct act gtg gag ggg    294
Glu Lys Ser Asn Ile Lys Leu Ala Lys Val Asp Ala Thr Val Glu Gly
             75                  80                  85 gat ttg gcc tcc aaa ttt gat gtt cgt gga tac cca aca atc aag ttc    342
Asp Leu Ala Ser Lys Phe Asp Val Arg Gly Tyr Pro Thr Ile Lys Phe
 90                  95                 100 ttc cgt aaa gag aag cct gat ggt cca gca gac tac agt ggt ggt cgc    390
Phe Arg Lys Glu Lys Pro Asp Gly Pro Ala Asp Tyr Ser Gly Gly Arg
105                 110                 115                 120 caa gct aaa gat att gtt gac tgg ctg aag aag aag aca gga cca cca    438
Gln Ala Lys Asp Ile Val Asp Trp Leu Lys Lys Lys Thr Gly Pro Pro
            125                 130                 135 gcc aag gaa ctg aag gag aaa gat gaa gtc aag gct ttt gtg gaa aaa    486
Ala Lys Glu Leu Lys Glu Lys Asp Glu Val Lys Ala Phe Val Glu Lys
            140                 145                 150 gat gaa gtt gtt gtc att ggt ttc ttc aag gat caa gaa tcc aca ggt    534
Asp Glu Val Val Val Ile Gly Phe Phe Lys Asp Gln Glu Ser Thr Gly
            155                 160                 165 gct ttg gcc ttc aaa aag gca gct gcc ggc att gat gac att cca ttt    582
Ala Leu Ala Phe Lys Lys Ala Ala Ala Gly Ile Asp Asp Ile Pro Phe
            170                 175                 180 gcc atc act tca gaa gat cat gtt ttc aag gag tac aag atg gac aaa    630
Ala Ile Thr Ser Glu Asp His Val Phe Lys Glu Tyr Lys Met Asp Lys
185                 190                 195                 200 gat ggc att gta ctg ctg aag aag ttt gat gag ggc cgt aat gac ttc    678
Asp Gly Ile Val Leu Leu Lys Lys Phe Asp Glu Gly Arg Asn Asp Phe
            205                 210                 215 gag ggg aat ttg gag gag gag gag gcc atc gtc aag cac gtc agg gaa    726
Glu Gly Asn Leu Glu Glu Glu Glu Ala Ile Val Lys His Val Arg Glu
            220                 225                 230 aac caa ctg cca ctg gtt gta gaa ttc act caa gag tct gcc cag aag    774
Asn Gln Leu Pro Leu Val Val Glu Phe Thr Gln Glu Ser Ala Gln Lys
            235                 240                 245 atc ttt gga ggt gag gtg aag aac cac att ctg ctg ttc ctg aag aag    822
Ile Phe Gly Gly Glu Val Lys Asn His Ile Leu Leu Phe Leu Lys Lys
250                 255                 260 gaa ggt gga gaa gac aca att gaa aag ttc aga agt gca gct gag gat    870
Glu Gly Gly Glu Asp Thr Ile Glu Lys Phe Arg Ser Ala Ala Glu Asp
265                 270                 275                 280 ttc aaa gga aag gtc ctg ttt atc tac ttg gac act gac aat gag gag    918
Phe Lys Gly Lys Val Leu Phe Ile Tyr Leu Asp Thr Asp Asn Glu Glu
            285                 290                 295 aat gga cgc atc aca gag ttc ttt ggc ttg aag gat gat gaa atc cca    966
Asn Gly Arg Ile Thr Glu Phe Phe Gly Leu Lys Asp Asp Glu Ile Pro
            300                 305                 310 gct gtg cgt ctg atc cag ctg gca gag gac atg tca aag tac aag cct   1014
Ala Val Arg Leu Ile Gln Leu Ala Glu Asp Met Ser Lys Tyr Lys Pro
            315                 320                 325 gag tcc tcg gat ttg gaa act gcc acc atc aag aaa ttt gtc cag gat   1062
Glu Ser Ser Asp Leu Glu Thr Ala Thr Ile Lys Lys Phe Val Gln Asp
            330                 335                 340 ttc ctg gat ggg aaa ctg aag ccc cat ctg atg tct gag gat gtg cct   1110
Phe Leu Asp Gly Lys Leu Lys Pro His Leu Met Ser Glu Asp Val Pro
345                 350                 355                 360
```

-continued

```
ggt gac tgg gat gcc aag cct gtg aag gtc ctg gtg ggc aag aac ttc    1158
Gly Asp Trp Asp Ala Lys Pro Val Lys Val Leu Val Gly Lys Asn Phe
            365                 370                 375 aag gaa gtg gcg atg gac aaa tca aag gct gtc ttt gtg gag ttc tat    1206
Lys Glu Val Ala Met Asp Lys Ser Lys Ala Val Phe Val Glu Phe Tyr
        380                 385                 390 gct ccc tgg tgt gga cac tgc aag cag ctg gcc cct atc tgg gat gag    1254
Ala Pro Trp Cys Gly His Cys Lys Gln Leu Ala Pro Ile Trp Asp Glu
    395                 400                 405 ctg ggt gaa aag tac aag gac agc aag gac att gtt gtt gcc aag atg    1302
Leu Gly Glu Lys Tyr Lys Asp Ser Lys Asp Ile Val Val Ala Lys Met
410                 415                 420 gat gcc act gcc aat gag att gaa gag gtc aaa gtg cag agc ttc ccc    1350
Asp Ala Thr Ala Asn Glu Ile Glu Glu Val Lys Val Gln Ser Phe Pro
425                 430                 435                 440 acc ctc aag tac ttc ccc aag gac agc gag gag gct gtg gac tac aat    1398
Thr Leu Lys Tyr Phe Pro Lys Asp Ser Glu Glu Ala Val Asp Tyr Asn
            445                 450                 455 ggc gag aga acc ttg gat gct ttc gtt aaa ttc ctc gag agc ggt ggc    1446
Gly Glu Arg Thr Leu Asp Ala Phe Val Lys Phe Leu Glu Ser Gly Gly
        460                 465                 470 acg gaa ggt gct gga gtg caa gag gat gag gaa gag gaa gag gaa gat    1494
Thr Glu Gly Ala Gly Val Gln Glu Asp Glu Glu Glu Glu Glu Glu Asp
    475                 480                 485 gag gag ggt gat gat gaa gat ctg cca aga gat gaa ctg tag            1536
Glu Glu Gly Asp Asp Glu Asp Leu Pro Arg Asp Glu Leu
490                 495                 500 ctgtcatcgg catctagact cgaagggcga attccagcac actggcggcc gttactagtg   1596
gatcc                                                               1601

<210> SEQ ID NO 2
<211> LENGTH: 501
<212> TYPE: PRT
<213> ORGANISM: Conus textile

<400> SEQUENCE: 2

Met Lys Phe Ser Ser Cys Leu Val Leu Thr Leu Leu Val Phe Val Ser
1               5                   10                  15

Ala Glu Asp Val Glu Gln Glu Glu Asn Val His Val Leu Thr Lys Lys
            20                  25                  30

Asn Phe Asp Ser Phe Ile Thr Asp Asn Glu Phe Val Leu Val Glu Phe
        35                  40                  45

Tyr Ala Pro Trp Cys Gly His Cys Lys Ala Leu Ala Pro Glu Tyr Ala
    50                  55                  60

Lys Ala Thr Thr Leu Glu Asn Glu Lys Ser Asn Ile Lys Leu Ala
65                  70                  75                  80

Lys Val Asp Ala Thr Val Glu Gly Asp Leu Ala Ser Lys Phe Asp Val
                85                  90                  95

Arg Gly Tyr Pro Thr Ile Lys Phe Phe Arg Lys Glu Lys Pro Asp Gly
            100                 105                 110

Pro Ala Asp Tyr Ser Gly Gly Arg Gln Ala Lys Asp Ile Val Asp Trp
        115                 120                 125

Leu Lys Lys Lys Thr Gly Pro Pro Ala Lys Glu Leu Lys Glu Lys Asp
    130                 135                 140

Glu Val Lys Ala Phe Val Glu Lys Asp Glu Val Val Ile Gly Phe
145                 150                 155                 160

Phe Lys Asp Gln Glu Ser Thr Gly Ala Leu Ala Phe Lys Lys Ala Ala
```

```
                    165                 170                 175
Ala Gly Ile Asp Asp Ile Pro Phe Ala Ile Thr Ser Glu Asp His Val
            180                 185                 190
Phe Lys Glu Tyr Lys Met Asp Lys Asp Gly Ile Val Leu Leu Lys Lys
            195                 200                 205
Phe Asp Glu Gly Arg Asn Asp Phe Glu Gly Asn Leu Glu Glu Glu Glu
            210                 215                 220
Ala Ile Val Lys His Val Arg Glu Asn Gln Leu Pro Leu Val Val Glu
225                 230                 235                 240
Phe Thr Gln Glu Ser Ala Gln Lys Ile Phe Gly Gly Glu Val Lys Asn
                245                 250                 255
His Ile Leu Leu Phe Leu Lys Lys Glu Gly Gly Glu Asp Thr Ile Glu
                260                 265                 270
Lys Phe Arg Ser Ala Ala Glu Asp Phe Lys Gly Lys Val Leu Phe Ile
            275                 280                 285
Tyr Leu Asp Thr Asp Asn Glu Glu Asn Gly Arg Ile Thr Glu Phe Phe
        290                 295                 300
Gly Leu Lys Asp Asp Glu Ile Pro Ala Val Arg Leu Ile Gln Leu Ala
305                 310                 315                 320
Glu Asp Met Ser Lys Tyr Lys Pro Glu Ser Ser Asp Leu Glu Thr Ala
                325                 330                 335
Thr Ile Lys Lys Phe Val Gln Asp Phe Leu Asp Gly Lys Leu Lys Pro
                340                 345                 350
His Leu Met Ser Glu Asp Val Pro Gly Asp Trp Asp Ala Lys Pro Val
            355                 360                 365
Lys Val Leu Val Gly Lys Asn Phe Lys Glu Val Ala Met Asp Lys Ser
370                 375                 380
Lys Ala Val Phe Val Glu Phe Tyr Ala Pro Trp Cys Gly His Cys Lys
385                 390                 395                 400
Gln Leu Ala Pro Ile Trp Asp Glu Leu Gly Glu Lys Tyr Lys Asp Ser
                405                 410                 415
Lys Asp Ile Val Val Ala Lys Met Asp Ala Thr Ala Asn Glu Ile Glu
            420                 425                 430
Glu Val Lys Val Gln Ser Phe Pro Thr Leu Lys Tyr Phe Pro Lys Asp
            435                 440                 445
Ser Glu Glu Ala Val Asp Tyr Asn Gly Glu Arg Thr Leu Asp Ala Phe
        450                 455                 460
Val Lys Phe Leu Glu Ser Gly Thr Glu Gly Ala Gly Val Gln Glu
465                 470                 475                 480
Asp Glu Glu Glu Glu Glu Asp Glu Glu Gly Asp Glu Asp Leu
                485                 490                 495
Pro Arg Asp Glu Leu
            500

<210> SEQ ID NO 3
<211> LENGTH: 2574
<212> TYPE: DNA
<213> ORGANISM: Conus textile
<220> FEATURE:
<221> NAME/KEY: CDS
<222> LOCATION: (138)..(1643)
<223> OTHER INFORMATION: An isoform of the Protein Disulfide Isomerase
      isolated from Conus textile.
<220> FEATURE:
<221> NAME/KEY: misc_feature
<222> LOCATION: (2353)..(2353)
<223> OTHER INFORMATION: n is any nucleic acid
```

<220> FEATURE:
<221> NAME/KEY: misc_feature
<222> LOCATION: (2402)..(2402)
<223> OTHER INFORMATION: n is any nucleic acid

<400> SEQUENCE: 3

| | |
|---|---|
| gaattcgccc tttggcgatg aatgaacact gcgtttgctg gctttgatga aaacttgtag | 60 |
| gcctaccggt gccacgttga gtgaaaatcc ttttgctcgc aatctctccc acgagttaca | 120 |

| | | |
|---|---|---|
| tagcagtccg catcatc atg aag ttt tca tct tgt tta gtt tta act ctt<br>                   Met Lys Phe Ser Ser Cys Leu Val Leu Thr Leu<br>                   1             5                10 | 170 |
| ctg gtt ttt gta tca gcc gaa gat gtc aaa cgg gag gaa ggt gtc tac<br>Leu Val Phe Val Ser Ala Glu Asp Val Lys Arg Glu Glu Gly Val Tyr<br>             15                20              25 | 218 |
| gtt ttg acg gag aaa aat ttt gac gcc ttc ata act gat aat gag ttc<br>Val Leu Thr Glu Lys Asn Phe Asp Ala Phe Ile Thr Asp Asn Glu Phe<br>      30                35              40 | 266 |
| gtg ctt gtg gaa ttt tat gct ccc tgg tgt ggc cat tgc aag gca ttg<br>Val Leu Val Glu Phe Tyr Ala Pro Trp Cys Gly His Cys Lys Ala Leu<br>45                50              55 | 314 |
| gca cca gaa tat gcc aaa gct gca aca act ttg gag gaa gag aag tcg<br>Ala Pro Glu Tyr Ala Lys Ala Ala Thr Thr Leu Glu Glu Glu Lys Ser<br>60                65              70              75 | 362 |
| aac atc aag ttg ggc aaa gtg gat gct act gtg gag gtg aac ttg gcc<br>Asn Ile Lys Leu Gly Lys Val Asp Ala Thr Val Glu Val Asn Leu Ala<br>             80                85              90 | 410 |
| acc aaa ttc gaa gtt cgt gga tac cca aca atc aag ttc ttc cat aaa<br>Thr Lys Phe Glu Val Arg Gly Tyr Pro Thr Ile Lys Phe Phe His Lys<br>          95                100            105 | 458 |
| gag atg cct gct ggc agt cca gca gac tac agt ggt ggt cgc caa gct<br>Glu Met Pro Ala Gly Ser Pro Ala Asp Tyr Ser Gly Gly Arg Gln Ala<br>             110                115            120 | 506 |
| cca gat att gtt ggc tgg ctg aag aag aag aca gga cca cca gcc aag<br>Pro Asp Ile Val Gly Trp Leu Lys Lys Lys Thr Gly Pro Pro Ala Lys<br>125                130              135 | 554 |
| gaa ctg aag gcg aaa gat gaa gtc aag act ttt gtg gaa aaa gat gaa<br>Glu Leu Lys Ala Lys Asp Glu Val Lys Thr Phe Val Glu Lys Asp Glu<br>140                145              150            155 | 602 |
| gtt gtt gtc att ggt ttc ttc aag gat caa gaa tcc aca ggt gct ttg<br>Val Val Val Ile Gly Phe Phe Lys Asp Gln Glu Ser Thr Gly Ala Leu<br>             160                165            170 | 650 |
| gcc ttc aaa aag gca gct gcc ggc att gat gac att cca ttt gcc atc<br>Ala Phe Lys Lys Ala Ala Ala Gly Ile Asp Asp Ile Pro Phe Ala Ile<br>             175                180            185 | 698 |
| act tca gag gat cat gtt ttc aag gag tac aag atg gac aaa gat ggc<br>Thr Ser Glu Asp His Val Phe Lys Glu Tyr Lys Met Asp Lys Asp Gly<br>             190                195            200 | 746 |
| att gta ctg ctg aag aag ttt gat gag ggc cgt aat gac ttc gag ggg<br>Ile Val Leu Leu Lys Lys Phe Asp Glu Gly Arg Asn Asp Phe Glu Gly<br>             205                210            215 | 794 |
| aat ttg gag gag gag gag gcc atc gtc aag cac gtc agg gaa aac caa<br>Asn Leu Glu Glu Glu Glu Ala Ile Val Lys His Val Arg Glu Asn Gln<br>220                225              230            235 | 842 |
| ctg cca ctg gtt gta gag ttc act caa gag tct gcc cag aag atc ttt<br>Leu Pro Leu Val Val Glu Phe Thr Gln Glu Ser Ala Gln Lys Ile Phe<br>             240                245            250 | 890 |
| gga ggt gag gtg aag aac cac att ctg ctg ttc ctg aag aag gac ggt<br>Gly Gly Glu Val Lys Asn His Ile Leu Leu Phe Leu Lys Lys Asp Gly<br>             255                260            265 | 938 |

-continued

| | | |
|---|---|---|
| gga gaa gac aca att gaa aag ttc aga ggt gca gct gag gac ttc aaa<br>Gly Glu Asp Thr Ile Glu Lys Phe Arg Gly Ala Ala Glu Asp Phe Lys<br>270                275                  280 | 986 |
| gga aag gtc ctg ttt atc tac ttg gac act gac aat gag gag aat gga<br>Gly Lys Val Leu Phe Ile Tyr Leu Asp Thr Asp Asn Glu Glu Asn Gly<br>285                290              295 | 1034 |
| cgc atc aca gag ttc ttt ggc ttg aag gat gat gaa atc cca gct gtg<br>Arg Ile Thr Glu Phe Phe Gly Leu Lys Asp Asp Glu Ile Pro Ala Val<br>300                305              310              315 | 1082 |
| cgt ctg atc cag ctg gca gag gac atg tca aag tac aag cct gag tcc<br>Arg Leu Ile Gln Leu Ala Glu Asp Met Ser Lys Tyr Lys Pro Glu Ser<br>320                325              330 | 1130 |
| tcg gat ttg gaa act gcc acc atc aag aaa ttt gtc cag gat ttc ctg<br>Ser Asp Leu Glu Thr Ala Thr Ile Lys Lys Phe Val Gln Asp Phe Leu<br>335                340              345 | 1178 |
| gat ggg aaa ctg aag ccc cat ctg atg tct gag gat gtg cct ggt gac<br>Asp Gly Lys Leu Lys Pro His Leu Met Ser Glu Asp Val Pro Gly Asp<br>350                355              360 | 1226 |
| tgg gat gcc aag cct gtg aag gtc ctg gtg ggc aag aac ttc aag gaa<br>Trp Asp Ala Lys Pro Val Lys Val Leu Val Gly Lys Asn Phe Lys Glu<br>365                370              375 | 1274 |
| gtg gcg atg gac aaa tca aag gct gtc ttt gtg gag ttc tat gct ccc<br>Val Ala Met Asp Lys Ser Lys Ala Val Phe Val Glu Phe Tyr Ala Pro<br>380                385              390              395 | 1322 |
| tgg tgt gga cac tgc aag cag ctg gcc cct atc tgg gat gag ctg ggt<br>Trp Cys Gly His Cys Lys Gln Leu Ala Pro Ile Trp Asp Glu Leu Gly<br>400                405              410 | 1370 |
| gaa aag tac aag gac agc aag gac att gtt gtt gcc aag atg gat gcc<br>Glu Lys Tyr Lys Asp Ser Lys Asp Ile Val Val Ala Lys Met Asp Ala<br>415                420              425 | 1418 |
| act gcc aat gag att gaa gag gtc aaa gtg cag agc ttc ccc acc ctc<br>Thr Ala Asn Glu Ile Glu Glu Val Lys Val Gln Ser Phe Pro Thr Leu<br>430                435              440 | 1466 |
| aag tac ttc ccc aag gac agc gag gag gct gtg gac tac aat ggc gag<br>Lys Tyr Phe Pro Lys Asp Ser Glu Glu Ala Val Asp Tyr Asn Gly Glu<br>445                450              455 | 1514 |
| aga acc ttg gat gct ttt gtc aaa ttc ctc gag agc ggt ggc acg gaa<br>Arg Thr Leu Asp Ala Phe Val Lys Phe Leu Glu Ser Gly Gly Thr Glu<br>460                465              470              475 | 1562 |
| ggt gct gga gtg caa gag gat gag gaa gag gaa gag gaa gat gag gag<br>Gly Ala Gly Val Gln Glu Asp Glu Glu Glu Glu Glu Glu Asp Glu Glu<br>480                485              490 | 1610 |
| ggt gat gat gaa gat ctg cca aga gat gaa ctg tagctgtcat cggcatcaaa<br>Gly Asp Asp Glu Asp Leu Pro Arg Asp Glu Leu<br>495                500 | 1663 |
| tttccctgta tcttgtctga tcagtatcat cttcatccct ctttctttct gtcattgttt | 1723 |
| cttctctttt gtctgactgc atatgtgttc ttttattgtg catttgatcc ccttttctc | 1783 |
| tcatgggatg attgaagatt tgcaagtcgt gttgattaga aaactttgaa tggagagaga | 1843 |
| tgtgaaatta taagactgaa ccgagtttgt ttgcagagta tgtgttgttg acattgcata | 1903 |
| catgcggaat ggatctttta gtaattttt ttgttttagt ttctgcttca tgaatgatgt | 1963 |
| ctatattttt agacactttt gcatttgtg gtgccgtttt cttttttttt ttttttcttt | 2023 |
| ttctttttaa tgcatttttc catgttgatt tttcctttgt tattttttt ggactgtctt | 2083 |
| gcccccagaa ataacagggt gtgagttgct gattatatga aattttaagg tgaaatgttt | 2143 |
| agagtatatg tgaaatttag atatactttt tacattttc caaaaaaaaa aagcaaaaaa | 2203 |
| ctgttgaatc aagtttataa ttgttattgc ttgattaatg caataataat tgttaaagaa | 2263 |

```
aagcagtgtt tccatgtaca cttacatagt agagatttat gttttgtttt catgtccatg    2323
gtttgttttg tttgttttg tttcattccn cagattcaaa atgtagcctt ttgactgtca    2383
gacttcctgg ctgattatnt agctcatggg agggattgaa ctaaaaacat acaaaattgc    2443
tgatagttgc aaatcatgtg cttgtgacaa gttcaggatt aaccaggaat taaaaccatt    2503
catccttgtg taaagaaaaa aaaaaaaaaa aaaagtactc tgcgttgtta ctcgagctta    2563
agggcgaatt c                                                        2574
```

<210> SEQ ID NO 4
<211> LENGTH: 502
<212> TYPE: PRT
<213> ORGANISM: Conus textile

<400> SEQUENCE: 4

```
Met Lys Phe Ser Ser Cys Leu Val Leu Thr Leu Leu Val Phe Val Ser
1               5                   10                  15

Ala Glu Asp Val Lys Arg Glu Glu Gly Val Tyr Val Leu Thr Glu Lys
                20                  25                  30

Asn Phe Asp Ala Phe Ile Thr Asp Asn Glu Phe Val Leu Val Glu Phe
            35                  40                  45

Tyr Ala Pro Trp Cys Gly His Cys Lys Ala Leu Ala Pro Glu Tyr Ala
        50                  55                  60

Lys Ala Ala Thr Thr Leu Glu Glu Lys Ser Asn Ile Lys Leu Gly
65                  70                  75                  80

Lys Val Asp Ala Thr Val Glu Val Asn Leu Ala Thr Lys Phe Glu Val
                85                  90                  95

Arg Gly Tyr Pro Thr Ile Lys Phe Phe His Lys Glu Met Pro Ala Gly
            100                 105                 110

Ser Pro Ala Asp Tyr Ser Gly Gly Arg Gln Ala Pro Asp Ile Val Gly
        115                 120                 125

Trp Leu Lys Lys Lys Thr Gly Pro Pro Ala Lys Glu Leu Lys Ala Lys
    130                 135                 140

Asp Glu Val Lys Thr Phe Val Glu Lys Asp Val Val Val Ile Gly
145                 150                 155                 160

Phe Phe Lys Asp Gln Glu Ser Thr Gly Ala Leu Ala Phe Lys Lys Ala
                165                 170                 175

Ala Ala Gly Ile Asp Asp Ile Pro Phe Ala Ile Thr Ser Glu Asp His
            180                 185                 190

Val Phe Lys Glu Tyr Lys Met Asp Lys Asp Gly Ile Val Leu Leu Lys
        195                 200                 205

Lys Phe Asp Glu Gly Arg Asn Asp Phe Glu Gly Asn Leu Glu Glu Glu
    210                 215                 220

Glu Ala Ile Val Lys His Val Arg Glu Asn Gln Leu Pro Leu Val Val
225                 230                 235                 240

Glu Phe Thr Gln Glu Ser Ala Gln Lys Ile Phe Gly Gly Glu Val Lys
                245                 250                 255

Asn His Ile Leu Leu Phe Leu Lys Lys Asp Gly Gly Glu Asp Thr Ile
            260                 265                 270

Glu Lys Phe Arg Gly Ala Ala Glu Asp Phe Lys Gly Lys Val Leu Phe
        275                 280                 285

Ile Tyr Leu Asp Thr Asp Asn Glu Glu Asn Gly Arg Ile Thr Glu Phe
    290                 295                 300

Phe Gly Leu Lys Asp Asp Glu Ile Pro Ala Val Arg Leu Ile Gln Leu
```

```
                305                 310                 315                 320
Ala Glu Asp Met Ser Lys Tyr Lys Pro Glu Ser Ser Asp Leu Glu Thr
                    325                 330                 335

Ala Thr Ile Lys Lys Phe Val Gln Asp Phe Leu Asp Gly Lys Leu Lys
                340                 345                 350

Pro His Leu Met Ser Glu Asp Val Pro Gly Asp Trp Asp Ala Lys Pro
            355                 360                 365

Val Lys Val Leu Val Gly Lys Asn Phe Lys Glu Val Ala Met Asp Lys
        370                 375                 380

Ser Lys Ala Val Phe Val Glu Phe Tyr Ala Pro Trp Cys Gly His Cys
385                 390                 395                 400

Lys Gln Leu Ala Pro Ile Trp Asp Glu Leu Gly Glu Lys Tyr Lys Asp
                405                 410                 415

Ser Lys Asp Ile Val Val Ala Lys Met Asp Ala Thr Ala Asn Glu Ile
                420                 425                 430

Glu Glu Val Lys Val Gln Ser Phe Pro Thr Leu Lys Tyr Phe Pro Lys
            435                 440                 445

Asp Ser Glu Glu Ala Val Asp Tyr Asn Gly Arg Thr Leu Asp Ala
    450                 455                 460

Phe Val Lys Phe Leu Glu Ser Gly Gly Thr Glu Gly Ala Gly Val Gln
465                 470                 475                 480

Glu Asp Glu Glu Glu Glu Glu Asp Glu Glu Gly Asp Asp Glu Asp
                485                 490                 495

Leu Pro Arg Asp Glu Leu
            500

<210> SEQ ID NO 5
<211> LENGTH: 1994
<212> TYPE: DNA
<213> ORGANISM: Conus textile
<220> FEATURE:
<221> NAME/KEY: CDS
<222> LOCATION: (31)..(1536)
<223> OTHER INFORMATION: Tex2, an isoform of the Protein Disulfide
      Isomerase identified in C. textile
<220> FEATURE:
<221> NAME/KEY: misc_feature
<222> LOCATION: (1927)..(1927)
<223> OTHER INFORMATION: n is any nucleic acid
<220> FEATURE:
<221> NAME/KEY: misc_feature
<222> LOCATION: (1941)..(1941)
<223> OTHER INFORMATION: n is any nucleic acid
<220> FEATURE:
<221> NAME/KEY: misc_feature
<222> LOCATION: (1943)..(1943)
<223> OTHER INFORMATION: n is any nucleic acid
<220> FEATURE:
<221> NAME/KEY: misc_feature
<222> LOCATION: (1989)..(1989)
<223> OTHER INFORMATION: n is any nucleic acid
<220> FEATURE:
<221> NAME/KEY: misc_feature
<222> LOCATION: (1991)..(1991)
<223> OTHER INFORMATION: n is any nucleic acid
<220> FEATURE:
<221> NAME/KEY: misc_feature
<222> LOCATION: (1994)..(1994)
<223> OTHER INFORMATION: n is any nucleic acid

<400> SEQUENCE: 5
gaattcgccc ttactaggat ccgcatcatc atg aag ttt cca tct tgt tta gtt    54
                                Met Lys Phe Pro Ser Cys Leu Val
                                1               5
```

-continued

| | | |
|---|---|---|
| tta act ctt ctg gtt ttt gta tca gcc gaa gat gtc aaa cag gag gaa<br>Leu Thr Leu Leu Val Phe Val Ser Ala Glu Asp Val Lys Gln Glu Glu<br>    10                              15                      20 | 102 |
| ggt gtc tac gtt ttg acg gag aaa aat ttt ggc gcc ttc ata tct gat<br>Gly Val Tyr Val Leu Thr Glu Lys Asn Phe Gly Ala Phe Ile Ser Asp<br>25                      30                        35                        40 | 150 |
| aat gag ttc gtg ctt gtg gaa ttt tat gct ccc tgg tgt ggc cat tgc<br>Asn Glu Phe Val Leu Val Glu Phe Tyr Ala Pro Trp Cys Gly His Cys<br>                        45                        50                        55 | 198 |
| aag gca ttg gca cca gaa tat gcc aaa gct gca aca acc ttg gag gaa<br>Lys Ala Leu Ala Pro Glu Tyr Ala Lys Ala Ala Thr Thr Leu Glu Glu<br>                60                        65                              70 | 246 |
| gag aag tcg aac atc aag ttg ggc aaa gtg gat gct act gtg gag gtg<br>Glu Lys Ser Asn Ile Lys Leu Gly Lys Val Asp Ala Thr Val Glu Val<br>      75                        80                        85 | 294 |
| aac ttg gcc acc aaa ttc gaa gtt cgt gga tac cca aca atc aag ttc<br>Asn Leu Ala Thr Lys Phe Glu Val Arg Gly Tyr Pro Thr Ile Lys Phe<br>    90                        95                        100 | 342 |
| ttc cat aaa gag atg cct gct ggc agt cca gca gac tac agt ggt ggt<br>Phe His Lys Glu Met Pro Ala Gly Ser Pro Ala Asp Tyr Ser Gly Gly<br>105                      110                       115                      120 | 390 |
| cgc caa gct cca gat att gtt ggc tgg ctg aag aag aag aca gga cca<br>Arg Gln Ala Pro Asp Ile Val Gly Trp Leu Lys Lys Lys Thr Gly Pro<br>                      125                        130                      135 | 438 |
| cca gcc aag gaa ctg aag gcg aaa gat gaa gtc aag act ttt gtg gaa<br>Pro Ala Lys Glu Leu Lys Ala Lys Asp Glu Val Lys Thr Phe Val Glu<br>                140                        145                        150 | 486 |
| aaa gat gaa gtt gtt gtc att ggt ttc ttc aag gat caa gaa tcc aca<br>Lys Asp Glu Val Val Val Ile Gly Phe Phe Lys Asp Gln Glu Ser Thr<br>            155                        160                        165 | 534 |
| ggt gct ttg gcc ttc aaa aag gca gct gcc ggc att gat gac att cca<br>Gly Ala Leu Ala Phe Lys Lys Ala Ala Ala Gly Ile Asp Asp Ile Pro<br>    170                        175                        180 | 582 |
| ttt gcc atc act tca gag gat cat gtt ttc aag gag tac aag atg gac<br>Phe Ala Ile Thr Ser Glu Asp His Val Phe Lys Glu Tyr Lys Met Asp<br>185                      190                       195                      200 | 630 |
| aaa gat ggc att gta ctg ctg aag aag ttt gat gag ggc cgt aat gac<br>Lys Asp Gly Ile Val Leu Leu Lys Lys Phe Asp Glu Gly Arg Asn Asp<br>                      205                        210                      215 | 678 |
| ttc gag ggg aat ttg gag gag gag gag gcc atc gtc aag cac gtc agg<br>Phe Glu Gly Asn Leu Glu Glu Glu Glu Ala Ile Val Lys His Val Arg<br>                220                        225                      230 | 726 |
| gaa aac caa ctg cca ctg gtt gta gag ttc act caa gag tct gcc cag<br>Glu Asn Gln Leu Pro Leu Val Val Glu Phe Thr Gln Glu Ser Ala Gln<br>                235                        240                      245 | 774 |
| aag atc ttt gga ggt gag gtg aag aac cac att ctg ctg ttc ctg aag<br>Lys Ile Phe Gly Gly Glu Val Lys Asn His Ile Leu Leu Phe Leu Lys<br>    250                        255                        260 | 822 |
| aag gaa ggt gga gaa gac aca att gaa aag ttc aga ggt gca gct gag<br>Lys Glu Gly Gly Glu Asp Thr Ile Glu Lys Phe Arg Gly Ala Ala Glu<br>265                      270                       275                      280 | 870 |
| gat ttc aaa gga aag gtc ctg ttt atc tac ttg gac act gac aat gag<br>Asp Phe Lys Gly Lys Val Leu Phe Ile Tyr Leu Asp Thr Asp Asn Glu<br>                      285                        290                      295 | 918 |
| gag aat gga cgt atc aca gag ttc ttt ggc ttg aag gat gat gaa atc<br>Glu Asn Gly Arg Ile Thr Glu Phe Phe Gly Leu Lys Asp Asp Glu Ile<br>                300                        305                      310 | 966 |
| cca gct gtg cgt ctc atc cag ctg gca gag gac atg tca aag tac aag<br>Pro Ala Val Arg Leu Ile Gln Leu Ala Glu Asp Met Ser Lys Tyr Lys<br>    315                        320                        325 | 1014 |

-continued

```
ccc gag tcc tcg gat ttg gaa act gcc acc atc aag aaa ttt gtc cag      1062
Pro Glu Ser Ser Asp Leu Glu Thr Ala Thr Ile Lys Lys Phe Val Gln
        330                 335                 340 gat ttc ctg gat ggg aaa ctg aag ccc cat ctg atg tct gag gat gtg      1110
Asp Phe Leu Asp Gly Lys Leu Lys Pro His Leu Met Ser Glu Asp Val
345                 350                 355                 360 cct ggt gac tgg gat gcc aag cct gtg aag gtc ctg gtg ggc aag aac      1158
Pro Gly Asp Trp Asp Ala Lys Pro Val Lys Val Leu Val Gly Lys Asn
                365                 370                 375 ttc aag gaa gtg gcg atg gac aaa tca aag gct gtc ttt gtg gag ttc      1206
Phe Lys Glu Val Ala Met Asp Lys Ser Lys Ala Val Phe Val Glu Phe
            380                 385                 390 tat gct ccc tgg tgt gga cac tgc aag cag ctg gcc cct atc tgg gat      1254
Tyr Ala Pro Trp Cys Gly His Cys Lys Gln Leu Ala Pro Ile Trp Asp
        395                 400                 405 gag ctg ggt gaa aag tac aag gac agc aag gac att gtt gtt gcc aag      1302
Glu Leu Gly Glu Lys Tyr Lys Asp Ser Lys Asp Ile Val Val Ala Lys
    410                 415                 420 atg gat gcc act gcc aat gag att gaa gag gtc aaa gtg cag agc ttc      1350
Met Asp Ala Thr Ala Asn Glu Ile Glu Glu Val Lys Val Gln Ser Phe
425                 430                 435                 440 ccc acc ctc aag tac ttc ccc aag gac agc gat gag gct gtg gac tac      1398
Pro Thr Leu Lys Tyr Phe Pro Lys Asp Ser Asp Glu Ala Val Asp Tyr
                445                 450                 455 aat ggc gag aga acc ttg gat gct ttc gtc aaa ttc ctc gag agc ggt      1446
Asn Gly Glu Arg Thr Leu Asp Ala Phe Val Lys Phe Leu Glu Ser Gly
            460                 465                 470 ggc acg gaa ggt gct gga gtg caa gag gat gag gaa gag gaa gag gaa      1494
Gly Thr Glu Gly Ala Gly Val Gln Glu Asp Glu Glu Glu Glu Glu Glu
        475                 480                 485 gat gag gag ggt gat gat gaa gat ctg cca aga gat gaa ctg                1536
Asp Glu Glu Gly Asp Asp Glu Asp Leu Pro Arg Asp Glu Leu
    490                 495                 500 tagctgtcat cggcatctag actcgaaggg cgaattccag cacactggcg gccgttacta    1596
gtggatccga gctcggtacc aagcttggcg taatcatggt catagctgtt tcctgtgtga    1656
aattgttatc cgctcacaat tccacacaac atacgagccg aagcataaa gtgtaaagcc     1716 tggggtgcct aatgagtgag ctaactcaca ttaattgcgt tgcgctcact gcccgctttc    1776
cagtcgggaa acctgtcgtg ccagctgcat taatgaatcg gccaacgcgc ggggagagg     1836 cggtttgcgt attgggcgct cttccgcttc ctcgctcact gactcgctgc gctcggtcgt    1896
tcggctgcgg cgagcggtat cagctcactc naaggcggta atacngntat ccacagaatc    1956
aggggataac gcaggaaaga catgtgagca aangncan                            1994
```

<210> SEQ ID NO 6
<211> LENGTH: 502
<212> TYPE: PRT
<213> ORGANISM: Conus textile

<400> SEQUENCE: 6

```
Met Lys Phe Pro Ser Cys Leu Val Leu Thr Leu Leu Val Phe Val Ser
1               5                   10                  15

Ala Glu Asp Val Lys Gln Glu Glu Gly Val Tyr Val Leu Thr Glu Lys
                20                  25                  30

Asn Phe Gly Ala Phe Ile Ser Asp Asn Glu Phe Val Leu Val Glu Phe
            35                  40                  45

Tyr Ala Pro Trp Cys Gly His Cys Lys Ala Leu Ala Pro Glu Tyr Ala
```

```
              50                  55                  60
Lys Ala Ala Thr Thr Leu Glu Glu Lys Ser Asn Ile Lys Leu Gly
 65                  70                  75                  80

Lys Val Asp Ala Thr Val Glu Val Asn Leu Ala Thr Lys Phe Glu Val
                     85                  90                  95

Arg Gly Tyr Pro Thr Ile Lys Phe Phe His Lys Glu Met Pro Ala Gly
                100                 105                 110

Ser Pro Ala Asp Tyr Ser Gly Gly Arg Gln Ala Pro Asp Ile Val Gly
                115                 120                 125

Trp Leu Lys Lys Thr Gly Pro Ala Lys Glu Leu Lys Ala Lys
                130                 135                 140

Asp Glu Val Lys Thr Phe Val Glu Lys Asp Glu Val Val Ile Gly
145                 150                 155                 160

Phe Phe Lys Asp Gln Glu Ser Thr Gly Ala Leu Ala Phe Lys Lys Ala
                    165                 170                 175

Ala Ala Gly Ile Asp Asp Ile Pro Phe Ala Ile Thr Ser Glu Asp His
                180                 185                 190

Val Phe Lys Glu Tyr Lys Met Asp Lys Asp Gly Ile Val Leu Leu Lys
                195                 200                 205

Lys Phe Asp Glu Gly Arg Asn Asp Phe Glu Gly Asn Leu Glu Glu Glu
                210                 215                 220

Glu Ala Ile Val Lys His Val Arg Glu Asn Gln Leu Pro Leu Val Val
225                 230                 235                 240

Glu Phe Thr Gln Glu Ser Ala Gln Lys Ile Phe Gly Gly Glu Val Lys
                245                 250                 255

Asn His Ile Leu Leu Phe Leu Lys Lys Glu Gly Gly Glu Asp Thr Ile
                260                 265                 270

Glu Lys Phe Arg Gly Ala Ala Glu Asp Phe Lys Gly Lys Val Leu Phe
                275                 280                 285

Ile Tyr Leu Asp Thr Asp Asn Glu Glu Asn Gly Arg Ile Thr Glu Phe
                290                 295                 300

Phe Gly Leu Lys Asp Asp Glu Ile Pro Ala Val Arg Leu Ile Gln Leu
305                 310                 315                 320

Ala Glu Asp Met Ser Lys Tyr Lys Pro Glu Ser Ser Asp Leu Glu Thr
                325                 330                 335

Ala Thr Ile Lys Lys Phe Val Gln Asp Phe Leu Asp Gly Lys Leu Lys
                340                 345                 350

Pro His Leu Met Ser Glu Asp Val Pro Gly Asp Trp Asp Ala Lys Pro
                355                 360                 365

Val Lys Val Leu Val Gly Lys Asn Phe Lys Glu Val Ala Met Asp Lys
                370                 375                 380

Ser Lys Ala Val Phe Val Glu Phe Tyr Ala Pro Trp Cys Gly His Cys
385                 390                 395                 400

Lys Gln Leu Ala Pro Ile Trp Asp Glu Leu Gly Glu Lys Tyr Lys Asp
                    405                 410                 415

Ser Lys Asp Ile Val Val Ala Lys Met Asp Ala Thr Ala Asn Glu Ile
                420                 425                 430

Glu Glu Val Lys Val Gln Ser Phe Pro Thr Leu Lys Tyr Phe Pro Lys
                435                 440                 445

Asp Ser Asp Glu Ala Val Asp Tyr Asn Gly Glu Arg Thr Leu Asp Ala
                450                 455                 460

Phe Val Lys Phe Leu Glu Ser Gly Gly Thr Glu Gly Ala Gly Val Gln
465                 470                 475                 480
```

```
Glu Asp Glu Glu Glu Glu Glu Asp Glu Glu Gly Asp Asp Glu Asp
                485                 490                 495

Leu Pro Arg Asp Glu Leu
            500

<210> SEQ ID NO 7
<211> LENGTH: 1993
<212> TYPE: DNA
<213> ORGANISM: Conus textile
<220> FEATURE:
<221> NAME/KEY: CDS
<222> LOCATION: (31)..(1536)
<223> OTHER INFORMATION: Isoform of the Protein Disulfide Isomerase
      isolated from C. textile
<220> FEATURE:
<221> NAME/KEY: misc_feature
<222> LOCATION: (505)..(505)
<223> OTHER INFORMATION: n is any nucleic acid
<220> FEATURE:
<221> NAME/KEY: misc_feature
<222> LOCATION: (1768)..(1768)
<223> OTHER INFORMATION: n is any nucleic acid
<220> FEATURE:
<221> NAME/KEY: misc_feature
<222> LOCATION: (1788)..(1788)
<223> OTHER INFORMATION: n is any nucleic acid
<220> FEATURE:
<221> NAME/KEY: misc_feature
<222> LOCATION: (1930)..(1930)
<223> OTHER INFORMATION: n is any nucleic acid
<220> FEATURE:
<221> NAME/KEY: misc_feature
<222> LOCATION: (1945)..(1945)
<223> OTHER INFORMATION: n is any nucleic acid
<220> FEATURE:
<221> NAME/KEY: misc_feature
<222> LOCATION: (1952)..(1952)
<223> OTHER INFORMATION: n is any nucleic acid
<220> FEATURE:
<221> NAME/KEY: misc_feature
<222> LOCATION: (1974)..(1974)
<223> OTHER INFORMATION: n is any nucleic acid
<220> FEATURE:
<221> NAME/KEY: misc_feature
<222> LOCATION: (1977)..(1977)
<223> OTHER INFORMATION: n is any nucleic acid
<220> FEATURE:
<221> NAME/KEY: misc_feature
<222> LOCATION: (1988)..(1988)
<223> OTHER INFORMATION: n is any nucleic acid
<220> FEATURE:
<221> NAME/KEY: misc_feature
<222> LOCATION: (1990)..(1990)
<223> OTHER INFORMATION: n is any nucleic acid
<220> FEATURE:
<221> NAME/KEY: misc_feature
<222> LOCATION: (1993)..(1993)
<223> OTHER INFORMATION: n is any nucleic acid

<400> SEQUENCE: 7
gaattcgccc ttactaggat ccgcatcatc atg aag ttt tca tct tgt tta gtt      54
                                 Met Lys Phe Ser Ser Cys Leu Val
                                  1               5 tta act ctt ctg gtt ttt gta tca gcc gaa gat gtc aaa cag gag gaa      102
Leu Thr Leu Leu Val Phe Val Ser Ala Glu Asp Val Lys Gln Glu Glu
    10                  15                  20 ggt gtc tac gtt ttg acg gag aaa aat ttt gac gcc ttc ata tct gat      150
Gly Val Tyr Val Leu Thr Glu Lys Asn Phe Asp Ala Phe Ile Ser Asp
25                  30                  35                  40 aat gag ttc gtg ctt gtg gaa ttt tat gct ccc tgg tgt ggc cat tgc      198
Asn Glu Phe Val Leu Val Glu Phe Tyr Ala Pro Trp Cys Gly His Cys
                45                  50                  55
```

```
aag gca ttg gca cca gaa tat gcc aaa gct gca aca act ttg gag gaa      246
Lys Ala Leu Ala Pro Glu Tyr Ala Lys Ala Ala Thr Thr Leu Glu Glu
             60                  65                  70 gag aag tcg aac atc aag ttg ggc aaa gtg gat gct act gtg gag gtg      294
Glu Lys Ser Asn Ile Lys Leu Gly Lys Val Asp Ala Thr Val Glu Val
         75                  80                  85 aac ttg gcc acc aaa ttc gaa gtt cgt gga tac cca aca atc aag ttc      342
Asn Leu Ala Thr Lys Phe Glu Val Arg Gly Tyr Pro Thr Ile Lys Phe
     90                  95                 100 ttc cat aaa gag atg cct gct ggc agt cca gca gac tac agt ggt ggt      390
Phe His Lys Glu Met Pro Ala Gly Ser Pro Ala Asp Tyr Ser Gly Gly
105                 110                 115                 120 cgc caa gct cca gat att gtt ggc tgg ctg aag aag aag aca gga cca      438
Arg Gln Ala Pro Asp Ile Val Gly Trp Leu Lys Lys Lys Thr Gly Pro
                125                 130                 135 cca gcc aag gaa ctg aag gcg aaa gat gaa gtc aag act ttt gtg gaa      486
Pro Ala Lys Glu Leu Lys Ala Lys Asp Glu Val Lys Thr Phe Val Glu
            140                 145                 150 aaa gat gaa gtt gtt gtc ntt ggt ttc ttc aag gat caa gaa tcc aca      534
Lys Asp Glu Val Val Val Xaa Gly Phe Phe Lys Asp Gln Glu Ser Thr
        155                 160                 165 ggt gct ttg gcc ttc aaa aag gca gct gcc ggc att gat gac att cca      582
Gly Ala Leu Ala Phe Lys Lys Ala Ala Ala Gly Ile Asp Asp Ile Pro
    170                 175                 180 ttt gcc atc act tca gag gat cat gtt ttc aag gag tac aag atg gac      630
Phe Ala Ile Thr Ser Glu Asp His Val Phe Lys Glu Tyr Lys Met Asp
185                 190                 195                 200 aaa gat ggc att gta ctg ctg aag aag ttt gat gag ggc cgt aat gac      678
Lys Asp Gly Ile Val Leu Leu Lys Lys Phe Asp Glu Gly Arg Asn Asp
                205                 210                 215 ttc gag ggg aat ttg gag gag gag gag gcc atc gtc aag cac gtc agg      726
Phe Glu Gly Asn Leu Glu Glu Glu Glu Ala Ile Val Lys His Val Arg
            220                 225                 230 gaa aac caa ctg cca ctg gtt gta gag ttc act caa gag tct gcc cag      774
Glu Asn Gln Leu Pro Leu Val Val Glu Phe Thr Gln Glu Ser Ala Gln
        235                 240                 245 aag atc ttt gga ggt gag gtg aag aac cac att ctg ctg ttc ctg aag      822
Lys Ile Phe Gly Gly Glu Val Lys Asn His Ile Leu Leu Phe Leu Lys
    250                 255                 260 aag gaa ggt gga gaa gac aca att gaa aag ttc aga ggt gca gct gag      870
Lys Glu Gly Gly Glu Asp Thr Ile Glu Lys Phe Arg Gly Ala Ala Glu
265                 270                 275                 280 gat ttc aaa gga aag gtc ctg ttt atc tac ttg gac act gac aat gag      918
Asp Phe Lys Gly Lys Val Leu Phe Ile Tyr Leu Asp Thr Asp Asn Glu
                285                 290                 295 gag aat gga cgt atc aca gag ttc ttt ggc ttg aag gat gat gaa atc      966
Glu Asn Gly Arg Ile Thr Glu Phe Phe Gly Leu Lys Asp Asp Glu Ile
            300                 305                 310 cca gct gtg cgt ctc atc cag ctg gca gag gac atg tca aag tac aag     1014
Pro Ala Val Arg Leu Ile Gln Leu Ala Glu Asp Met Ser Lys Tyr Lys
        315                 320                 325 ccc gag tcc tcg gat ttg gaa act gcc acc atc aag aaa ttt gtc cag     1062
Pro Glu Ser Ser Asp Leu Glu Thr Ala Thr Ile Lys Lys Phe Val Gln
    330                 335                 340 gat ttc ctg gat ggg aaa ctg aag ccc cat ctg atg tct gag gat gtg     1110
Asp Phe Leu Asp Gly Lys Leu Lys Pro His Leu Met Ser Glu Asp Val
345                 350                 355                 360 cct ggt gac tgg gat gcc aag cct gtg aag gtc ctg gtg ggc aag aac     1158
Pro Gly Asp Trp Asp Ala Lys Pro Val Lys Val Leu Val Gly Lys Asn
```

```
                  365                 370                 375
ttc aag gaa gtg gcg atg gac aaa tca aag gct gtc ttt gtg gag ttc    1206
Phe Lys Glu Val Ala Met Asp Lys Ser Lys Ala Val Phe Val Glu Phe
            380                 385                 390 tat gct ccc tgg tgt gga cac tgc aag cag ctg gcc cct atc tgg gat    1254
Tyr Ala Pro Trp Cys Gly His Cys Lys Gln Leu Ala Pro Ile Trp Asp
        395                 400                 405 gag ctg ggt gaa aag tac aag gac agc aag gac att gtt gtt gcc aag    1302
Glu Leu Gly Glu Lys Tyr Lys Asp Ser Lys Asp Ile Val Val Ala Lys
    410                 415                 420 atg gat gcc act gcc aat gag att gaa gag gtc aaa gtg cag agc ttc    1350
Met Asp Ala Thr Ala Asn Glu Ile Glu Glu Val Lys Val Gln Ser Phe
425                 430                 435                 440 ccc acc ctc aag tac ttc ccc aag gac agc gat gag gct gtg gac tac    1398
Pro Thr Leu Lys Tyr Phe Pro Lys Asp Ser Asp Glu Ala Val Asp Tyr
                445                 450                 455 aat ggc gag aga acc ttg gat gct ttc gtc aaa ttc ctc gag agc ggt    1446
Asn Gly Glu Arg Thr Leu Asp Ala Phe Val Lys Phe Leu Glu Ser Gly
            460                 465                 470 ggc acg gaa ggt gct gga gtg caa gag gat gag gaa gag gaa gag gaa    1494
Gly Thr Glu Gly Ala Gly Val Gln Glu Asp Glu Glu Glu Glu Glu Glu
        475                 480                 485 gat gag gag ggt gat gat gaa gat ctg cca aga gat gaa ctg             1536
Asp Glu Glu Gly Asp Asp Glu Asp Leu Pro Arg Asp Glu Leu
    490                 495                 500 tagctgtcat cggcatctag actcgaaggg cgaattccag cacactggcg gccgttacta   1596
gtggatccga gctcggtacc aagcttggcg taatcatggt catagctgtt tcctgtgtga   1656
aattgttatc cgctcacaat tccacacaac atacgagccg gaagcataaa gtgtaaagcc   1716
tggggtgcct aatgagtgag ctaactcaca ttaattgcgt tgcgctcact gnccgctttc   1776
cagtcgggaa anctgtcgtg ccagctgcat taatgaatcg gccaacgcgc ggggaaaagg   1836
cggtttgcgt attgggcgct cttccgcttc ctcgctcact gactcgctgc gctcggtcgt   1896
tcggctgccg cgagcggta tcagctcact caangggga atacggtant ccacanatca    1956
ggggataccg caggaaanaa ntgtgaccaa angncan                            1993

<210> SEQ ID NO 8
<211> LENGTH: 502
<212> TYPE: PRT
<213> ORGANISM: Conus textile
<220> FEATURE:
<221> NAME/KEY: misc_feature
<222> LOCATION: (159)..(159)
<223> OTHER INFORMATION: The 'Xaa' at location 159 stands for Ile, Val,
      Leu, or Phe.

<400> SEQUENCE: 8

Met Lys Phe Ser Ser Cys Leu Val Leu Thr Leu Leu Val Phe Val Ser
1               5                   10                  15

Ala Glu Asp Val Lys Gln Glu Glu Gly Val Tyr Val Leu Thr Glu Lys
                20                  25                  30

Asn Phe Asp Ala Phe Ile Ser Asp Asn Glu Phe Val Leu Val Glu Phe
            35                  40                  45

Tyr Ala Pro Trp Cys Gly His Cys Lys Ala Leu Ala Pro Glu Tyr Ala
        50                  55                  60

Lys Ala Ala Thr Thr Leu Glu Glu Glu Lys Ser Asn Ile Lys Leu Gly
65                  70                  75                  80

Lys Val Asp Ala Thr Val Glu Val Asn Leu Ala Thr Lys Phe Glu Val
```

-continued

```
                    85                  90                  95
Arg Gly Tyr Pro Thr Ile Lys Phe Phe His Lys Glu Met Pro Ala Gly
            100                 105                 110
Ser Pro Ala Asp Tyr Ser Gly Gly Arg Gln Ala Pro Asp Ile Val Gly
            115                 120                 125
Trp Leu Lys Lys Lys Thr Gly Pro Pro Ala Lys Glu Leu Lys Ala Lys
            130                 135             140
Asp Glu Val Lys Thr Phe Val Glu Lys Asp Glu Val Val Xaa Gly
145                 150                 155                 160
Phe Phe Lys Asp Gln Glu Ser Thr Gly Ala Leu Ala Phe Lys Lys Ala
                165                 170                 175
Ala Ala Gly Ile Asp Asp Ile Pro Phe Ala Ile Thr Ser Glu Asp His
            180                 185                 190
Val Phe Lys Glu Tyr Lys Met Asp Lys Asp Gly Ile Val Leu Leu Lys
            195                 200                 205
Lys Phe Asp Glu Gly Arg Asn Asp Phe Glu Gly Asn Leu Glu Glu Glu
            210                 215                 220
Glu Ala Ile Val Lys His Val Arg Glu Asn Gln Leu Pro Leu Val Val
225                 230                 235                 240
Glu Phe Thr Gln Glu Ser Ala Gln Lys Ile Phe Gly Gly Glu Val Lys
                245                 250                 255
Asn His Ile Leu Leu Phe Leu Lys Lys Glu Gly Gly Glu Asp Thr Ile
            260                 265                 270
Glu Lys Phe Arg Gly Ala Ala Glu Asp Phe Lys Gly Lys Val Leu Phe
            275                 280                 285
Ile Tyr Leu Asp Thr Asp Asn Glu Glu Asn Gly Arg Ile Thr Glu Phe
            290                 295                 300
Phe Gly Leu Lys Asp Asp Glu Ile Pro Ala Val Arg Leu Ile Gln Leu
305                 310                 315                 320
Ala Glu Asp Met Ser Lys Tyr Lys Pro Glu Ser Ser Asp Leu Glu Thr
                325                 330                 335
Ala Thr Ile Lys Lys Phe Val Gln Asp Phe Leu Asp Gly Lys Leu Lys
            340                 345                 350
Pro His Leu Met Ser Glu Asp Val Pro Gly Asp Trp Asp Ala Lys Pro
            355                 360                 365
Val Lys Val Leu Val Gly Lys Asn Phe Lys Glu Val Ala Met Asp Lys
            370                 375                 380
Ser Lys Ala Val Phe Val Glu Phe Tyr Ala Pro Trp Cys Gly His Cys
385                 390                 395                 400
Lys Gln Leu Ala Pro Ile Trp Asp Glu Leu Gly Glu Lys Tyr Lys Asp
                405                 410                 415
Ser Lys Asp Ile Val Val Ala Lys Met Asp Ala Thr Ala Asn Glu Ile
            420                 425                 430
Glu Glu Val Lys Val Gln Ser Phe Pro Thr Leu Lys Tyr Phe Pro Lys
            435                 440                 445
Asp Ser Asp Glu Ala Val Asp Tyr Asn Gly Glu Arg Thr Leu Asp Ala
450                 455                 460
Phe Val Lys Phe Leu Glu Ser Gly Gly Thr Glu Gly Ala Gly Val Gln
465                 470                 475                 480
Glu Asp Glu Glu Glu Glu Glu Asp Glu Glu Gly Asp Asp Glu Asp
                485                 490                 495
Leu Pro Arg Asp Glu Leu
            500
```

<210> SEQ ID NO 9
<211> LENGTH: 494
<212> TYPE: PRT
<213> ORGANISM: Bombyx mori
<220> FEATURE:
<221> NAME/KEY: MISC_FEATURE
<222> LOCATION: (1)..(494)
<223> OTHER INFORMATION: Genbank Accession Number: AAG45936

<400> SEQUENCE: 9

```
Met Arg Val Leu Ile Phe Thr Ala Ile Ala Leu Leu Gly Leu Ala Leu
1               5                   10                  15

Gly Asp Glu Val Pro Thr Glu Asn Val Leu Val Leu Ser Lys Ala
            20                  25                  30

Asn Phe Glu Thr Val Ile Ser Thr Glu Tyr Ile Leu Val Glu Phe
        35                  40                  45

Tyr Ala Pro Trp Cys Gly His Cys Lys Ser Leu Ala Pro Glu Tyr Ala
    50                  55                  60

Lys Ala Ala Thr Lys Leu Ala Glu Glu Ser Pro Ile Lys Leu Ala
65              70                  75                  80

Lys Val Asp Ala Thr Gln Glu Gln Asp Leu Ala Glu Ser Tyr Gly Val
            85                  90                  95

Arg Gly Tyr Pro Thr Leu Lys Phe Phe Arg Asn Gly Ser Pro Ile Asp
            100                 105                 110

Tyr Ser Gly Gly Arg Gln Ala Asp Asp Ile Ile Ser Trp Leu Lys Lys
        115                 120                 125

Lys Thr Gly Pro Pro Ala Val Glu Val Thr Ser Ala Glu Gln Ala Lys
    130                 135                 140

Glu Leu Ile Asp Ala Asn Thr Val Ile Val Phe Gly Phe Phe Ser Asp
145                 150                 155                 160

Gln Ser Ser Thr Arg Ala Lys Thr Phe Leu Ser Thr Ala Gln Val Val
                165                 170                 175

Asp Asp Gln Val Phe Ala Ile Val Ser Asp Glu Lys Val Ile Lys Glu
            180                 185                 190

Leu Glu Ala Glu Asp Glu Asp Val Val Leu Phe Lys Asn Phe Glu Glu
        195                 200                 205

Lys Arg Val Lys Tyr Glu Asp Glu Ile Thr Glu Asp Leu Leu Asn
    210                 215                 220

Ala Trp Val Phe Val Gln Ser Met Pro Thr Ile Val Glu Phe Ser His
225                 230                 235                 240

Glu Thr Ala Ser Lys Ile Phe Gly Gly Lys Ile Lys Tyr His Leu Leu
                245                 250                 255

Ile Phe Leu Ser Lys Lys Asn Gly Asp Phe Glu Lys Tyr Leu Glu Asp
            260                 265                 270

Leu Lys Pro Val Ala Lys Thr Tyr Arg Asp Arg Ile Met Thr Val Ala
        275                 280                 285

Ile Asp Ala Asp Glu Asp Glu His Gln Arg Ile Leu Glu Phe Phe Gly
    290                 295                 300

Met Lys Lys Asp Glu Val Pro Ser Ala Arg Leu Ile Ala Leu Glu Gln
305                 310                 315                 320

Asp Met Ala Lys Tyr Lys Pro Ser Ser Asn Glu Leu Ser Pro Asn Ala
                325                 330                 335

Ile Glu Glu Phe Val Gln Ser Phe Phe Asp Gly Thr Leu Lys Gln His
            340                 345                 350
```

```
Leu Leu Ser Glu Asp Leu Pro Ala Asp Trp Ala Ala Lys Pro Val Lys
        355                 360                 365

Val Leu Val Ala Ala Asn Phe Asp Glu Val Val Phe Asp Thr Thr Lys
    370                 375                 380

Lys Val Leu Val Glu Phe Tyr Ala Pro Trp Cys Gly His Cys Lys Gln
385                 390                 395                 400

Leu Val Pro Ile Tyr Asp Lys Leu Gly Glu His Phe Glu Asn Asp Asp
            405                 410                 415

Asp Val Ile Ile Ala Lys Ile Asp Ala Thr Ala Asn Glu Leu Glu His
                420                 425                 430

Thr Lys Ile Thr Ser Phe Ser Thr Ile Lys Leu Tyr Ser Lys Asp Asn
        435                 440                 445

Gln Val His Asp Tyr Asn Gly Glu Arg Thr Leu Ala Gly Leu Thr Lys
    450                 455                 460

Phe Val Glu Thr Asp Gly Glu Gly Ala Glu Pro Val Pro Ser Val Thr
465                 470                 475                 480

Glu Phe Glu Glu Glu Glu Asp Val Pro Ala Lys Asp Glu Leu
            485                 490

<210> SEQ ID NO 10
<211> LENGTH: 496
<212> TYPE: PRT
<213> ORGANISM: Strongylocentrotus purpuratus
<220> FEATURE:
<221> NAME/KEY: MISC_FEATURE
<222> LOCATION: (1)..(496)
<223> OTHER INFORMATION: Genbank Accession Number: A54757

<400> SEQUENCE: 10

Met Lys Tyr Leu Ala Leu Cys Phe Ile Ala Leu Ala Cys Ala Val His
1               5                   10                  15

Ala Ala Val Glu Val Glu Ile Glu Gly Asp Val Ala Val Leu Thr Asp
            20                  25                  30

Ala Ala Phe Ala Asp Tyr Val Ala Glu Asn Glu Phe Val Leu Val Glu
        35                  40                  45

Phe Tyr Ala Pro Trp Cys Gly His Cys Lys Ser Leu Ala Pro Gln Tyr
    50                  55                  60

Ser Ile Ala Ala Lys Thr Leu Lys Asp Ser Gly Ser Ser Ile Lys Leu
65                  70                  75                  80

Ala Lys Val Asp Ala Thr Val Glu Thr Gln Leu Pro Gly Lys Tyr Gly
                85                  90                  95

Val Arg Gly Tyr Pro Thr Leu Lys Phe Phe Arg Ser Gly Lys Asp Ser
            100                 105                 110

Glu Tyr Ala Gly Gly Arg Thr Gly Pro Glu Ile Val Ala Trp Leu Asn
        115                 120                 125

Lys Lys Thr Gly Pro Pro Ala Ala Thr Ile Ala Ser Val Glu Asp Ala
    130                 135                 140

Glu Ala Phe Leu Ala Asp Lys Glu Val Ala Val Ile Gly Phe Phe Lys
145                 150                 155                 160

Asp Val Pro Gln Thr Phe Leu Asp Val Ala Val Asn Ile Asp Asp Ile
                165                 170                 175

Pro Phe Ala Ile Val Ser Asp Asp Ala Val Ile Ser Asn Tyr Glu Ala
            180                 185                 190

Lys Asp Gly Ser Ile Ile Leu Phe Lys Lys Phe Asp Glu Gly Lys Asn
        195                 200                 205

Val Phe Glu Gly Glu Leu Thr Ser Glu Asp Leu Thr Ser Phe Val Arg
```

-continued

```
                    210                 215                 220
Lys Asn Ser Leu Ser Val Val Thr Glu Phe Gly Glu Glu Thr Ala Ser
225                 230                 235                 240

Lys Ile Phe Gly Gly Glu Ile Lys Ile His Asn Leu Leu Phe Val Lys
                245                 250                 255

Lys Asp Ser Asp Asp Phe Lys Thr Ile Tyr Asp Gln Phe Tyr Ala Ala
            260                 265                 270

Ala Thr Thr Phe Lys Gly Glu Val Leu Phe Val Leu Ile Asp Ala Ala
        275                 280                 285

Ala Glu Ser Asn Ser Arg Ile Leu Glu Tyr Phe Gly Leu Gly Asp Glu
    290                 295                 300

Glu Val Pro Thr Val Arg Leu Ile Thr Leu Asp Gly Asp Met Lys Lys
305                 310                 315                 320

Tyr Lys Pro Thr Val Pro Glu Leu Thr Thr Glu Ser Leu Ser Gln Phe
                325                 330                 335

Val Ile Asp Phe Lys Asp Gly Lys Leu Lys Pro His Leu Met Ser Glu
            340                 345                 350

Ser Val Pro Glu Asp Trp Asn Ala Asn Pro Val Thr Ile Leu Val Gly
        355                 360                 365

Glu Asn Phe Ala Glu Val Ala Leu Asp Pro Thr Lys Asp Val Leu Val
    370                 375                 380

Glu Phe Tyr Ala Pro Trp Cys Gly His Cys Lys Gln Leu Ala Pro Ile
385                 390                 395                 400

Tyr Glu Glu Leu Gly Glu His Phe Lys Glu Arg Glu Asp Val Val Ile
                405                 410                 415

Ala Lys Val Asp Ser Thr Lys Asn Glu Val Glu Asp Ala Val Val Arg
            420                 425                 430

Ser Phe Pro Thr Leu Lys Phe Trp Lys Gly Glu Asn Glu Met Val
        435                 440                 445

Asp Tyr Ser Gly Asp Arg Thr Leu Glu Ala Met Ile Gln Phe Val Glu
    450                 455                 460

Ser Gly Gly Glu Ile Ile Ala Glu Val Asp Asp Glu Asp Met Glu Glu
465                 470                 475                 480

Asp Glu Glu Met Asp Glu Gly Ala Glu Asp Gln Ala Lys Asp Glu Leu
                485                 490                 495

<210> SEQ ID NO 11
<211> LENGTH: 509
<212> TYPE: PRT
<213> ORGANISM: Rattus norvegicus
<220> FEATURE:
<221> NAME/KEY: MISC_FEATURE
<222> LOCATION: (1)..(509)
<223> OTHER INFORMATION: Genbank Accession Number: NP_037130

<400> SEQUENCE: 11

Met Leu Ser Arg Ala Leu Leu Cys Leu Ala Leu Ala Trp Ala Ala Arg
1               5                   10                  15

Val Gly Ala Asp Ala Leu Glu Glu Glu Asp Asn Val Leu Val Leu Lys
            20                  25                  30

Lys Ser Asn Phe Ala Glu Ala Leu Ala Ala His Asn Tyr Leu Leu Val
        35                  40                  45

Glu Phe Tyr Ala Pro Trp Cys Gly His Cys Lys Ala Leu Ala Pro Glu
    50                  55                  60

Tyr Ala Lys Ala Ala Ala Lys Leu Lys Ala Glu Gly Ser Glu Ile Arg
65                  70                  75                  80
```

Leu Ala Lys Val Asp Ala Thr Glu Glu Ser Asp Leu Ala Gln Gln Tyr
            85                  90                  95

Gly Val Arg Gly Tyr Pro Thr Ile Lys Phe Phe Lys Asn Gly Asp Thr
            100                 105                 110

Ala Ser Pro Lys Glu Tyr Thr Ala Gly Arg Glu Ala Asp Asp Ile Val
            115                 120                 125

Asn Trp Leu Lys Lys Arg Thr Gly Pro Ala Ala Thr Thr Leu Ser Asp
    130                 135                 140

Thr Ala Ala Glu Ser Leu Val Asp Ser Ser Glu Val Thr Val Ile
145                 150                 155                 160

Gly Phe Phe Lys Asp Ala Gly Ser Asp Ser Ala Lys Gln Phe Leu Leu
                165                 170                 175

Ala Ala Glu Ala Val Asp Asp Ile Pro Phe Gly Ile Thr Ser Asn Ser
                180                 185                 190

Asp Val Phe Ser Lys Tyr Gln Leu Asp Lys Asp Gly Val Val Leu Phe
            195                 200                 205

Lys Lys Phe Asp Glu Gly Arg Asn Asn Phe Glu Gly Glu Ile Thr Lys
            210                 215                 220

Glu Lys Leu Leu Asp Phe Ile Lys His Asn Gln Leu Pro Leu Val Ile
225                 230                 235                 240

Glu Phe Thr Glu Gln Thr Ala Pro Lys Ile Phe Gly Gly Glu Ile Lys
                245                 250                 255

Thr His Ile Leu Leu Phe Leu Pro Lys Ser Val Ser Asp Tyr Asp Gly
                260                 265                 270

Lys Leu Ser Asn Phe Lys Lys Ala Ala Glu Gly Phe Lys Gly Lys Ile
            275                 280                 285

Leu Phe Ile Phe Ile Asp Ser Asp His Thr Asp Asn Gln Arg Ile Leu
            290                 295                 300

Glu Phe Phe Gly Leu Lys Lys Glu Glu Cys Pro Ala Val Arg Leu Ile
305                 310                 315                 320

Thr Leu Glu Glu Glu Met Thr Lys Tyr Lys Pro Glu Ser Asp Glu Leu
                325                 330                 335

Thr Ala Glu Lys Ile Thr Gln Phe Cys His His Phe Leu Glu Gly Lys
                340                 345                 350

Ile Lys Pro His Leu Met Ser Gln Glu Leu Pro Glu Asp Trp Asp Lys
            355                 360                 365

Gln Pro Val Lys Val Leu Val Gly Lys Asn Phe Glu Glu Val Ala Phe
    370                 375                 380

Asp Glu Lys Lys Asn Val Phe Val Glu Phe Tyr Ala Pro Trp Cys Gly
385                 390                 395                 400

His Cys Lys Gln Leu Ala Pro Ile Trp Asp Lys Leu Gly Glu Thr Tyr
                405                 410                 415

Lys Asp His Glu Asn Ile Val Ile Ala Lys Met Asp Ser Thr Ala Asn
            420                 425                 430

Glu Val Glu Ala Val Lys Val His Ser Phe Pro Thr Leu Lys Phe Phe
            435                 440                 445

Pro Ala Ser Ala Asp Arg Thr Val Ile Asp Tyr Asn Gly Glu Arg Thr
    450                 455                 460

Leu Asp Gly Phe Lys Lys Phe Leu Glu Ser Gly Gly Gln Asp Gly Ala
465                 470                 475                 480

Gly Asp Asn Asp Asp Leu Asp Leu Glu Glu Ala Leu Glu Pro Asp Met
                485                 490                 495

```
Glu Glu Asp Asp Asp Gln Lys Ala Val Lys Asp Glu Leu
            500                 505
```

<210> SEQ ID NO 12
<211> LENGTH: 508
<212> TYPE: PRT
<213> ORGANISM: Homo sapiens
<220> FEATURE:
<221> NAME/KEY: MISC_FEATURE
<222> LOCATION: (1)..(508)
<223> OTHER INFORMATION: Genbank Accession Number: CAA28775

<400> SEQUENCE: 12

```
Met Leu Arg Arg Ala Leu Leu Cys Leu Ala Val Ala Leu Val Arg
1               5                   10                  15

Ala Asp Ala Pro Glu Glu Glu Asp His Val Leu Val Leu Arg Lys Ser
                20                  25                  30

Asn Phe Ala Glu Ala Leu Ala Ala His Lys Tyr Leu Leu Val Glu Phe
            35                  40                  45

Tyr Ala Pro Trp Cys Gly His Cys Lys Ala Leu Ala Pro Glu Tyr Ala
        50                  55                  60

Lys Ala Ala Gly Lys Leu Lys Ala Glu Gly Ser Glu Ile Arg Leu Ala
65                  70                  75                  80

Lys Val Asp Ala Thr Glu Glu Ser Asp Leu Ala Gln Gln Tyr Gly Val
                85                  90                  95

Arg Gly Tyr Pro Thr Ile Lys Phe Phe Arg Asn Gly Asp Thr Ala Ser
            100                 105                 110

Pro Lys Glu Tyr Thr Ala Gly Arg Glu Ala Asp Asp Ile Val Asn Trp
        115                 120                 125

Leu Lys Lys Arg Thr Gly Pro Ala Ala Thr Thr Leu Pro Asp Gly Ala
    130                 135                 140

Ala Ala Glu Ser Leu Val Glu Ser Ser Glu Val Ala Val Ile Gly Phe
145                 150                 155                 160

Phe Lys Asp Val Glu Ser Asp Ser Ala Lys Gln Phe Leu Gln Ala Ala
                165                 170                 175

Glu Ala Ile Asp Asp Ile Pro Phe Gly Ile Thr Ser Asn Ser Asp Val
            180                 185                 190

Phe Ser Lys Tyr Gln Leu Asp Lys Asp Gly Val Val Leu Phe Lys Lys
        195                 200                 205

Phe Asp Glu Gly Arg Asn Asn Phe Glu Gly Glu Val Thr Lys Glu Asn
    210                 215                 220

Leu Leu Asp Phe Ile Lys His Asn Gln Leu Pro Leu Val Ile Glu Phe
225                 230                 235                 240

Thr Glu Gln Thr Ala Pro Lys Ile Phe Gly Gly Glu Ile Lys Thr His
                245                 250                 255

Ile Leu Leu Phe Leu Pro Lys Ser Val Ser Asp Tyr Asp Gly Lys Leu
            260                 265                 270

Ser Asn Phe Lys Thr Ala Ala Glu Ser Phe Lys Gly Lys Ile Leu Phe
        275                 280                 285

Ile Phe Ile Asp Ser Asp His Thr Asp Asn Gln Arg Ile Leu Glu Phe
    290                 295                 300

Phe Gly Leu Lys Lys Glu Glu Cys Pro Ala Val Arg Leu Ile Thr Leu
305                 310                 315                 320

Glu Glu Glu Met Thr Lys Tyr Lys Pro Glu Ser Glu Glu Leu Thr Ala
                325                 330                 335

Glu Arg Ile Thr Glu Phe Cys His Arg Phe Leu Glu Gly Lys Ile Lys
```

```
                    340                 345                 350
Pro His Leu Met Ser Gln Glu Leu Pro Glu Asp Trp Asp Lys Gln Pro
        355                 360                 365

Val Lys Val Leu Val Gly Lys Asn Phe Glu Asp Val Ala Phe Asp Glu
    370                 375                 380

Lys Lys Asn Val Phe Val Glu Phe Tyr Ala Pro Trp Cys Gly His Cys
385                 390                 395                 400

Lys Gln Leu Ala Pro Ile Trp Asp Lys Leu Gly Glu Thr Tyr Lys Asp
                405                 410                 415

His Glu Asn Ile Val Ile Ala Lys Met Asp Ser Thr Ala Asn Glu Val
            420                 425                 430

Glu Ala Val Lys Val His Ser Phe Pro Thr Leu Lys Phe Phe Pro Ala
        435                 440                 445

Ser Ala Asp Arg Thr Val Ile Asp Tyr Asn Gly Glu Arg Thr Leu Asp
    450                 455                 460

Gly Phe Lys Lys Phe Leu Glu Ser Gly Gly Gln Asp Gly Ala Gly Asp
465                 470                 475                 480

Asp Asp Asp Leu Glu Asp Leu Glu Glu Ala Glu Glu Pro Asp Met Glu
                485                 490                 495

Glu Asp Asp Asp Gln Lys Ala Val Lys Asp Glu Leu
                500                 505

<210> SEQ ID NO 13
<211> LENGTH: 496
<212> TYPE: PRT
<213> ORGANISM: Drosophila melanogaster
<220> FEATURE:
<221> NAME/KEY: MISC_FEATURE
<222> LOCATION: (1)..(496)
<223> OTHER INFORMATION: Genbank Accession Number: NP_524079

<400> SEQUENCE: 13

Met Lys Phe Leu Ile Cys Ala Leu Phe Leu Ala Ala Ser Tyr Val Ala
1               5                   10                  15

Ala Ser Ala Glu Ala Glu Val Lys Val Glu Glu Gly Val Leu Val Ala
            20                  25                  30

Thr Val Asp Asn Phe Lys Gln Leu Ile Ala Asp Asn Glu Phe Val Leu
        35                  40                  45

Val Glu Phe Tyr Ala Pro Trp Cys Gly His Cys Lys Ala Leu Ala Pro
    50                  55                  60

Glu Tyr Ala Lys Ala Ala Gln Gln Leu Ala Glu Lys Glu Ser Pro Ile
65                  70                  75                  80

Lys Leu Ala Lys Val Asp Ala Thr Val Glu Gly Glu Leu Ala Glu Gln
                85                  90                  95

Tyr Ala Val Arg Gly Tyr Pro Thr Leu Lys Phe Phe Arg Ser Gly Ser
            100                 105                 110

Pro Val Glu Tyr Ser Gly Gly Arg Gln Ala Ala Asp Ile Ala Trp
        115                 120                 125

Val Thr Lys Lys Thr Gly Pro Pro Ala Lys Asp Leu Thr Ser Val Ala
    130                 135                 140

Asp Ala Glu Gln Phe Leu Lys Asp Asn Glu Ile Ala Ile Gly Phe
145                 150                 155                 160

Phe Lys Asp Leu Glu Ser Glu Ala Lys Thr Phe Thr Lys Val Ala
                165                 170                 175

Asn Ala Leu Asp Ser Phe Val Phe Gly Val Ser Ser Asn Ala Asp Val
            180                 185                 190
```

```
Ile Ala Lys Tyr Glu Ala Lys Asp Asn Gly Val Val Leu Phe Lys Pro
            195                 200                 205

Phe Asp Asp Lys Lys Ser Val Phe Glu Gly Glu Leu Asn Glu Glu Asn
        210                 215                 220

Leu Lys Lys Phe Ala Gln Val Gln Ser Leu Pro Leu Ile Val Asp Phe
225                 230                 235                 240

Asn His Glu Ser Ala Ser Lys Ile Phe Gly Gly Ser Ile Lys Ser His
            245                 250                 255

Leu Leu Phe Phe Val Ser Arg Glu Gly Gly His Ile Glu Lys Tyr Val
            260                 265                 270

Asp Pro Leu Lys Glu Ile Ala Lys Lys Tyr Arg Asp Asp Ile Leu Phe
            275                 280                 285

Val Thr Ile Ser Ser Asp Glu Asp His Thr Arg Ile Phe Glu Phe
            290                 295                 300

Phe Gly Met Asn Lys Glu Glu Val Pro Thr Ile Arg Leu Ile Lys Leu
305                 310                 315                 320

Glu Glu Asp Met Ala Lys Tyr Lys Pro Glu Ser Asp Asp Leu Ser Ala
            325                 330                 335

Glu Thr Ile Glu Ala Phe Leu Lys Lys Phe Leu Asp Gly Lys Leu Lys
            340                 345                 350

Gln His Leu Leu Ser Gln Glu Leu Pro Glu Asp Trp Asp Lys Asn Pro
            355                 360                 365

Val Lys Val Leu Val Ser Ser Asn Phe Glu Ser Val Ala Leu Asp Lys
            370                 375                 380

Ser Lys Ser Val Leu Val Glu Phe Tyr Ala Pro Trp Cys Gly His Cys
385                 390                 395                 400

Lys Gln Leu Ala Pro Ile Tyr Asp Gln Leu Ala Glu Lys Tyr Lys Asp
                405                 410                 415

Asn Glu Asp Ile Val Ile Ala Lys Met Asp Ser Thr Ala Asn Glu Leu
            420                 425                 430

Glu Ser Ile Lys Ile Ser Ser Phe Pro Thr Ile Lys Tyr Phe Arg Lys
            435                 440                 445

Glu Asp Asn Lys Val Ile Asp Phe Asn Leu Asp Arg Thr Leu Asp Asp
        450                 455                 460

Phe Val Lys Phe Leu Asp Ala Asn Gly Glu Val Ala Asp Ser Glu Pro
465                 470                 475                 480

Val Glu Glu Thr Glu Glu Glu Glu Ala Pro Lys Lys Asp Glu Leu
            485                 490                 495

<210> SEQ ID NO 14
<211> LENGTH: 493
<212> TYPE: PRT
<213> ORGANISM: Caenorhabditis elegans
<220> FEATURE:
<221> NAME/KEY: MISC_FEATURE
<222> LOCATION: (1)..(493)
<223> OTHER INFORMATION: Genbank Accession Number: S44756

<400> SEQUENCE: 14

Met Phe Arg Leu Val Gly Leu Phe Phe Leu Val Leu Gly Ala Ser Ala
1               5                   10                  15

Ala Val Ile Glu Glu Glu Glu Asn Val Ile Val Leu Thr Lys Asp Asn
            20                  25                  30

Phe Asp Glu Val Ile Asn Gly Asn Glu Phe Ile Leu Val Glu Phe Tyr
        35                  40                  45
```

```
Ala Pro Trp Cys Gly His Cys Lys Ser Leu Ala Pro Glu Tyr Ala Lys
 50                  55                  60
Ala Ala Thr Gln Leu Lys Glu Glu Gly Ser Asp Ile Lys Leu Gly Lys
 65                  70                  75                  80
Leu Asp Ala Thr Val His Gly Glu Val Ser Ser Lys Phe Glu Val Arg
                 85                  90                  95
Gly Tyr Pro Thr Leu Lys Leu Phe Arg Asn Gly Lys Pro Gln Glu Tyr
            100                 105                 110
Asn Gly Gly Arg Asp His Asp Ser Ile Ile Ala Trp Leu Lys Lys Lys
            115                 120                 125
Thr Gly Pro Val Ala Lys Pro Leu Ala Asp Ala Asp Ala Val Lys Glu
            130                 135                 140
Leu Gln Glu Ser Ala Asp Val Val Ile Gly Tyr Phe Lys Asp Thr
145                 150                 155                 160
Thr Ser Asp Asp Ala Lys Thr Phe Leu Glu Val Ala Ala Gly Ile Asp
                165                 170                 175
Asp Val Pro Phe Gly Ile Ser Thr Glu Asp Ala Val Lys Ser Glu Ile
                180                 185                 190
Glu Leu Lys Gly Glu Gly Ile Val Leu Phe Lys Lys Phe Asp Asp Gly
            195                 200                 205
Arg Val Ala Phe Asp Glu Lys Leu Thr Gln Asp Gly Leu Lys Thr Trp
            210                 215                 220
Ile Gln Ala Asn Arg Leu Ala Leu Val Ser Glu Phe Thr Gln Glu Thr
225                 230                 235                 240
Ala Ser Val Ile Phe Gly Gly Glu Ile Lys Ser His Asn Leu Leu Phe
                245                 250                 255
Val Ser Lys Glu Ser Ser Glu Phe Ala Lys Leu Glu Gln Glu Phe Lys
            260                 265                 270
Asn Ala Ala Lys Gln Phe Lys Gly Lys Val Leu Phe Val Tyr Ile Asn
            275                 280                 285
Thr Asp Val Glu Glu Asn Ala Arg Ile Met Glu Phe Phe Gly Leu Lys
            290                 295                 300
Lys Asp Glu Leu Pro Ala Ile Arg Leu Ile Ser Leu Glu Glu Asp Met
305                 310                 315                 320
Thr Lys Phe Lys Pro Asp Phe Glu Glu Ile Thr Thr Glu Asn Ile Ser
                325                 330                 335
Lys Phe Thr Gln Asn Tyr Leu Asp Gly Ser Val Lys Pro His Leu Met
            340                 345                 350
Ser Glu Asp Ile Pro Glu Asp Trp Asp Lys Asn Pro Val Lys Ile Leu
            355                 360                 365
Val Gly Lys Asn Phe Glu Gln Val Ala Arg Asp Asn Thr Lys Asn Val
            370                 375                 380
Leu Val Glu Phe Tyr Ala Pro Trp Cys Gly His Cys Lys Gln Leu Ala
385                 390                 395                 400
Pro Thr Trp Asp Lys Leu Gly Glu Lys Phe Ala Asp Asp Glu Ser Ile
                405                 410                 415
Val Ile Ala Lys Met Asp Ser Thr Leu Asn Glu Val Glu Asp Val Lys
                420                 425                 430
Ile Gln Ser Phe Pro Thr Ile Lys Phe Phe Pro Ala Gly Ser Asn Lys
            435                 440                 445
Val Val Asp Tyr Thr Gly Asp Arg Thr Ile Glu Gly Phe Thr Lys Phe
            450                 455                 460
Leu Glu Thr Asn Gly Lys Glu Gly Ala Gly Ala Ser Glu Glu Glu Lys
```

```
            465                 470                 475                 480
Ala Glu Glu Glu Ala Asp Glu Glu Gly His Thr Glu Leu
                485                 490
```

<210> SEQ ID NO 15
<211> LENGTH: 7
<212> TYPE: PRT
<213> ORGANISM: Artificial
<220> FEATURE:
<223> OTHER INFORMATION: Amino acids encoded at Forward Primer 1

<400> SEQUENCE: 15

```
Val Glu Phe Tyr Ala Pro Trp
1               5
```

<210> SEQ ID NO 16
<211> LENGTH: 21
<212> TYPE: DNA
<213> ORGANISM: Artificial
<220> FEATURE:
<223> OTHER INFORMATION: Forward Primer 1
<220> FEATURE:
<221> NAME/KEY: misc_feature
<222> LOCATION: (3)..(3)
<223> OTHER INFORMATION: n is any nucleic acid
<220> FEATURE:
<221> NAME/KEY: misc_feature
<222> LOCATION: (6)..(6)
<223> OTHER INFORMATION: r is a purine
<220> FEATURE:
<221> NAME/KEY: misc_feature
<222> LOCATION: (9)..(9)
<223> OTHER INFORMATION: y is a pyrimidine
<220> FEATURE:
<221> NAME/KEY: misc_feature
<222> LOCATION: (12)..(12)
<223> OTHER INFORMATION: y is a pyrimidine
<220> FEATURE:
<221> NAME/KEY: misc_feature
<222> LOCATION: (15)..(15)
<223> OTHER INFORMATION: n is any nucleic acid
<220> FEATURE:
<221> NAME/KEY: misc_feature
<222> LOCATION: (18)..(18)
<223> OTHER INFORMATION: n is any nucleic acid

<400> SEQUENCE: 16
gtngarttyt aygcnccntg g                                              21

<210> SEQ ID NO 17
<211> LENGTH: 7
<212> TYPE: PRT
<213> ORGANISM: Artificial
<220> FEATURE:
<223> OTHER INFORMATION: Amino acids encoded at Reverse Primer1

<400> SEQUENCE: 17

```
Trp Cys Gly His Cys Lys Gln
1               5
```

<210> SEQ ID NO 18
<211> LENGTH: 21
<212> TYPE: DNA
<213> ORGANISM: Artificial
<220> FEATURE:
<223> OTHER INFORMATION: Reverse Primer 1
<220> FEATURE:
<221> NAME/KEY: misc_feature
<222> LOCATION: (1)..(1)
<223> OTHER INFORMATION: y is a pyrimidine
<220> FEATURE:

```
<221> NAME/KEY: misc_feature
<222> LOCATION: (4)..(4)
<223> OTHER INFORMATION: y is a pyrimidine
<220> FEATURE:
<221> NAME/KEY: misc_feature
<222> LOCATION: (7)..(7)
<223> OTHER INFORMATION: r is a purine
<220> FEATURE:
<221> NAME/KEY: misc_feature
<222> LOCATION: (10)..(10)
<223> OTHER INFORMATION: r is a purine
<220> FEATURE:
<221> NAME/KEY: misc_feature
<222> LOCATION: (13)..(13)
<223> OTHER INFORMATION: n is any nucleic acid
<220> FEATURE:
<221> NAME/KEY: misc_feature
<222> LOCATION: (16)..(16)
<223> OTHER INFORMATION: r is a purine

<400> SEQUENCE: 18
ytgyttrcar tgnccrcacc a                                     21

<210> SEQ ID NO 19
<211> LENGTH: 4
<212> TYPE: PRT
<213> ORGANISM: Artificial
<220> FEATURE:
<223> OTHER INFORMATION: redox active site

<400> SEQUENCE: 19

Cys Gly His Cys
1

<210> SEQ ID NO 20
<211> LENGTH: 4
<212> TYPE: PRT
<213> ORGANISM: Artificial
<220> FEATURE:
<223> OTHER INFORMATION: endoplasmic reticulum retrieval signal

<400> SEQUENCE: 20

Lys Asp Glu Leu
1

<210> SEQ ID NO 21
<211> LENGTH: 10
<212> TYPE: PRT
<213> ORGANISM: Conus textile

<400> SEQUENCE: 21

Glu Glu Val Glu Gln Glu Glu Asn Val Tyr
1               5                   10
```